(12) United States Patent
Bekkali et al.

(10) Patent No.: US 6,841,571 B2
(45) Date of Patent: Jan. 11, 2005

(54) COMPOUNDS USEFUL AS REVERSIBLE INHIBITORS OF CYSTEINE PROTEASES

(75) Inventors: Younes Bekkali, Danbury, CT (US); Denice Mary Spero, West Redding, CT (US); Sanxing Sun, Danbury, CT (US); Yancey David Ward, Sandy Hook, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 31 days.

(21) Appl. No.: 10/279,424

(22) Filed: Oct. 24, 2002

(65) Prior Publication Data

US 2004/0053921 A1 Mar. 18, 2004

Related U.S. Application Data

(60) Provisional application No. 60/340,719, filed on Oct. 29, 2001.

(51) Int. Cl.[7] .................. A61K 31/341; C07D 307/32
(52) U.S. Cl. ............... 514/473; 514/471; 549/472; 549/473; 549/475; 549/480
(58) Field of Search ................ 549/475, 472, 549/473, 480; 514/471, 473

(56) References Cited

U.S. PATENT DOCUMENTS

| 5,776,718 A | 7/1998 | Palmer et al. |
| 6,395,897 B1 | 5/2002 | Cywin et al. |
| 6,420,364 B1 | 7/2002 | Emmanuel et al. |

FOREIGN PATENT DOCUMENTS

| WO | WO 99/24460 | 5/1999 |
| WO | WO 99/56765 | 11/1999 |
| WO | WO 00/55125 | 9/2000 |
| WO | WO 00/55126 | 9/2000 |
| WO | WO 00/69855 | 11/2000 |
| WO | WO 01/19796 A1 | 3/2001 |
| WO | WO 01/19808 | 3/2001 |
| WO | WO 01/19816 A1 | 3/2001 |

*Primary Examiner*—Ba K. Trinh
(74) *Attorney, Agent, or Firm*—Robert P. Raymond; Anthony P. Bottino; Timothy X. Witkowski

(57) ABSTRACT

Disclosed are cathepsin S, K, F, L and B reversible inhibitory compounds of the formulas (Ia) and (Ib) where $R_2$, $R_3$, $R_4$, $R_6$, $R_8$ and Y are defined herein. The compounds are useful for treating autoimmune and other diseases. Also disclosed are processes for making such novel compounds

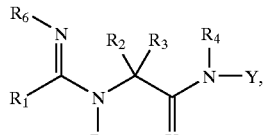

(Ia)

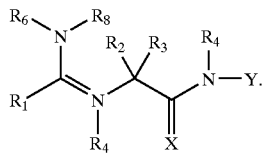

(Ib)

23 Claims, No Drawings

COMPOUNDS USEFUL AS REVERSIBLE INHIBITORS OF CYSTEINE PROTEASES

APPLICATION DATA

This application claims benefit to U.S. provisional application 60/340,719, filed Oct. 29, 2001.

TECHNICAL FIELD OF THE INVENTION

This invention relates to amidino and guanidino peptidyl compounds active as cysteine protease inhibitors. The compounds are reversible inhibitors of the cysteine protease cathepsin S, K, F, L and B are therefore useful in the treatment of autoimmune and other diseases. The invention also relates to processes for preparing such compounds and pharmaceutical compositions comprising them.

BACKGROUND OF THE INVENTION

Cathepsin S and cathepsin K are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207).

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immunoregulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999).

A cathepsin S inhibitor has been found to block the rise in IgE titers and eosinophil filtration in the lung in a mouse model of pulmonary hypersensitivity, suggesting that cathepsin S may be involved in asthma (R. J. Riese et al., J. Clin. Investigation, 1998, 101, 351).

Another cysteine protease, cathepsin F has been found in macrophages and is also involved in antigen processing. It has been postulated that cathepsin F in stimulated lung macrophages and possibly other antigen presenting cells could play a role in airway inflammation (G.-P. Shi et al., J. Exp. Med., 2000, 191, 1177).

Cathepsin K, another cysteine protease has been found to be highly expressed in osteoclasts and to degrade bone collagen and other bone matrix proteins. Inhibitors of cathepsin K have been shown to inhibit bone resorption in mice. Therefore, cathepsin K may play a role in osteoclastic bone resorption and cathepsin K inhibitors may be useful in the treatment of diseases involving bone resorption such as osteoporosis (F. Lazner et al., Human Molecular Genetics, 1999, 8, 1839).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62)

are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). Other examples of cathepsin S inhibitors have been reported by E. T. Altmann et at, (WO 9924460, 1999) which describes dipeptide nitriles asserted to have activity as inhibitors of Cathepsins B, K, L and S. Axys publications WO 00/55125 and 00/55126 disclose peptidyl nitrites for cathepsin inhibition which possess spirocarbocyclic and spiroheterocyclic moieties at P1, Axys publications WO 01/19808 and WO 01/19796 disclose peptidyl nitrites possessing mandatory sulfonyl groups at P2.

Additional peptidyl nitrites have been reported as protease inhibitors. For example, both nitrites and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitriles as inhibitors of papain.

WO 00/69855 discloses furanone derivatives which are alleged to be selective cathepsin S inhibitors. These compounds possess a furanone derived structure at the peptidyl 1 (P1) position.

WO 01/19816 discloses peptidyl nitrites with amindine or guanidine at the peptidyl 3 (P3) position. The compounds are disclosed as being reversible inhibitors of cysteine proteases cathepsin S, K, F, L and B.

None of the aforementioned publications disclose compounds which are reversible inhibitors of cysteine proteases cathepsin S, K, F, L and B, and structurally possessing a mandatory guanidino or amidino at the P3 position and a furanone derivative at the P1 position.

A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases such as cathepsin S and cathepsin K for indications in which these proteases exacerbate disease. All references cited in this application are incorporated by reference herein in their entirety.

BRIEF SUMMARY OF THE INVENTION

It is therefore an object of this invention to provide novel compounds according to the formula (Ia/Ib) as described herein which reversibly inhibit the cysteine proteases cathepsin S, K, F, L and B. It is a further object of the invention to provide methods for treating diseases and pathological conditions exacerbated by these cysteine proteases such as, but not limited, to rheumatoid arthritis, multiple sclerosis, asthma and osteoporosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases such as cathepsin S, K, F, L and B may be determined by the screens described in the section entitled "Assessment of Biological Properties."

Accordingly, in a first generic aspect of the invention, there are provided compounds of formula (Ia) and (Ib):

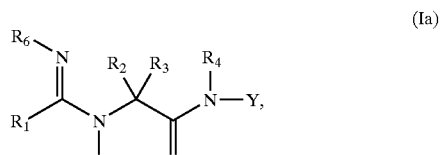

(Ia)

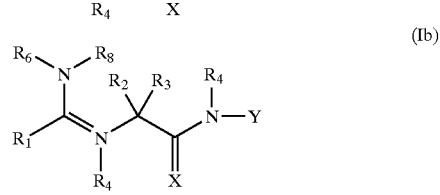

(Ib)

wherein for the formulas Ia or Ib:

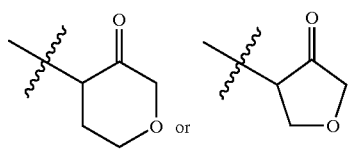

wherein Y is optionally substituted by one or more $R_5$;
$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8 cycloalkylsulfonylC1–10alkyl, arylsulfonylC1–10alkyl, heterocyclyl selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, heterocyclyloxy wherein the heterocyclyl moiety is selected from those herein described in this paragraph, hydroxy or amino; wherein $R_1$ is optionally substituted by one or more $R_a$, $R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10 alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$; with the proviso that $R_1$ and $R_a$ simultaneously cannot be a bond;

$R_b$ is a C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1 –4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;

or $R_b$ is C3–6 cycloalkyl, aryl, aryloxy, benzyloxy, halogen, hydroxy, oxo, carboxy, cyano, nitro, mono-C1 –6alkylamino, di-C1–5alkylamino, carboxamide, amidino or guanidino;

$R_2$ is hydrogen or $C_{1-3}$ alkyl;

$R_3$ is a bond, hydrogen, alkyl wherein one or more carbon atoms are optionally replaced by O, S or N wherein it shall be understood if N is not substituted by $R_c$ then it is NH, or $R_3$ is C2–10alkylene, heterocyclylC1–5 alkyl wherein the heterocyclic moiety is selected from pyrrolidinyl, piperidinyl, morpholinyl, thiomorpholinyl, 8-aza-bicyclo [3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl and quinoxalinyl, C3–8 cycloalkyl, arylC1–5 alkyl or aryl wherein $R_3$ is optionally substituted by one or more $R_c$;

$R_c$ is C3–8 cycloalkyl, aryl, indanyl, indenyl, bicyclo [2.2.1]heptanyl, bicyclo[2.2.2]octanyl, bicyclo[4.1.0] heptanyl, bicyclo[3.1.0]hexanyl, bicyclo[1.1.1] pentanyl, spiroC8–12 cycloalkyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, aryloxy, aroyl, aryloxycarbonyl, aroyloxy, or $R_c$ is aroylamino, alkylthio, arylthio, aryloxycarbonylamino, arylcarbamoyloxy, arylsulfonylamino, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5 alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

each $R_4$ is independently hydrogen, hydroxy or C1–3 alkyl;

$R_5$ is alkyl or acyl each optionally substituted by alkoxy, aryloxy, benzyloxy, hydroxy, carboxy, aryl, benzyl, heterocyclyl chosen from pyrrolidinyl, piperidinyl, morpholinyl, thiomorpholinyl and piperazinyl or amino wherein the N atom is optionally mono-di-substituted by alkyl, aryl or benzyl, or $R_5$ is carboxy;

$R_6$ is hydrogen, hydroxy, nitrile or to a C1–6 saturated or unsaturated branched or unbranched alkyl optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C1–4 alkyl, C3–7 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formulas (Ia) or (Ib) optionally form a 4 to 8 membered mono- or 7–14 membered polycyclo heteroring system, each aromatic or nonaromatic, wherein each ring is optionally substituted by one or more $R_7$;

each $R_7$ and $R_8$ are independently:

hydrogen, C1–5 alkyl chain optionally interrupted by one or two N, O or S(O)$_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated, halogen, hydroxy, oxo, carboxy, nitrile, nitro or NH$_2$C(O)—;

m is 0, 1 or 2;

X is =O, =S or =N—R$_6$ wherein R$_6$ is as defined above, and pharmaceutically acceptable derivatives thereof.

In another embodiment of the invention, there are provided novel compounds of the formula (Ia) and formula (Ib) as described immediately above, and wherein:

$R_1$ and $R_6$ of the formula (Ia) or formula (Ib) form:

a monocyclic 5, 6 or 7 membered aromatic or nonaromatic heterocyclic ring optionally substituted by $R_7$;

a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

or a tricyclic ring wherein the abovementioned bicyclic ring is further fused to a third 5–7 membered aromatic or nonaromatic heterocyclic or carbocyclic ring wherein each ring is optionally independently substituted by one or more $R_7$;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3 alkyl or aryl wherein $R_3$ is optionally substituted by one or more $R_c$;

$R_c$ is C3–7 cycloalkyl, aryl, indanyl, indenyl, bicyclo [2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_7$ and $R_8$ are independently hydrogen, C1–5 alkyl, C3–6 cycloalkyl, aryl, C1–5 alkoxy, aryloxy, benzyloxy each of the aforementioned are optionally halogenated, halogen, hydroxy, oxo, carboxy, nitrite, nitro or NH$_2$C(O)—;

m is 0, 1 or 2 and

X is O or S.

In yet another embodiment of the invention, there are provided novel compounds of the formulas (Ia) and (Ib) as described immediately above, and wherein:

$R_1$ and $R_6$ of the formula (Ia) or Formula (Ib) form:

a monocyclic 5 or 6 membered aromatic or nonaromatic heterocyclic ring optionally substituted by $R_7$;

a bicyclic ring having one 5, 6 or 7 membered aromatic or nonaromatic heterocyclic ring fused to a second 5–6-membered aromatic or nonaromatic heterocyclic or carbocyclic ring wherein each ring is optionally independently substituted by one or more $R_7$;

or a tricyclic ring having one 5, 6 or 7 membered aromatic or nonaromatic heterocyclic ring fused to a 5–6- membered aromatic or nonaromatic carbocyclic ring which in turn is fused to a 5, 6 or 7 membered aromatic or nonaromatic heterocyclic ring;

$R_2$ is hydrogen or methyl;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3, 4tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzithiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono-di-substituted by C1—S alkyl, phenyl or benzyl, or $R_5$ is carboxy;

$R_7$ and $R_8$ are independently hydrogen, C1–4 alkyl, C5–6 cycloalkyl, C1–4 alkoxy, halogen, hydroxy, oxo, carboxy, nitrile, nitro or $NH_2C(O)$—; and X is O.

In yet still another embodiment of the invention, there are provided novel compounds of the formulas (Ia) and (Ib) as described immediately above, and wherein:

$R_1$ and $R_6$ of the formula (Ia) or formula (Ib) form:

a bicyclic ring having one 5 or 6 membered aromatic or nonaromatic heterocyclic ring fused to a second 5–6 membered heteroaryl, heterocycle or phenyl ring; or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring; wherein each ring is optionally independently substituted by one or two $R_7$ $R_2$ is hydrogen;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is C1–5 alkyl or C1–5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono-di-substituted by C1–3 alkyl, phenyl or benzyl, or $R_5$ is carboxy.

In yet a further embodiment of the invention, there are provided novel compounds of die formulas (Ia) and (Ib) as described immediately above, and wherein:

$R_1$ and $R_6$ of the formula (Ia) or Formula (Ib) form:

a bicyclic ring having one 5–6 membered aromatic or nonaromatic heterocyclic ring fused to a phenyl or 5–6 membered aromatic or nonaromatic heterocyclic ring;

a tricyclic ring having one 5–6 membered aromatic or nonaromatic heterocyclic ring fused to a 6-membered aromatic or nonaromatic carbocyclic ring which in turn is fused to a 5–6 membered aromatic or nonaromatic heterocyclic ring;

wherein each ring is optionally independently substituted by one or two $R_7$ $R_3$ is a bond, C1–10 alkyl wherein one or more carbon atoms are optionally replaced by O, S or N, or $R_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

and $R_5$ is C1–3 alkyl or C1–3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or $R_5$ is carboxy.

In yet still a further embodiment of the invention, there are provided novel compounds of the formula (Ia) or formula (Ib) as described immediately above, and wherein:

$R_1$ and $R_6$ of the formula (Ia) form:
the bicyclic ring:

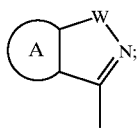

wherein W is —S(O)$_n$—, >C(O), —O—C(O)—, —S—C(O)— or —NH—C(O)—, n is 0, 1 or 2, fused ring A is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$.

or the tricyclic ring:

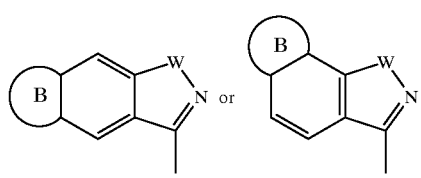

wherein W is —S(O)$_n$—, >C(O), —O—C(O)—, —S—C(O)— or —NH—C(O)—, n is 0, 1 or 2, fused ring B is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$ $R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC 1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, spiro[3.5]nonyl, spiro[4.5]decanyl, cubanyl, 1,2,3,4-tetrahydronaphthyl, phenoxy, benzoyl, phenoxycarbonyl, benzoyloxy, phenylthio, fluoro or chloro.

In a further embodiment of the invention, there are provided novel compounds of the formulas (Ia) and (Ib) as described immediately above, and wherein:

$R_1$ and $R_6$ of the formula (Ia) form the bicyclic ring selected from:

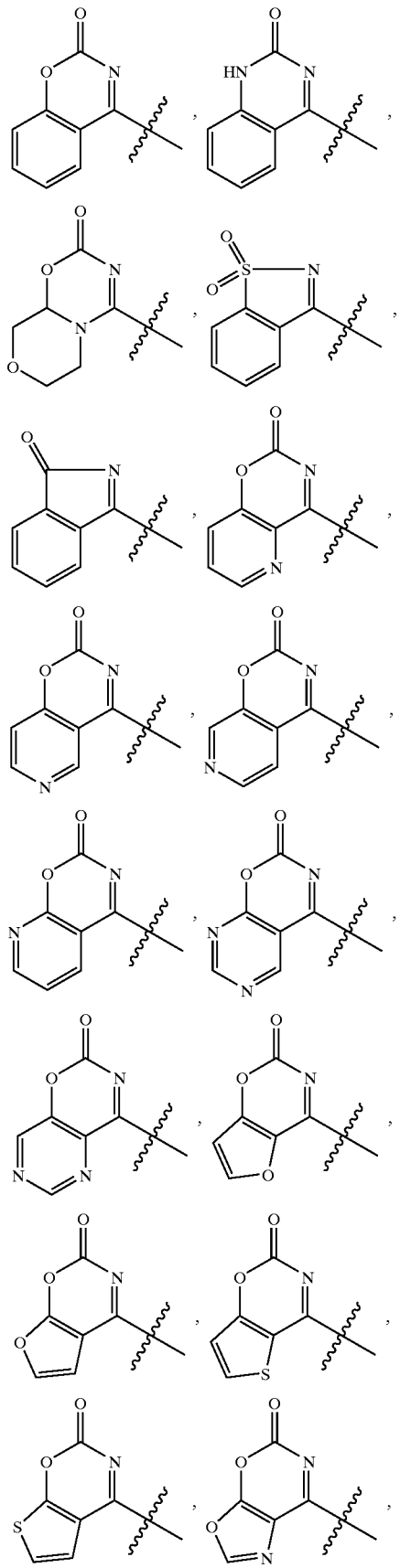

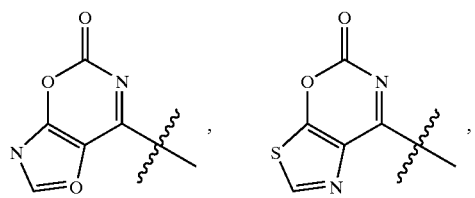

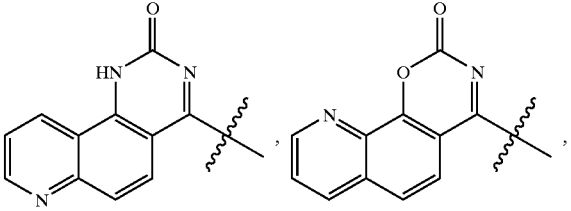

or R₁ and R₆ of the formula (Ia) form the tricyclic ring selected from:

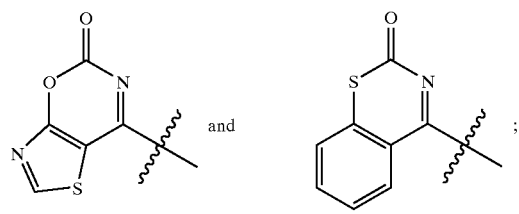

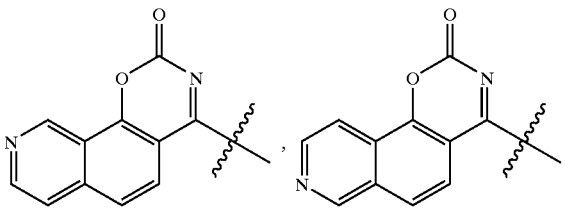

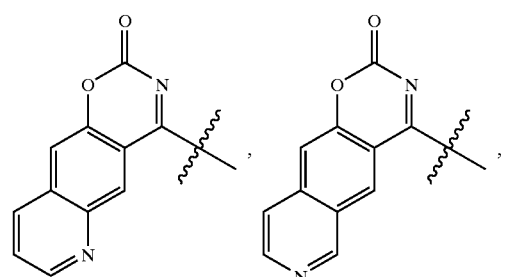

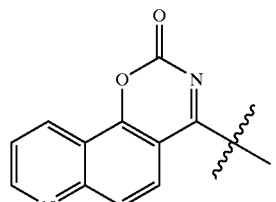

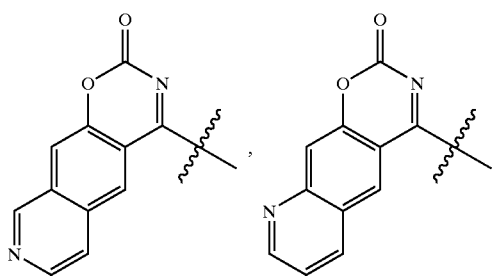

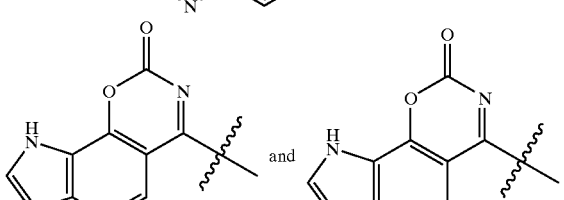

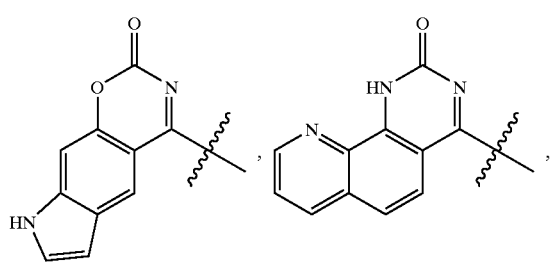

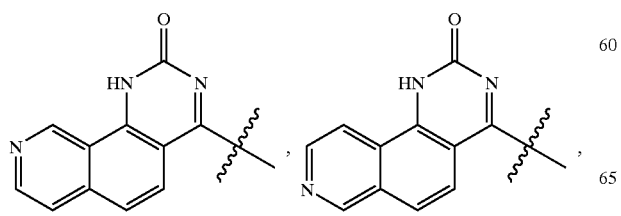

wherein each ring is optionally independently substituted by one or two $R_7$;

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfiniylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4-tetrahydronaphthyl, spiro[2.5]octanyl, spiro[3.5] nonyl, spiro[4.5] decanyl, fluoro or chloro.

In another embodiment of the invention, there are provided novel compounds of the formulas (Ia) and (Ib) as described for the broadest generic aspect above and wherein: $R_1$ and $R_6$ remain acyclic:

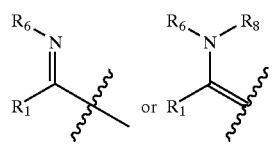

R₁ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein R₁ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

R₂ is hydrogen or methyl or ethyl;

R₃ is a bond, hydrogen, C1–10 alkyl wherein one or more carbon atoms are optionally replaced by O, S or N, or R₃ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein R₃ is optionally substituted by one or more $R_c$;

$R_c$ is C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more Rd;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

R₄ is hydrogen or methyl;

R₆ is hydroxy, nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with 1–2 oxo groups, —NH₂, one or more C1–4 alkyl, C3–6 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

R₈ is hydrogen, C1–5 alkyl, C3–6 cycloalkyl, aryl, C1–5 alkoxy, aryloxy, benzyloxy each of the aforementioned are optionally halogenated or hydroxy; and X is O.

In another embodiment of the invention, there are provided novel compounds of the formula (Ia) and (Ib) as described immediately above, and wherein:

R₁ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein R₁ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

R$_b$ is methyl, cyclopropyl, phenyl, methoxy, phenoxy, benzyloxy, fluoro, chloro, hydroxy, oxo, carboxy or carboxamide;

R$_3$ is a bond, hydrogen, C1–10 alkyl wherein one or more carbon atoms are optionally replaced by O, S or N, or R$_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein R$_3$ is optionally substituted by one or more R$_c$;

R$_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or R$_c$ is halogen, hydroxy, oxo, carboxy, cyano, nitro, amidino or guanidino, R$_x$ may be further optionally substituted by one or more R$_d$;

R$_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

R$_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono- di-substituted by C1–5 alkyl, phenyl or benzyl, or R$_5$ is carboxy;

R$_5$ is nitrile or a C1–5 saturated or unsaturated branched or unbranched alkyl optionally partially or fully halogenated wherein one or more C atoms are optionally replaced by O, NH, or S(O)$_2$ and wherein said chain is optionally independently substituted with oxo, —NH$_2$, C3–6 cycloalkyl, piperidinyl, morpholinyl, thiomorpholinyl, piperazinyl, pyridinyl, pyrimidinyl or pyrazinyl; and R$_8$ is hydrogen, C1–3 alkyl, C3–6 cycloalkyl, phenyl, C1–3 alkoxy, benzyloxy each of the aforementioned are optionally halogenated or hydroxy.

In yet another embodiment of the invention, there are provided novel compounds of the formula (Ia) or formula (Ib) as described immediately above, and wherein:

R$_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein R$_1$ is optionally substituted by one or more R$_a$;

R$_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or R$_a$ is acetylamino, methylthio, phenylthio wherein the sulfur atom may be oxidized to a sulfoxide or sulfone, ureido wherein either nitrogen atom may be independently substituted by methyl or phenyl, or R$_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or R$_a$ is fluoro, chloro, hydroxy, oxo, carboxy, cyano or carboxamide;

R$_3$ is a bond, C1–10 alkyl wherein one or more carbon atoms are optionally replaced by O, S or N, or R$_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein R$_3$ is optionally substituted by one or more R$_c$;

R$_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or R$_c$ is halogen, hydroxy, oxo, carboxy or cyano, R$_c$ may be further optionally substituted by one or more R$_d$;

R$_d$ is methyl, cyclopropyl, cyclohexyl, phenyl, benzyl, methoxy, phenoxy, benzyloxy, benzoyl, fluoro, chloro, oxo or cyano;

R$_5$ is C1–5 alkyl or C1–5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono- di-substituted by C1–3 alkyl, phenyl or benzyl, or R$_5$ is carboxy;

R$_6$ is nitrile or a C1–5 saturated or unsaturated branched or unbranched alkyl optionally partially or fully halogenated wherein one or more C atoms are optionally replaced by O, NH, or S(O)$_2$ and wherein said chain is optionally independently substituted with oxo, —NH$_2$, C3–6 cycloalkyl, morpholinyl or piperazinyl; and R is hydrogen, C1–3 alkyl, C1–3 alkoxy or hydroxy.

In yet still another embodiment of the invention, there are provided novel compounds of the formulas (Ia) and (Ib) as described immediately above, and wherein:

R$_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

R$_3$ is a bond, C1–10 alkyl wherein one or more carbon atoms are optionally replaced by O, S or N, or R$_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is C1–3 alkyl or C1–3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or $R_5$ is carboxy;

$R_6$ is C3–6 cycloalkyloxycarbonyl, acetyl, C1–3alkylaminocarbonyl or C1–3alkoxycarbonyl; and $R_8$ is hydrogen, C1–3 alkyl or C1–3 alkoxy.

In yet a further embodiment of the invention, there are provided novel compounds of the formulas (Ia) and (Ib) as described immediately above, and wherein:

$R_1$ is morpholin-4-yl, p-fluorophenyl or p-methoxyphenyl;

$R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5] octanyl, spiro[3.5] nonyl, spiro[4.5] decanyl, cubanyl, 1,2,3,4-tetrahydronaphthyl, phenoxy, benzoyl, phenoxycarbonyl, benzoyloxy, phenylthio, fluoro or chloro;

$R_6$ is C3–6 cycloalkyloxycarbonyl, acetyl, ethylaminocarbonyl or ethoxycarbonyl; and $R_8$ is hydrogen.

In a further embodiment of the invention, there are provided novel compounds of the formulas (Ia) and (Ib) as described immediately above, and wherein:

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–-3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4tetrahydronaphthyl, spiro[2.5] octanyl, spiro[3.5] nonyl, spiro[4.5] decanyl, fluoro or chloro.

Further compounds of Formula (Ia), made up of components A, B and C are provided in Table I below. Any and all combinations of A, B, and C components within the structural limitations of Formula (Ia), comprise a compound of the invention, and their pharmaceutically acceptable derivatives. For example, the compound:

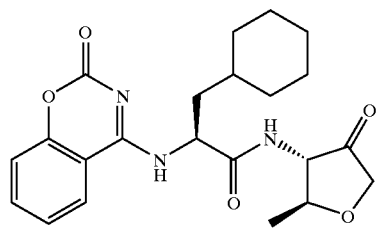

would represent the combination of A1, B1, C2.

These compounds can be synthesized by the General schemes, methods described in the experimental section of this document and analogous methods known to those skilled in the art without undue experimentation. Preferred compounds will possess desirable inhibition activity of Cathepsin S in a cell based assay as described in Riese, R. J. et al., Immunity, 1996, 4, 357–366, incorporated herein by reference.

FORMULA (Ia)

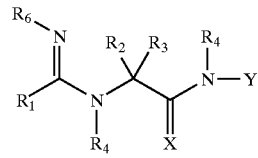
(Ia)

wherein for the Formula (Ia), the components

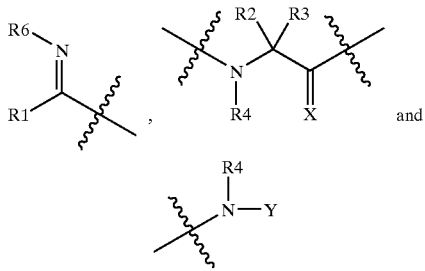

are chosen from any combination of A, B and C as follows:

TABLE I
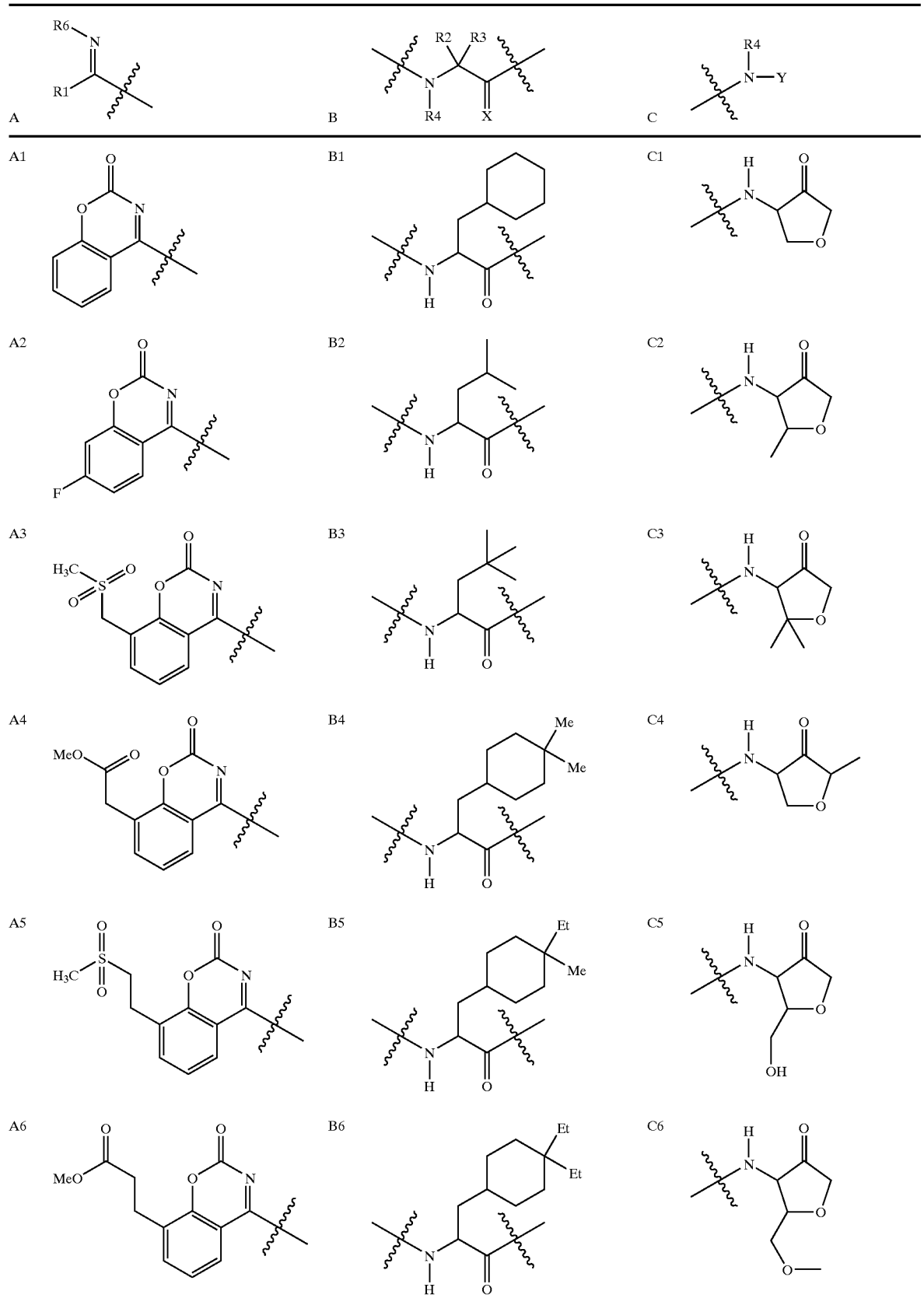

TABLE I-continued
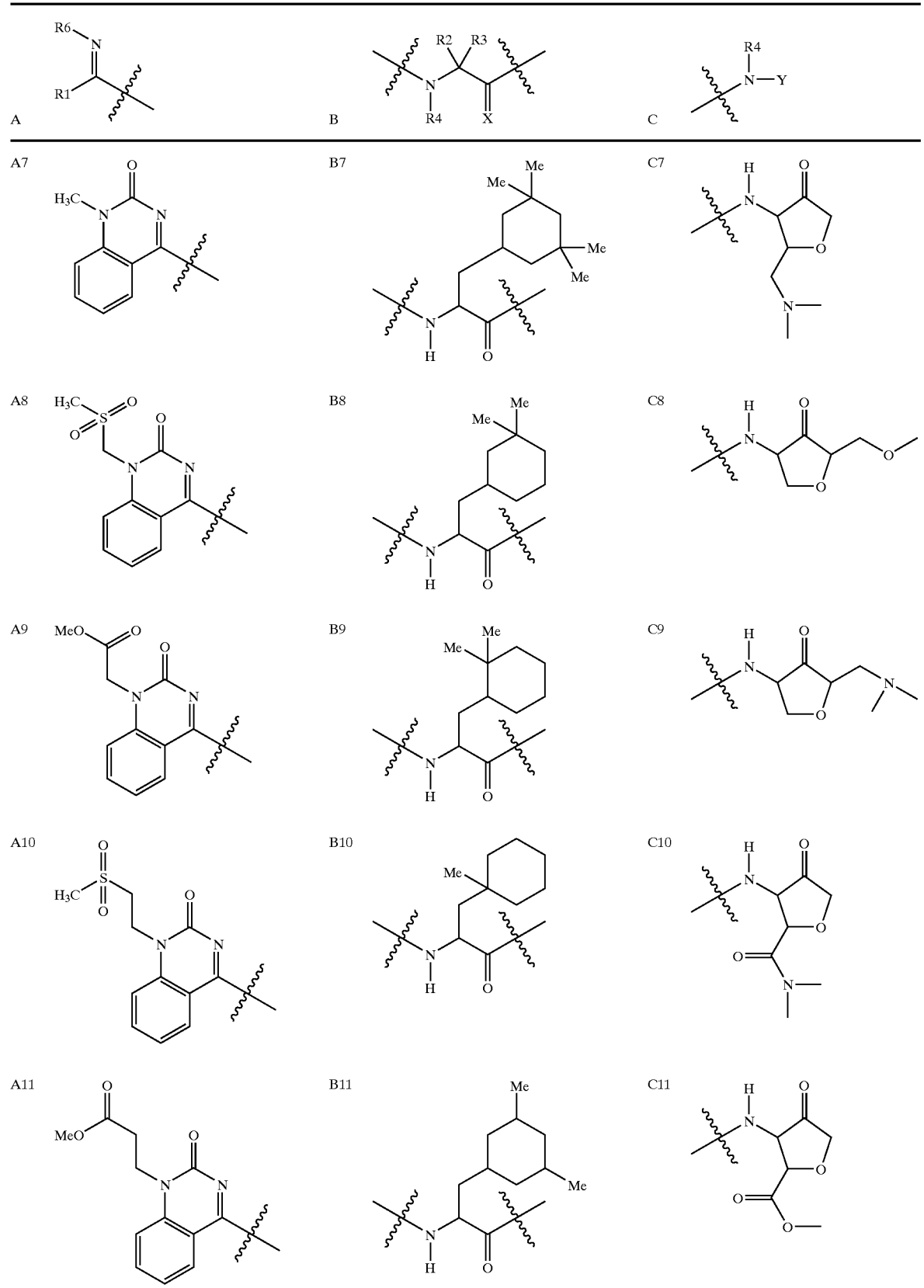

TABLE I-continued
| A | B | C |
|---|---|---|
| A12 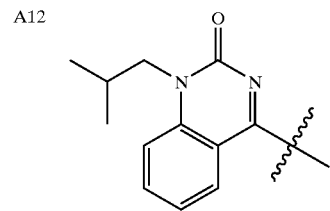 | B12 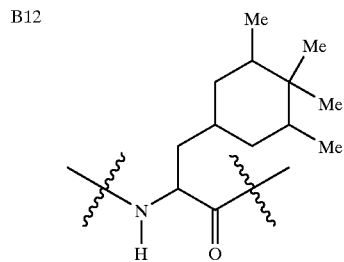 | C12 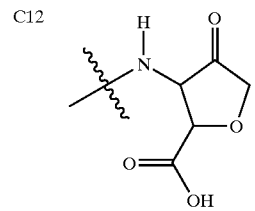 |
| A13 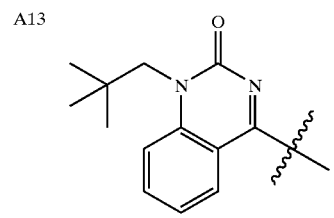 | B13 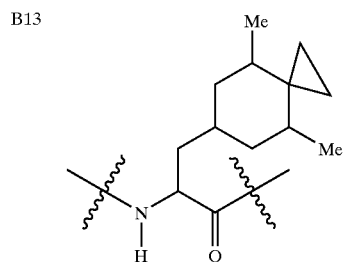 | C13 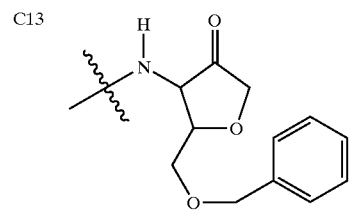 |
| A14 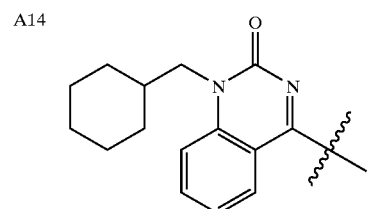 | B14 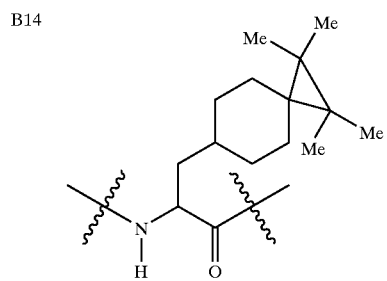 | C14 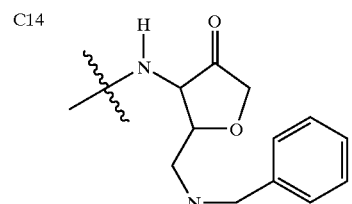 |
| A15 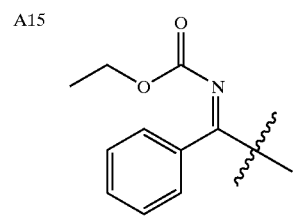 | B15 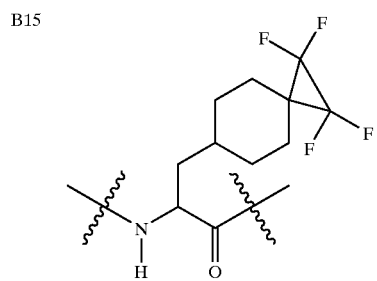 | C15 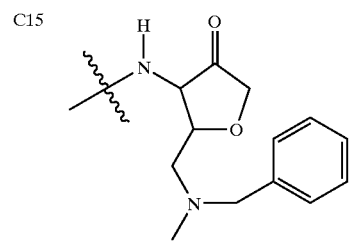 |
| A16 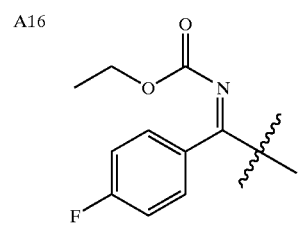 | B16 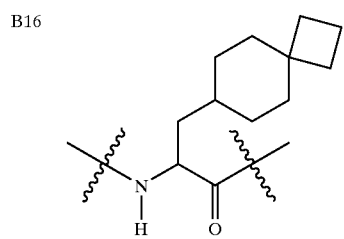 | C16 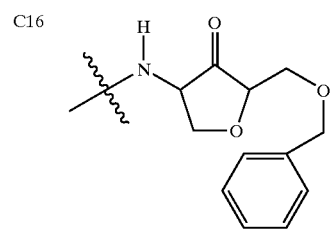 |

TABLE I-continued
| A | B | C |
|---|---|---|
| 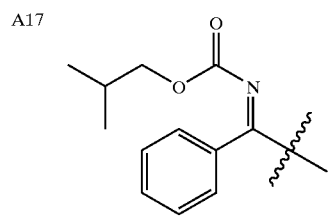 | 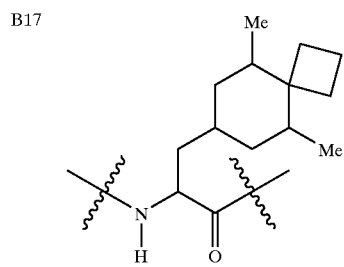 | 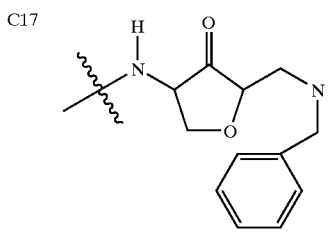 |
| A17 | B17 | C17 |
| 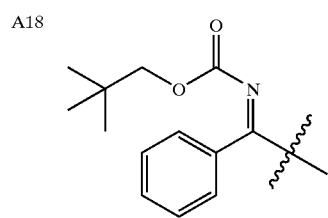 | 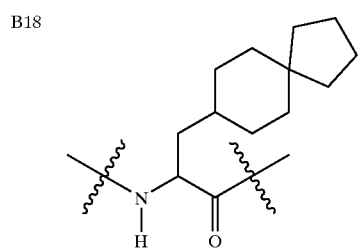 | 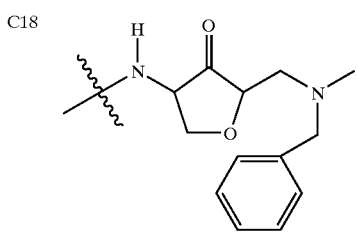 |
| A18 | B18 | C18 |
| 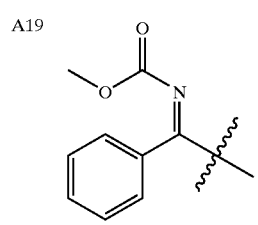 | 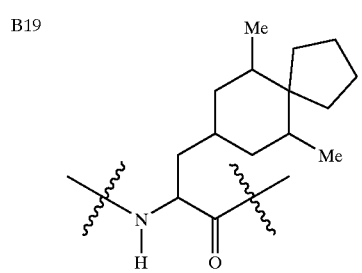 | 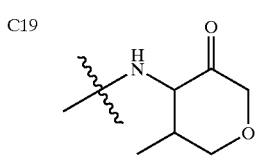 |
| A19 | B19 | C19 |
| 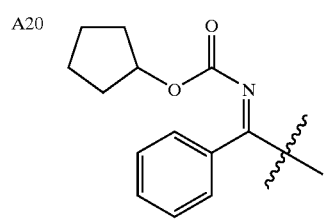 | 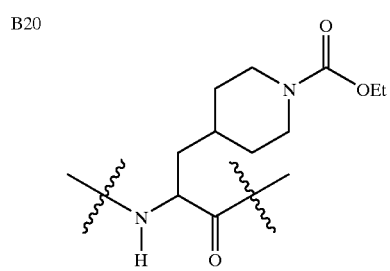 | 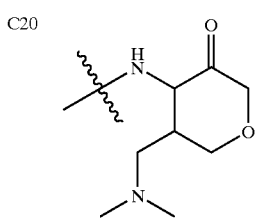 |
| A20 | B20 | C20 |
| 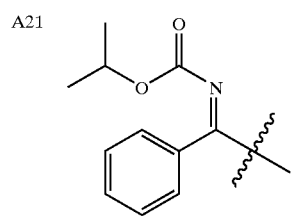 | 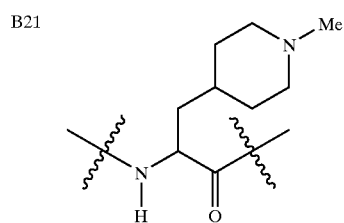 | 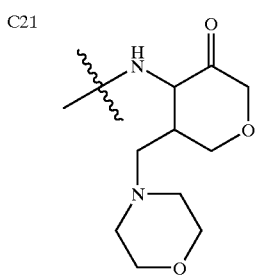 |
| A21 | B21 | C21 |

TABLE I-continued
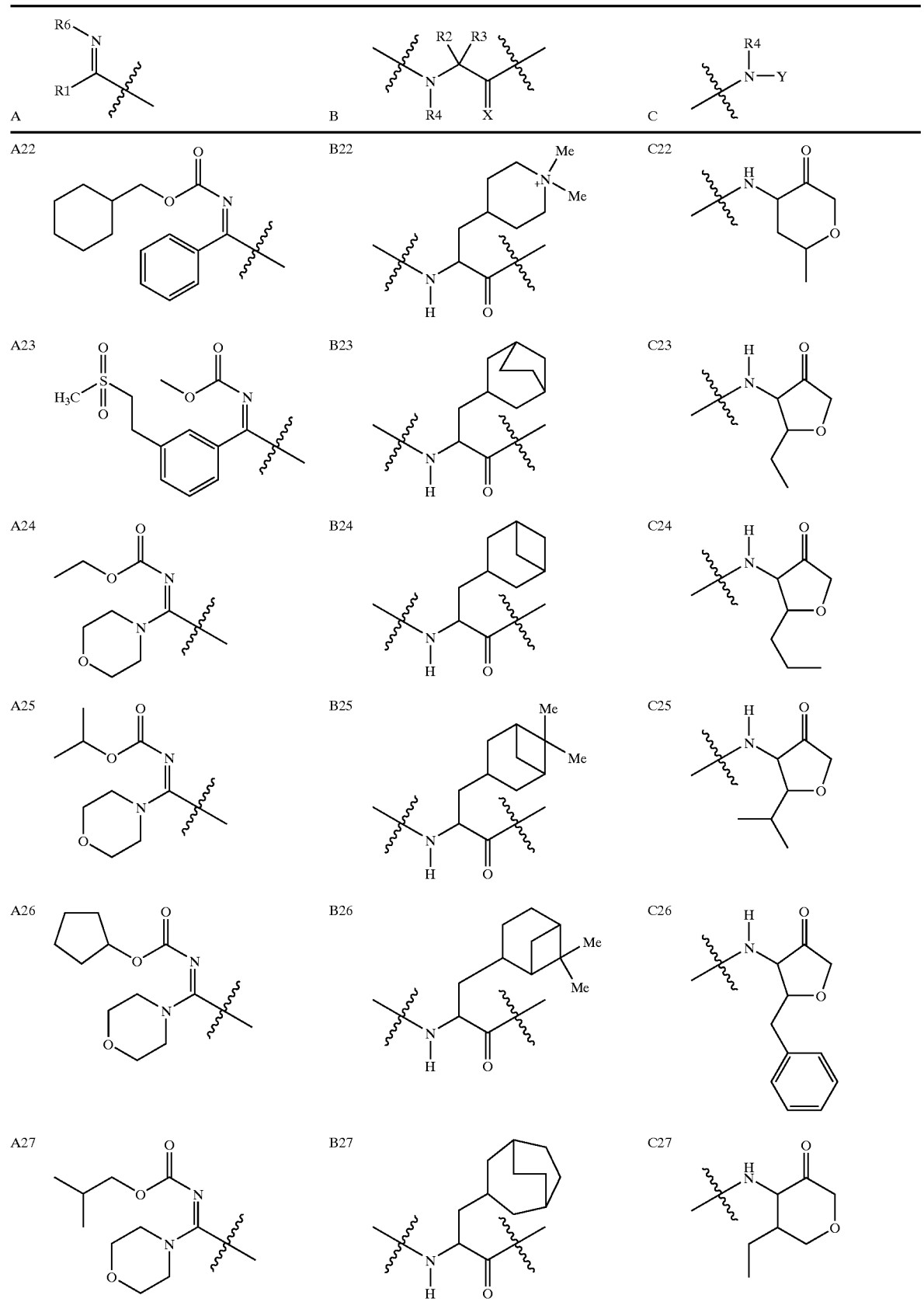

TABLE I-continued
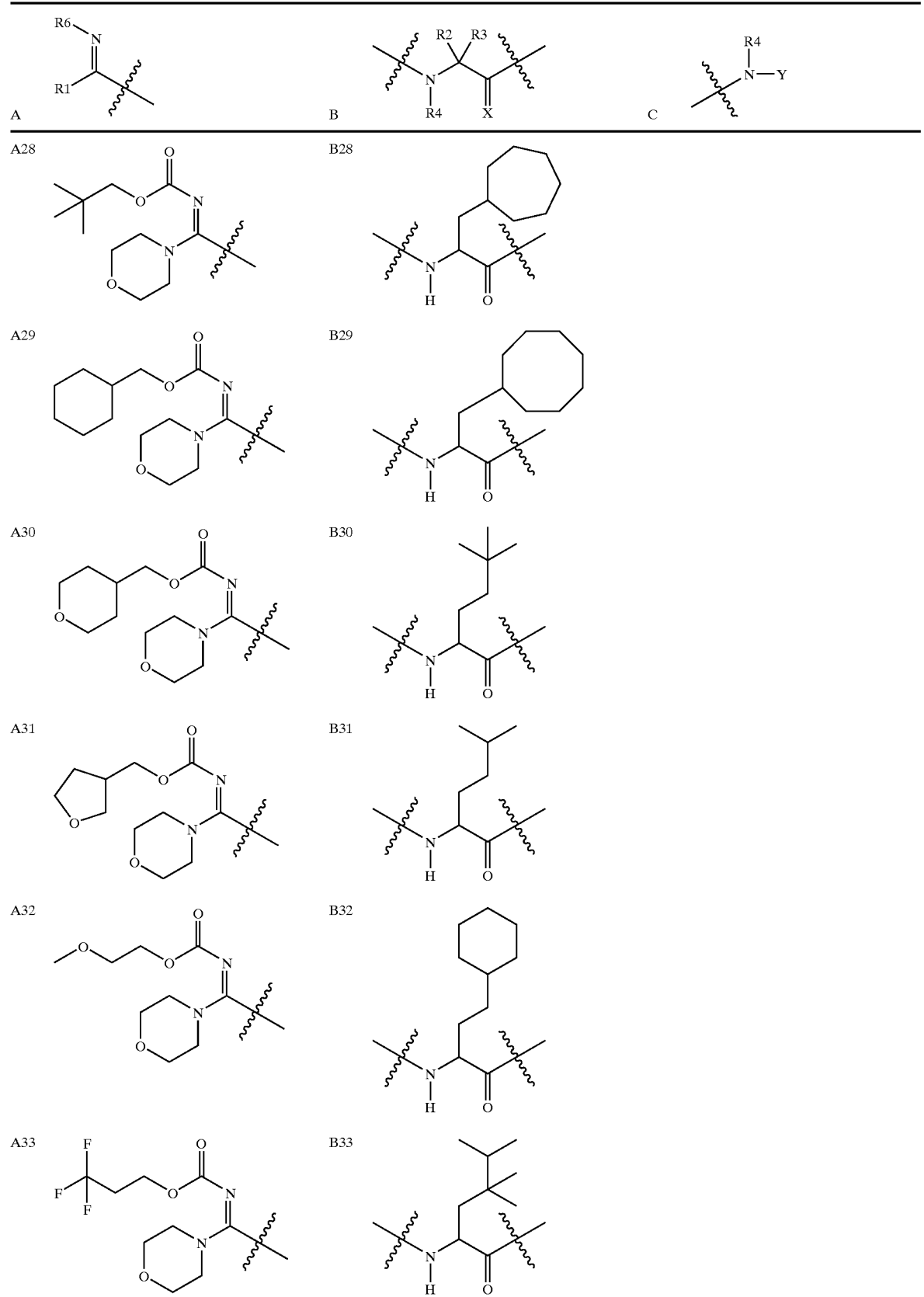

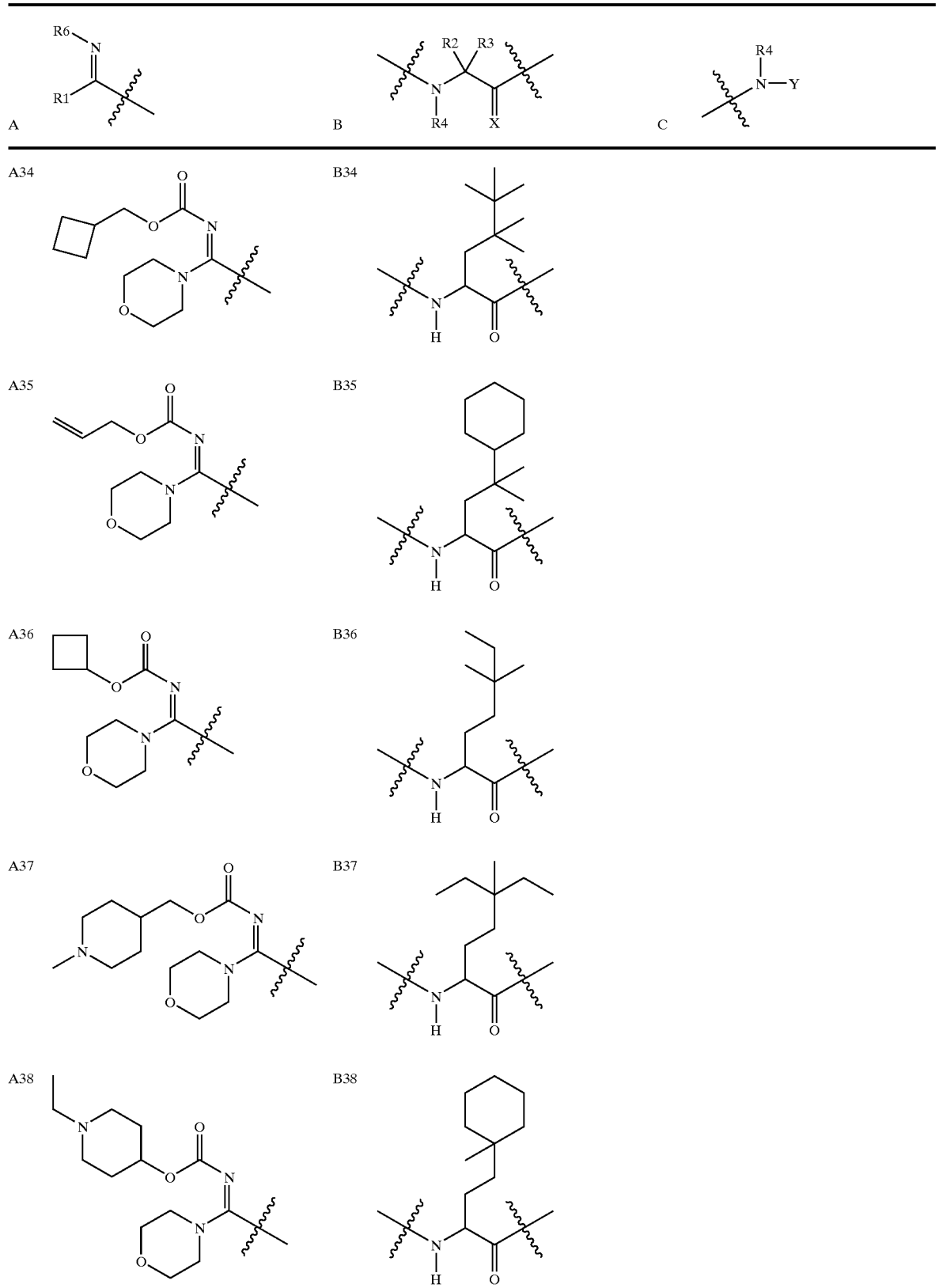

TABLE I-continued
| A | B | C |
|---|---|---|
| A39 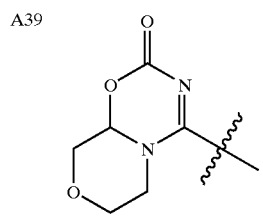 | B39 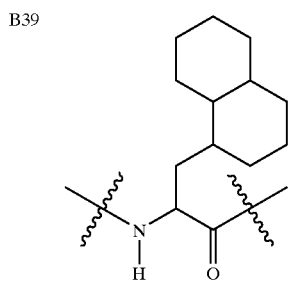 | |
| A40 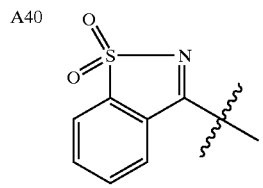 | B40 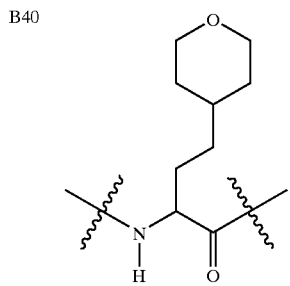 | |
| A41 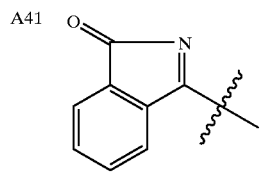 | B41 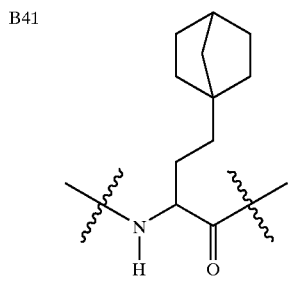 | |
| A42 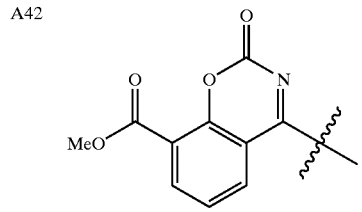 | B42 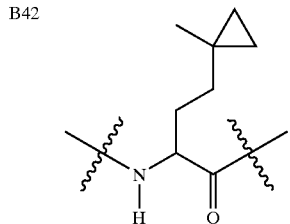 | |
| A43 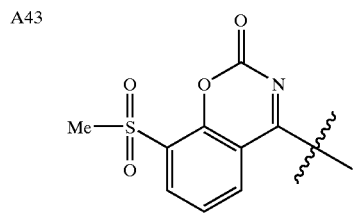 | B43 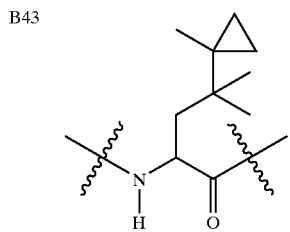 | |

TABLE I-continued
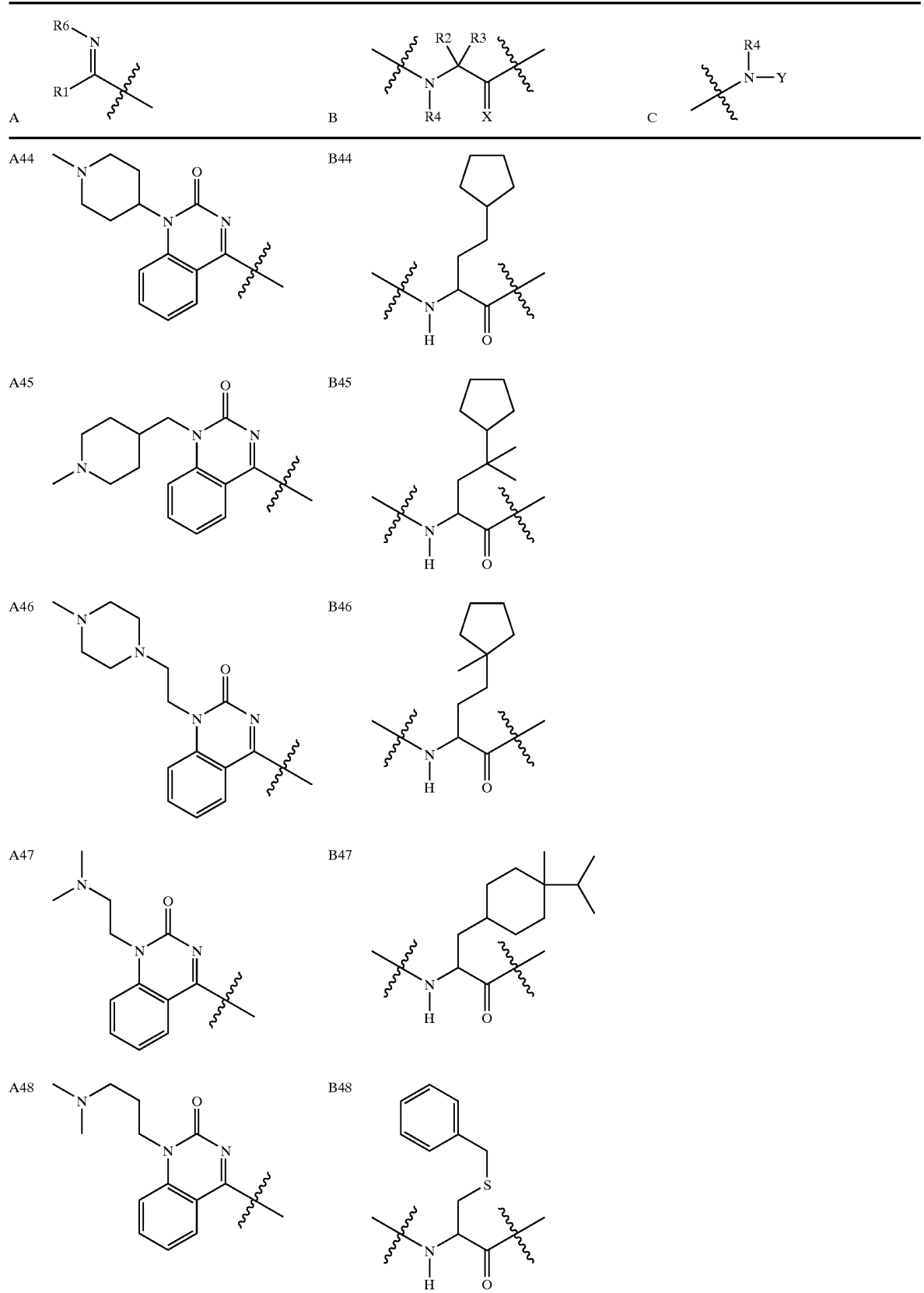

TABLE I-continued

| A | B | C |
|---|---|---|

A49, B49

A50, B50

A51, B51

A52, B52

A53, B53

TABLE I-continued
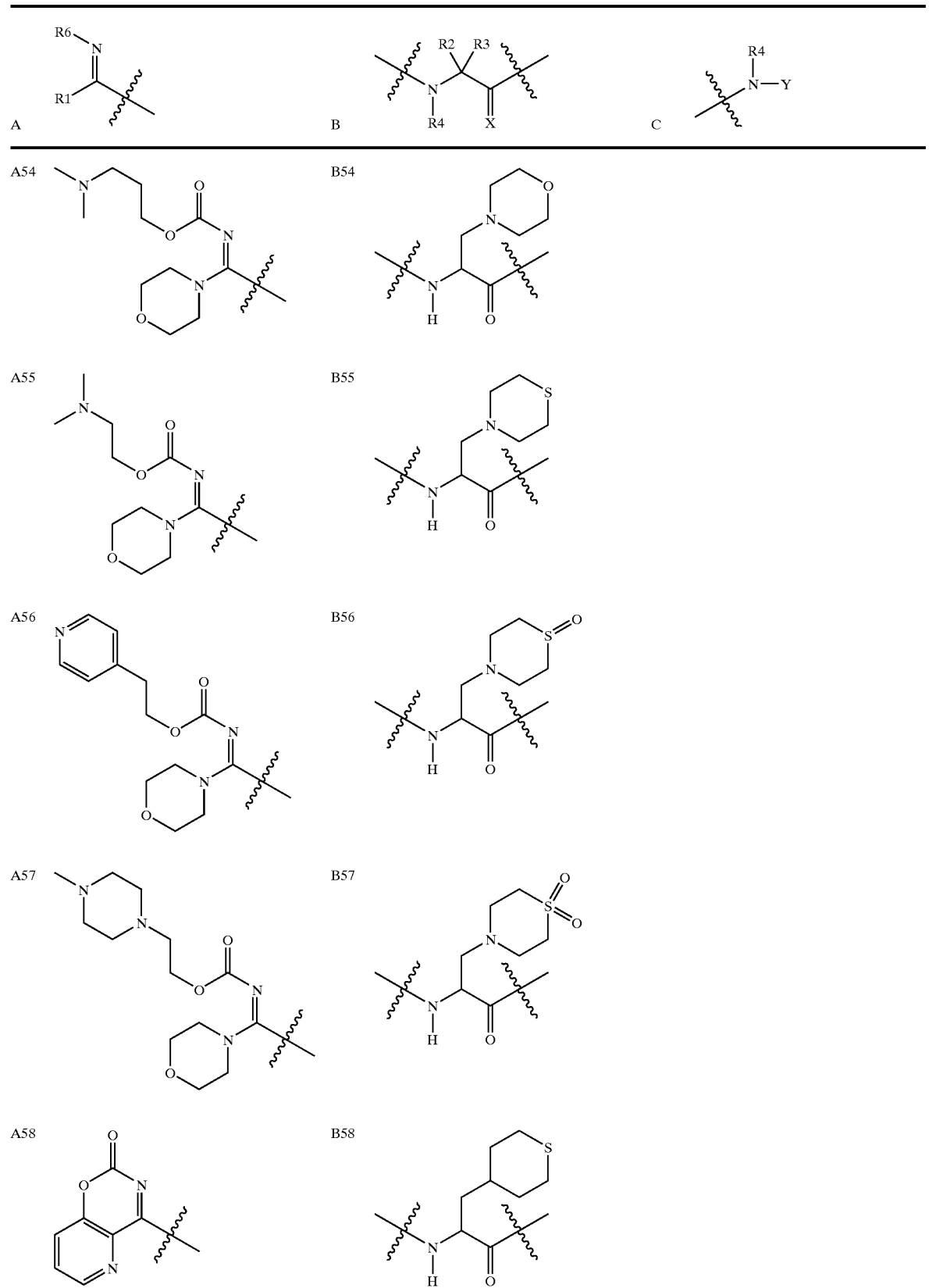

TABLE I-continued
| A | | B | | C | |
|---|---|---|---|---|---|
| A59 | 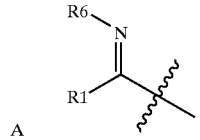 | B59 | 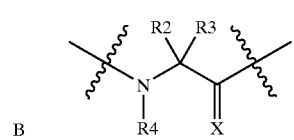 | | |
| A60 | 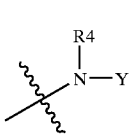 | B60 | 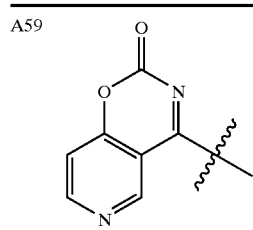 | | |
| A61 | 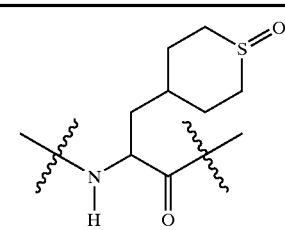 | B61 | 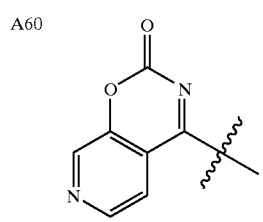 | | |
| A62 | 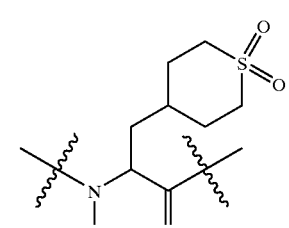 | B62 | 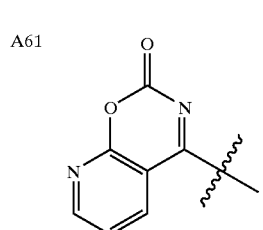 | | |
| A63 | 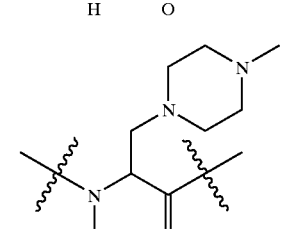 | B63 | 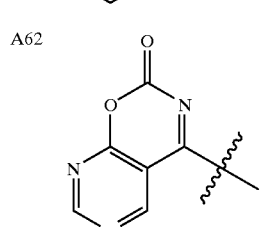 | | |
| A64 | 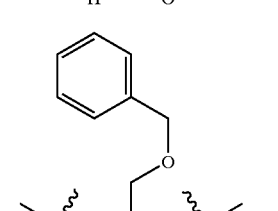 | B64 | 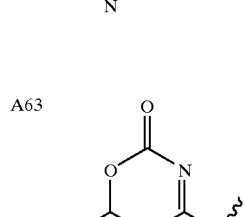 | | |

TABLE I-continued
| A | B | C |
|---|---|---|
| A65 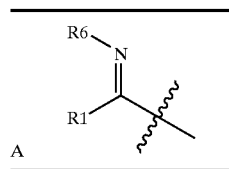 | B65 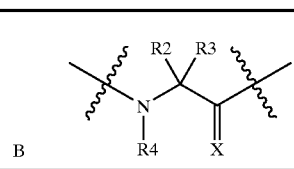 | |
| A66 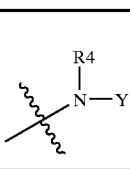 | B66 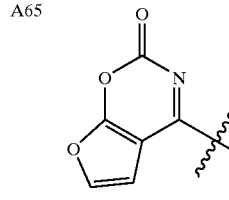 | |
| A67 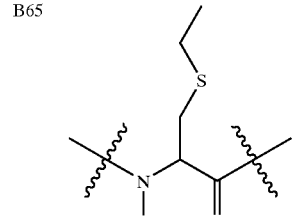 | B67 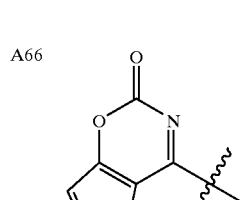 | |
| A68 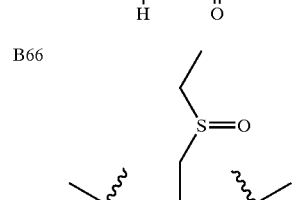 | B68 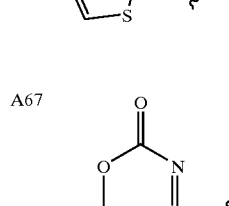 | |
| A69 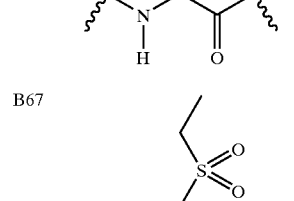 | B69 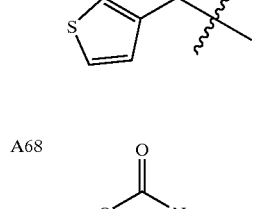 | |
| A70 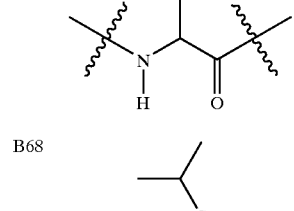 | B70 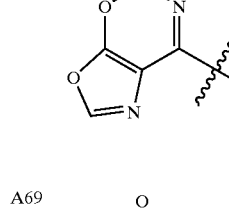 | |

TABLE I-continued
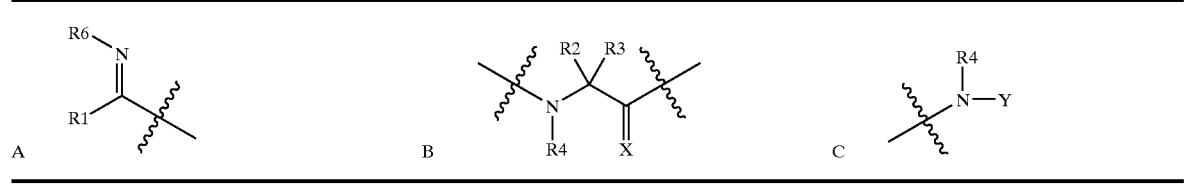
| A | B | C |
|---|---|---|
| A71 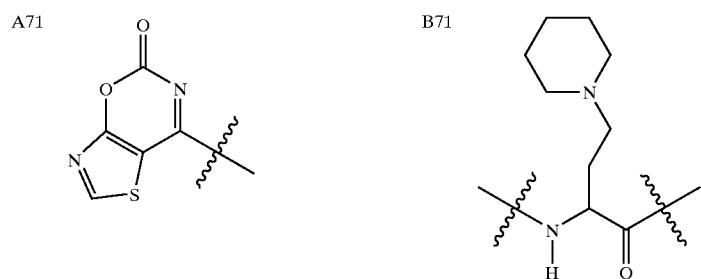 | B71 | |
| A72 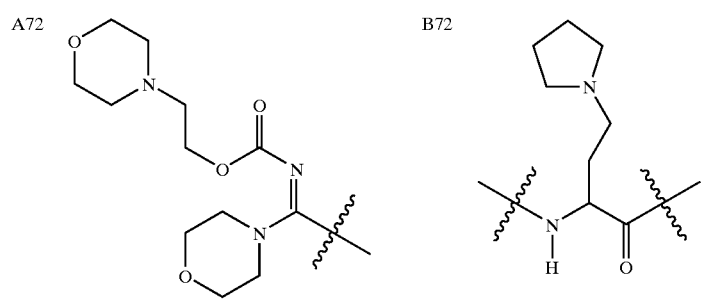 | B72 | |
| A73 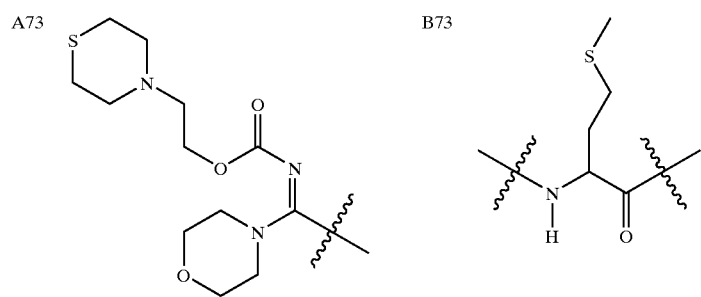 | B73 | |
| A74 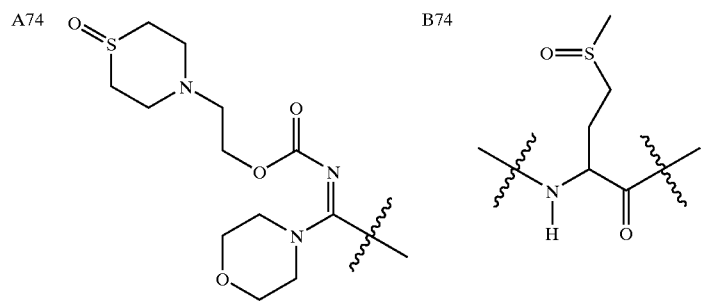 | B74 | |

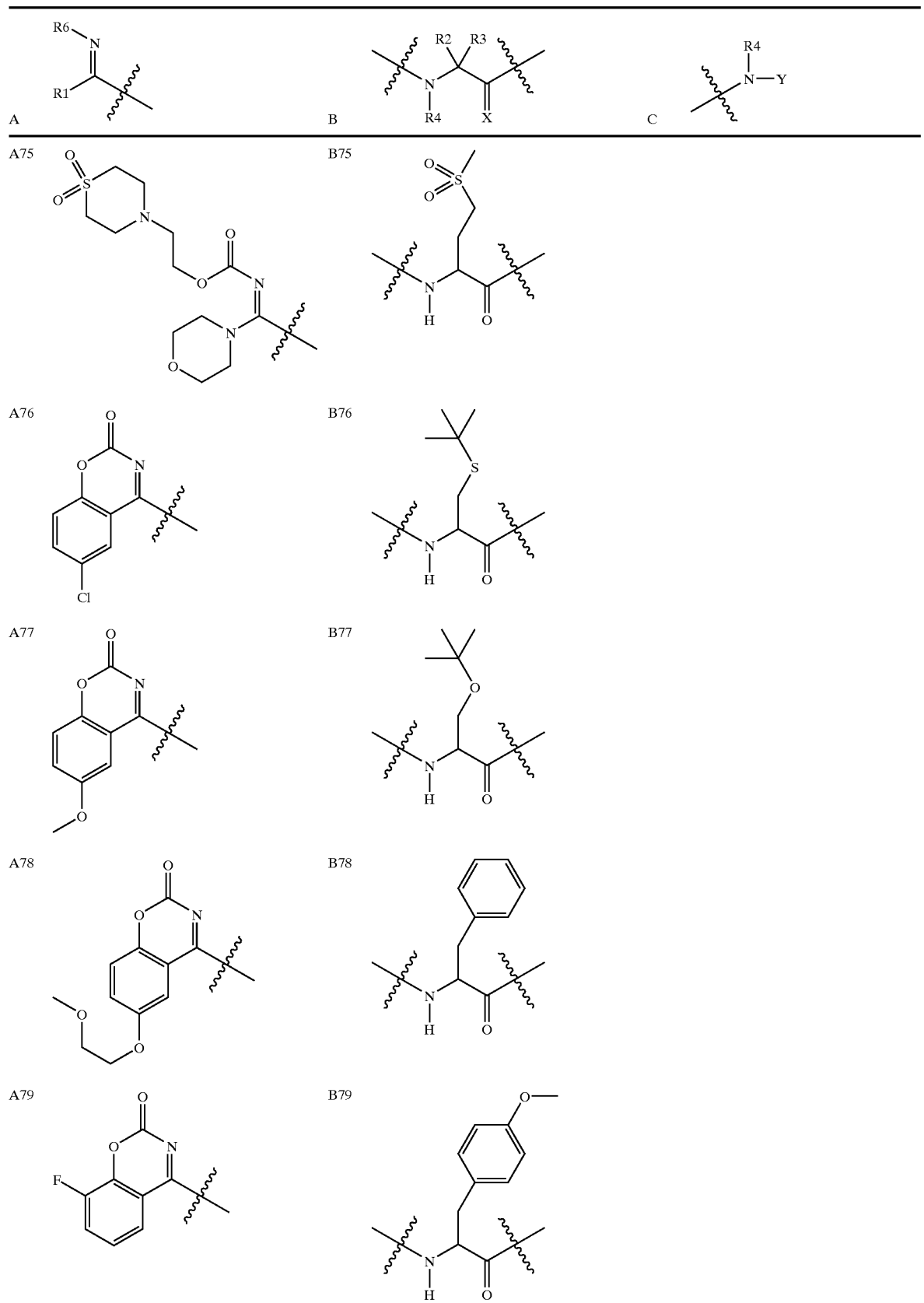

TABLE I-continued
| A | B | C |
|---|---|---|
| 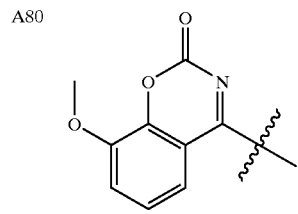 | 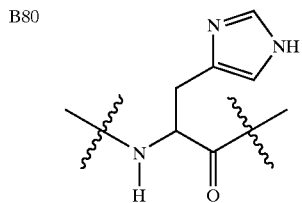 | |
| A80 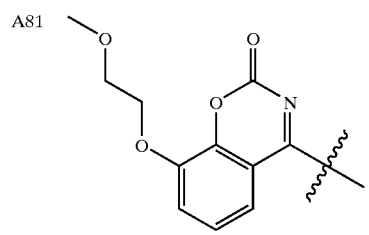 | B80 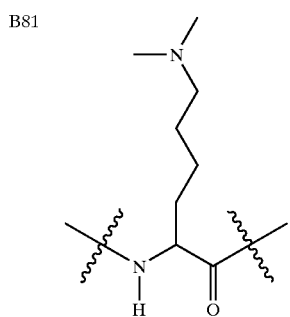 | |
| A81 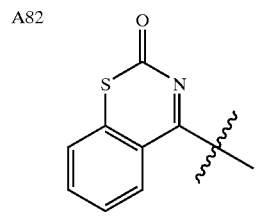 | B81 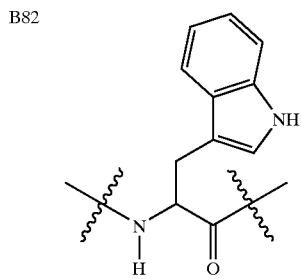 | |
| A82 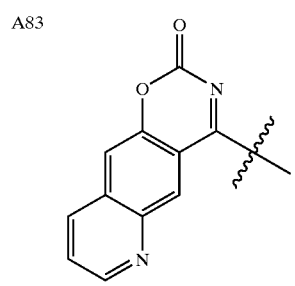 | B82 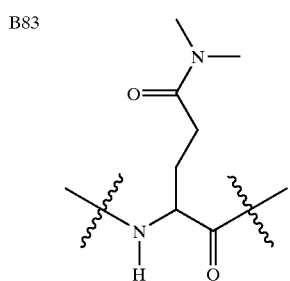 | |
| A83 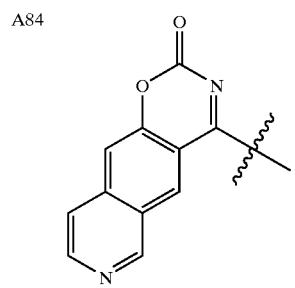 | B83 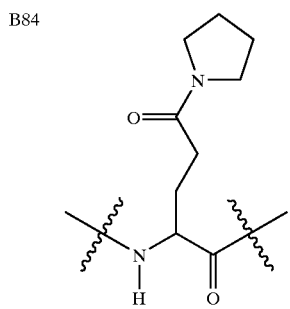 | |
| A84 | B84 | |

TABLE I-continued

TABLE I-continued
| A | B | C |
|---|---|---|
| A90 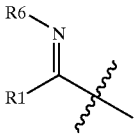 | B90 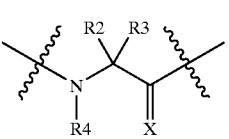 | |
| A91 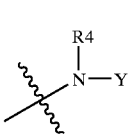 | B91 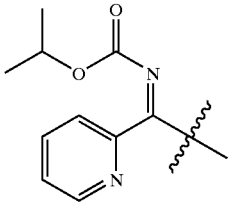 | |
| A92 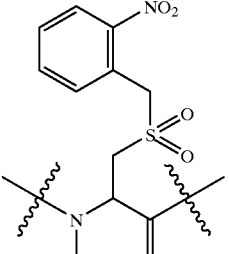 | B92 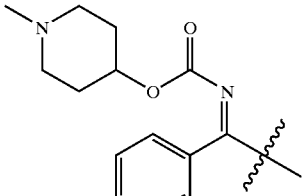 | |
| A93 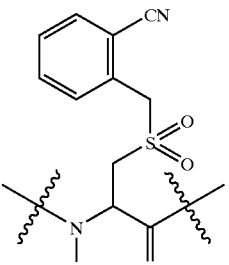 | B93 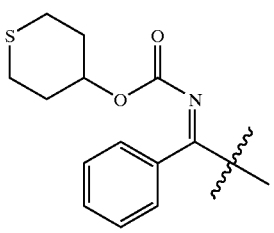 | |
| A94 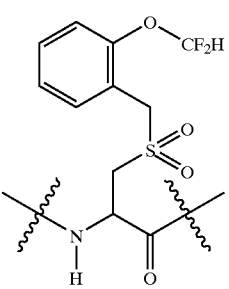 | B94 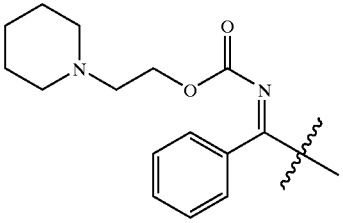 | |

TABLE I-continued
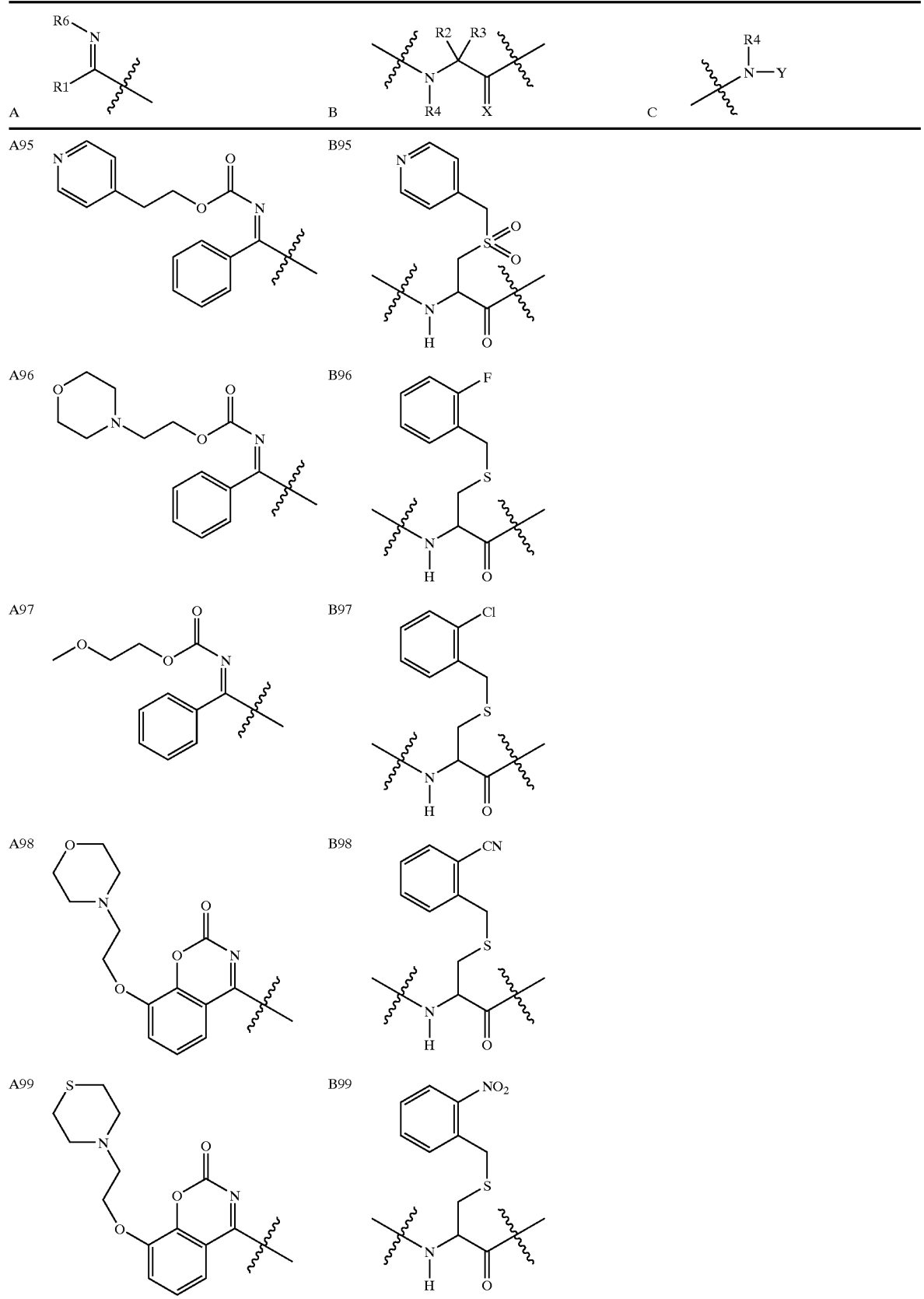

TABLE I-continued
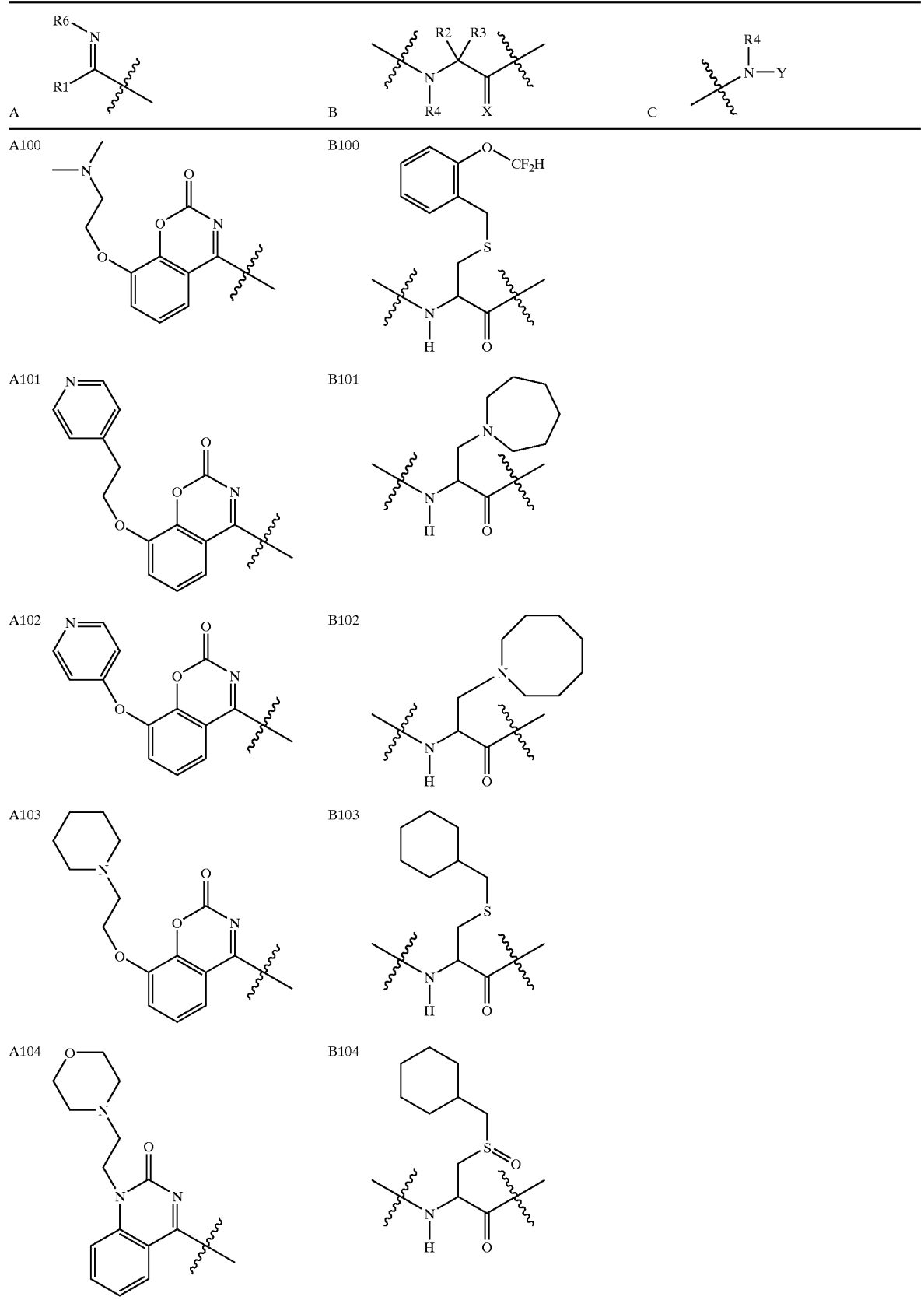

TABLE I-continued

| A | B | C |
|---|---|---|
| A105 | B105 | |
| A106 | B106 | |
| A107 | B107 | |
| A108 | B108 | |
| A109 | B109 | |

TABLE I-continued
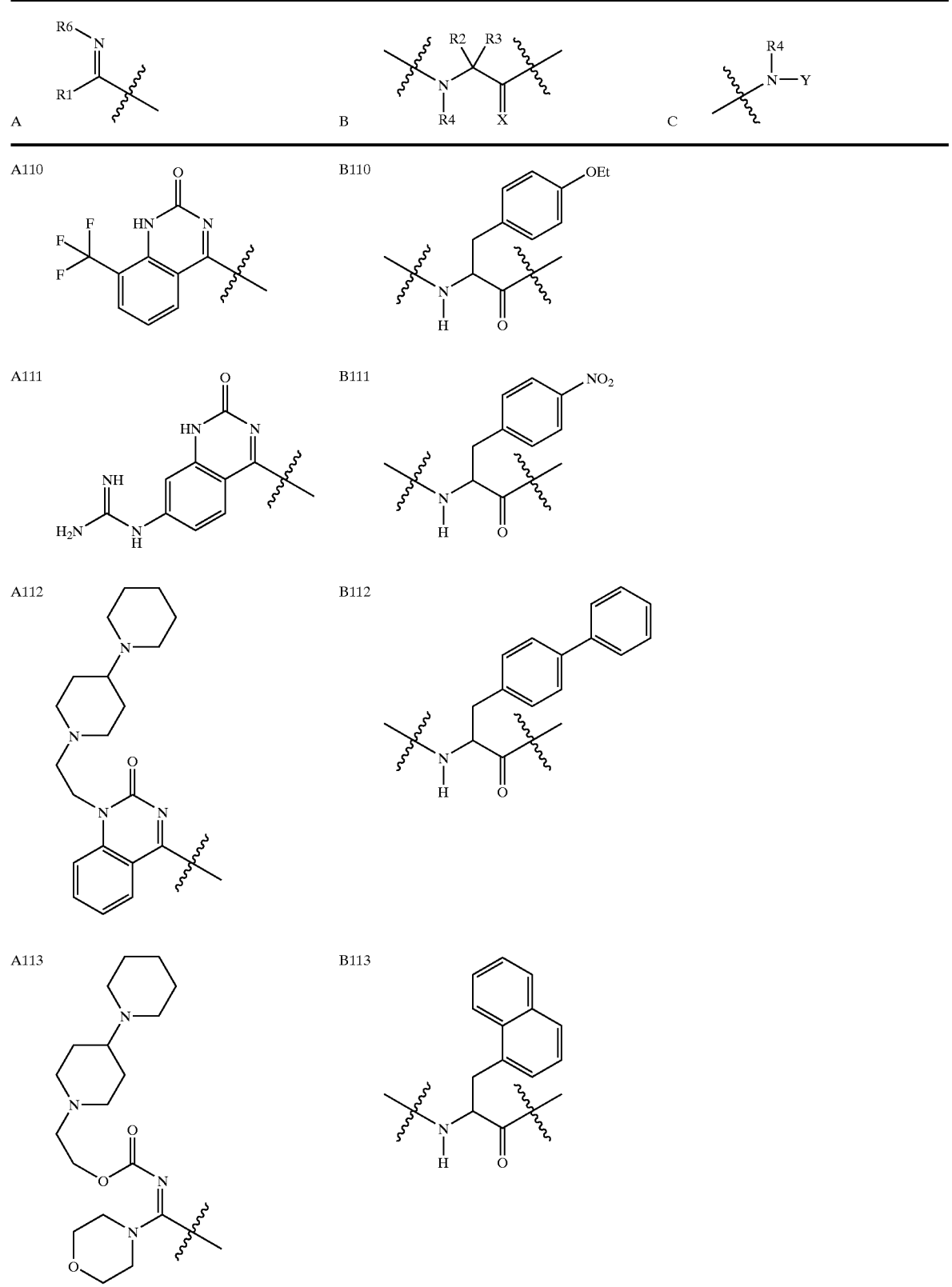

TABLE I-continued
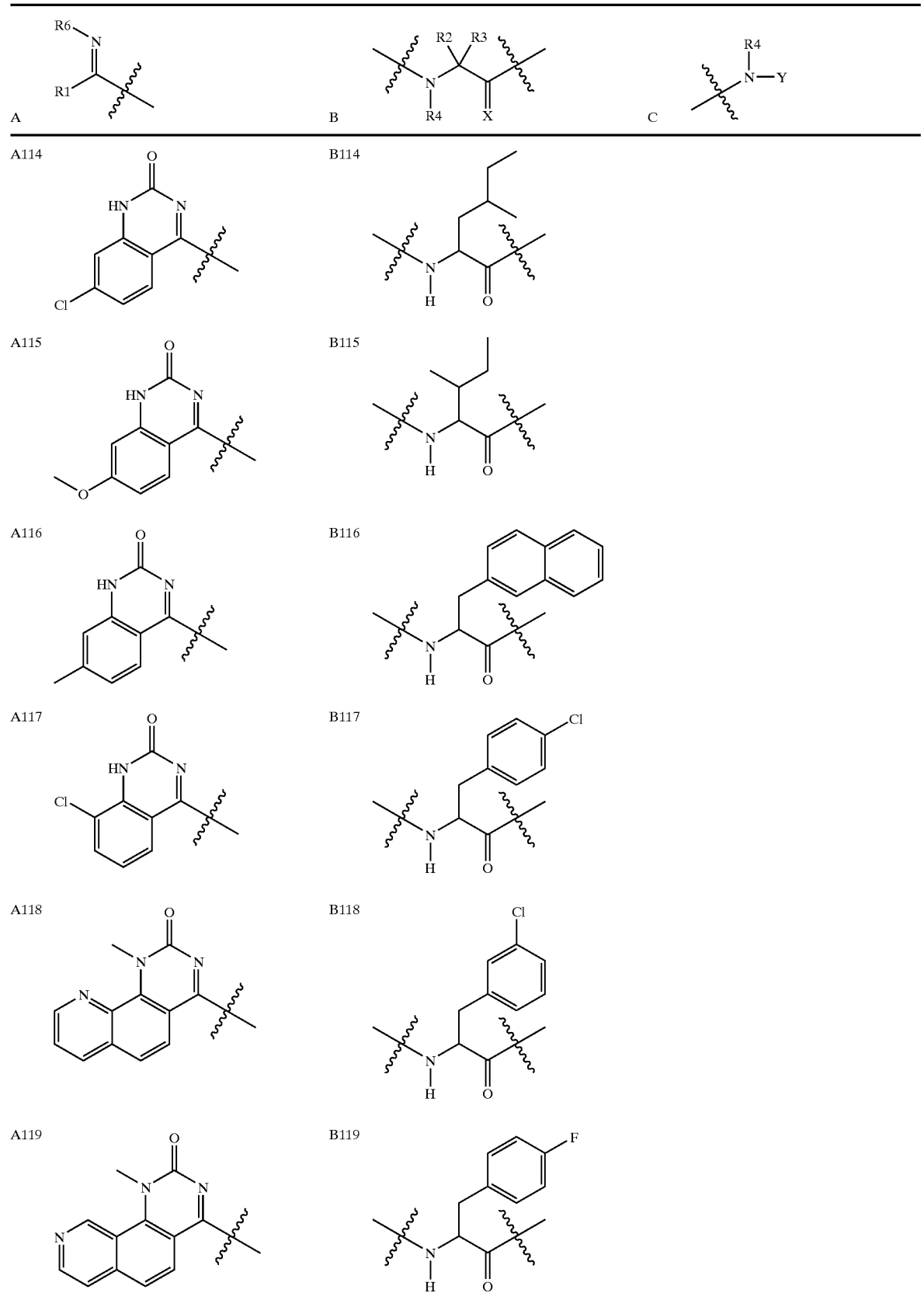

TABLE I-continued
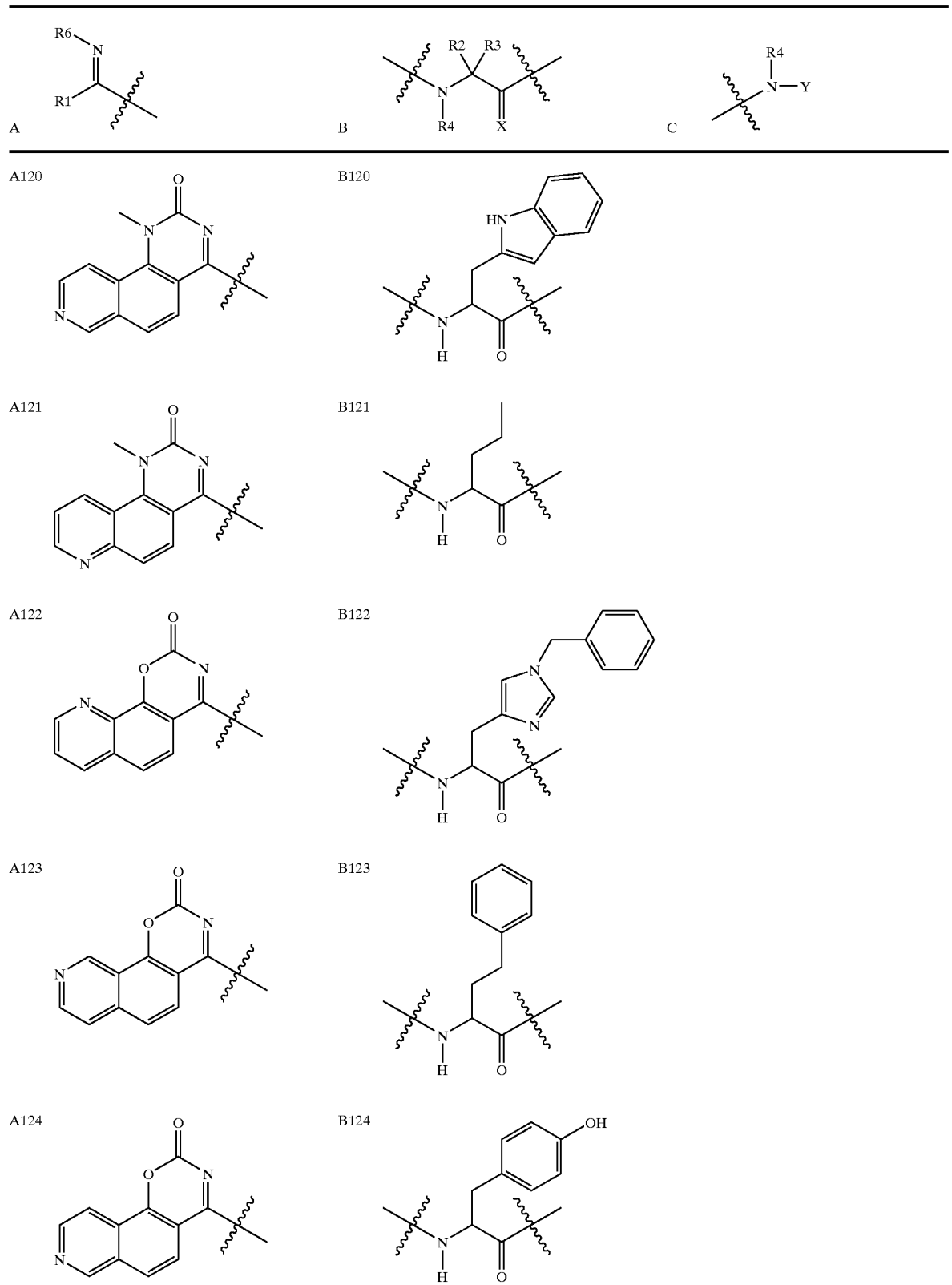

TABLE I-continued
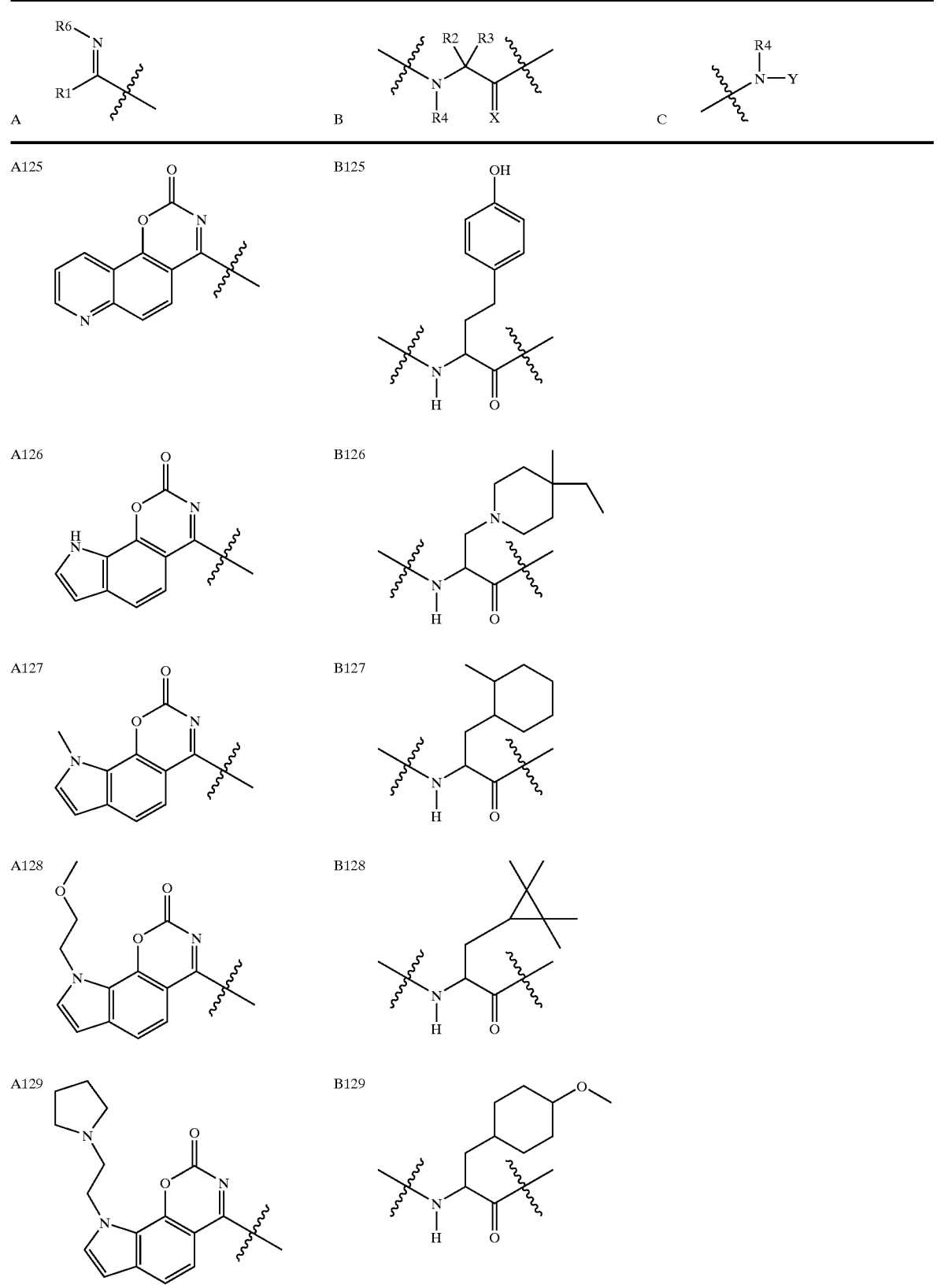

TABLE I-continued
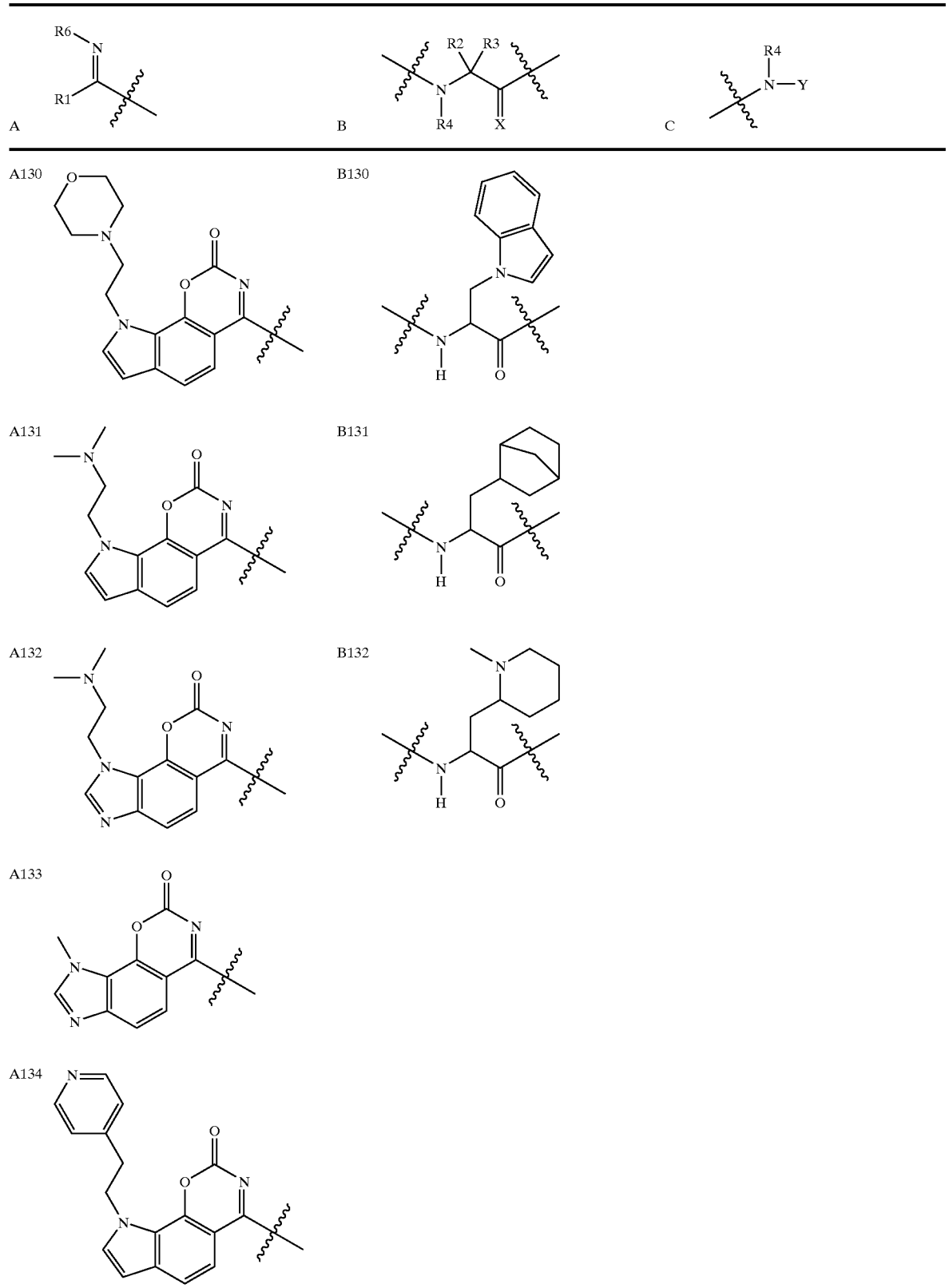

TABLE I-continued

| A | B | C |
|---|---|---|
| R6-N=C(R1)- (with wavy bond to methyl) | -N(R4)-C(R2)(R3)-C(X)-N(R4)- | -N(R4)-Y |

A135: [structure: 2,2,2-trifluoroethyl carbamate N=C(morpholinyl)- group]

A136: [structure: 9-methyl-2-oxo-purin-6-yl group]

A137: [structure: 9-(2-dimethylaminoethyl)-2-oxo-purin-6-yl group]

A138: [structure: 9-methylpurin-6-yl group]

A139: [structure: 9-(2-dimethylaminoethyl)purin-6-yl group]

A140: [structure: (4-NR2-cyclohexyl)methyl carbamate N=C(morpholinyl)- group]

R is hydrogen or alkyl and the pharmaceutically acceptable derivatives thereof.

The following subgeneric aspect of the compounds of the formulas (Ia) and (Ib) is postulated to possess Cathepsin K activity:

The broadest embodiment of the formula (Ia) and (Ib) as described hereinabove and wherein $R_1$ is a bond, C1–4 alkoxy, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, C1–2 alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one more $R_c$;

$R_c$ is methyl, ethyl, cyclohexyl, cyclopentyl, phenyl, naphthyl, bicyclo[3.1.0]hexanyl, bicyclo[1.1.1] pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, or $R_c$ is phenoxycarbonylamino, phenylcarbamoyloxy, phenylsulfonylamino, phenylaminosulfonyl, amino wherein the nitrogen atom may be independently mono or di-substituted by methyl or phenyl, or $R_c$ is chloro, fluoro, hydroxy, oxo, carboxy or cyano; or $R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono- di-substituted by C1–5 alkyl, phenyl or benzyl, or $R_5$ is carboxy.

Preferred cathepsin K inhibitors are those as described immediately above and wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, or $R_c$ is acetylamino, benzoylamino, methylthio, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is C1–5 alkyl or C1–5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono- di-substituted by C1–3 alkyl, phenyl or benzyl, or $R_5$ is carboxy.

Most preferred cathepsin K inhibitors are those as described immediately above and wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl; and $R_5$ is C1–3 alkyl or C1–3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or $R_5$ is carboxy.

Most preferred cathepsin K inhibitors are those as described immediately above and wherein:

R₁ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

R₃ is n-propyl, i-butyl, propenyl, i-butenyl or 2,2-dimethylpropyl;

and

R₂ and R₃ together with the carbon they are attached optionally form a ring selected from cyclopentyl, cyclohexyl, or cycloheptyl.

Further compounds of Formula (Ia), made up of components A, B and C are provided in Table II below. Any and all combinations of A, B and C components within the structural limitations of Formula (Ia), comprise a compound of the invention preferably possessing CAT K activity.

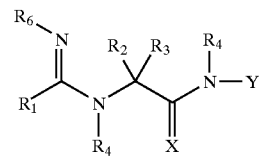
(Ia)

wherein for the Formula (Ia), the components

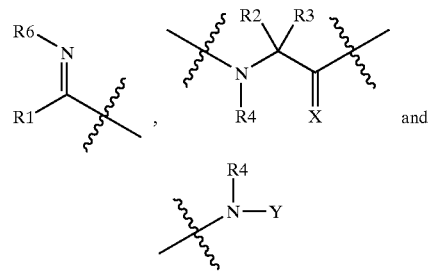

are chosen from any combination of A, B and C as follows:

TABLE II

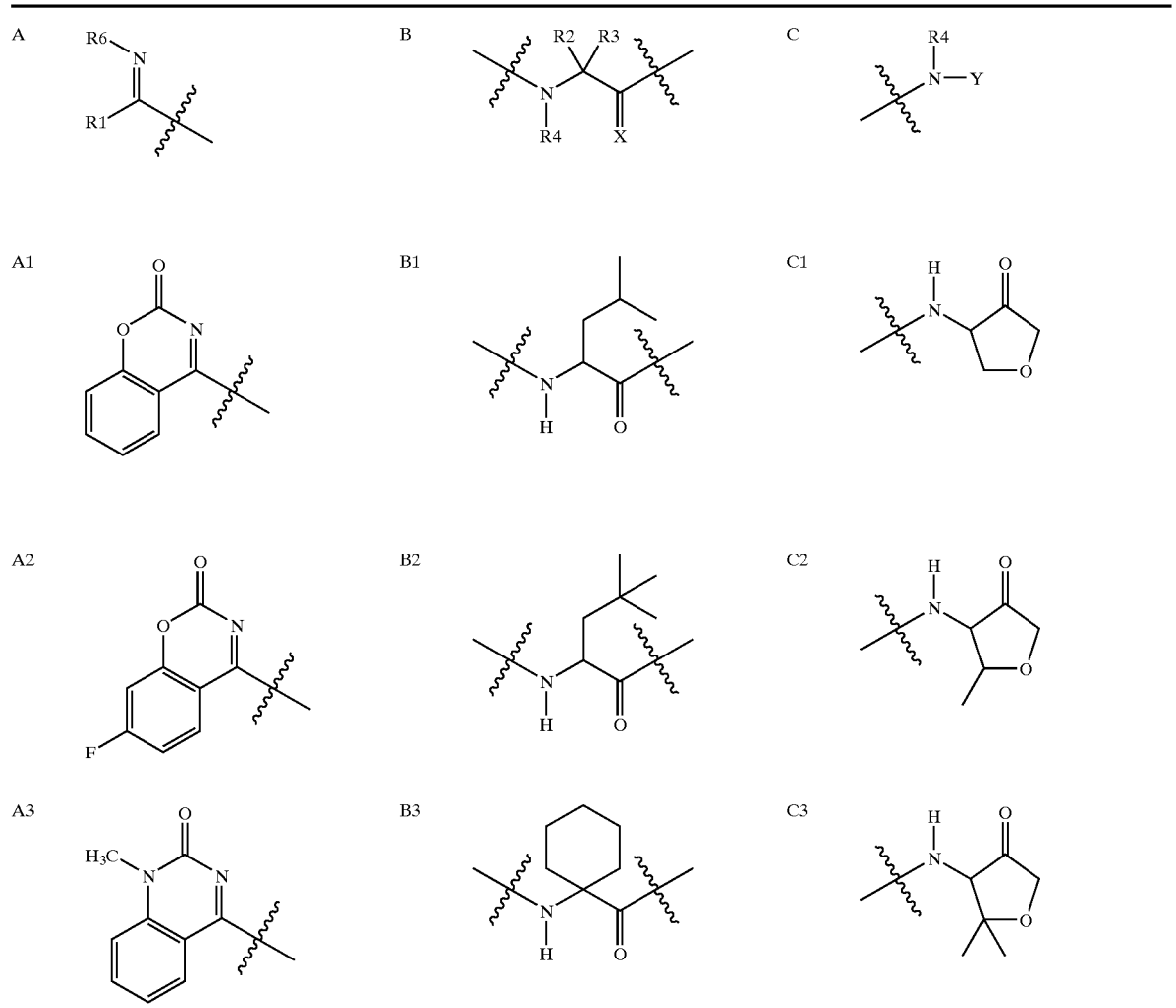

TABLE II-continued
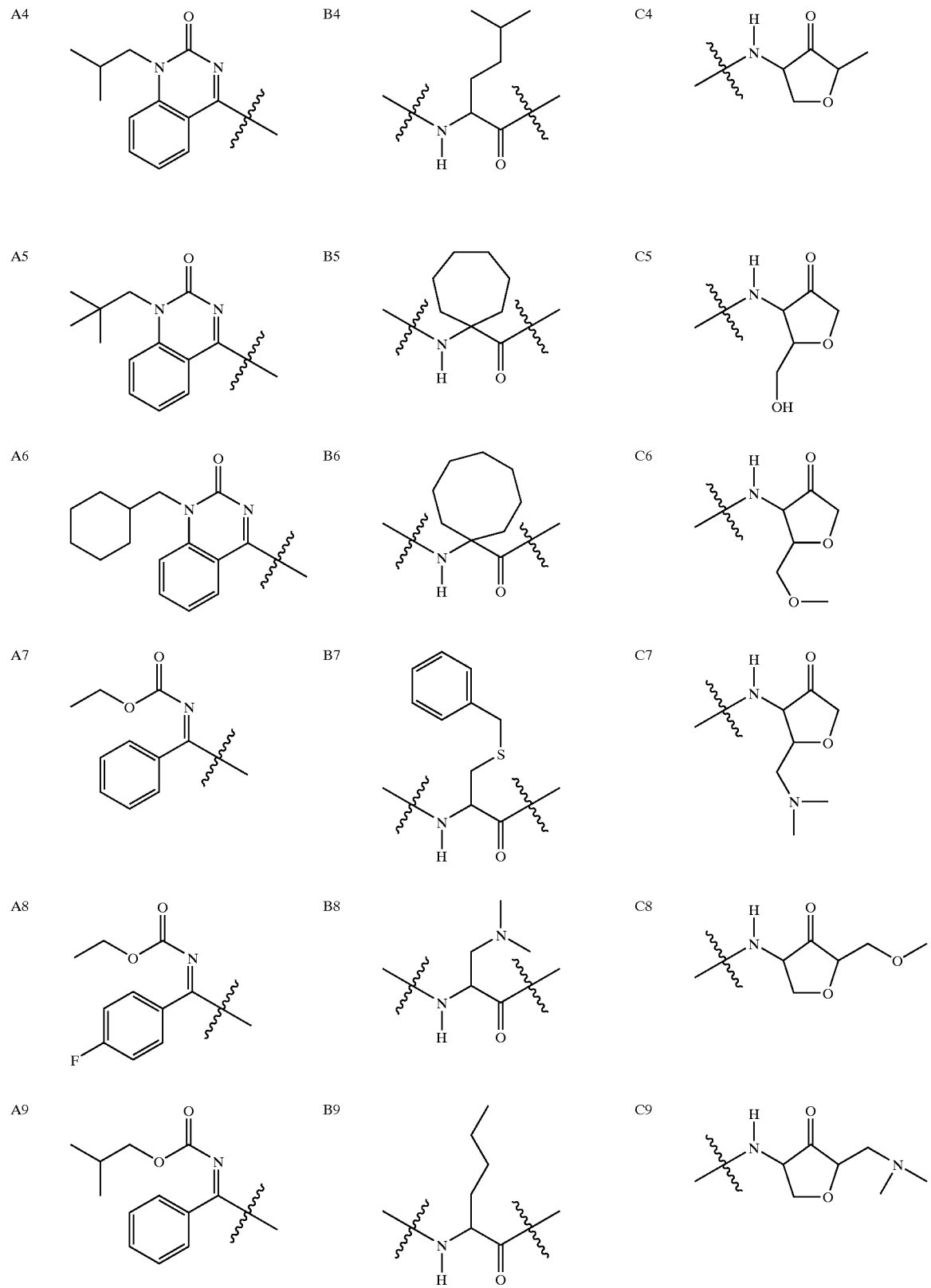

TABLE II-continued
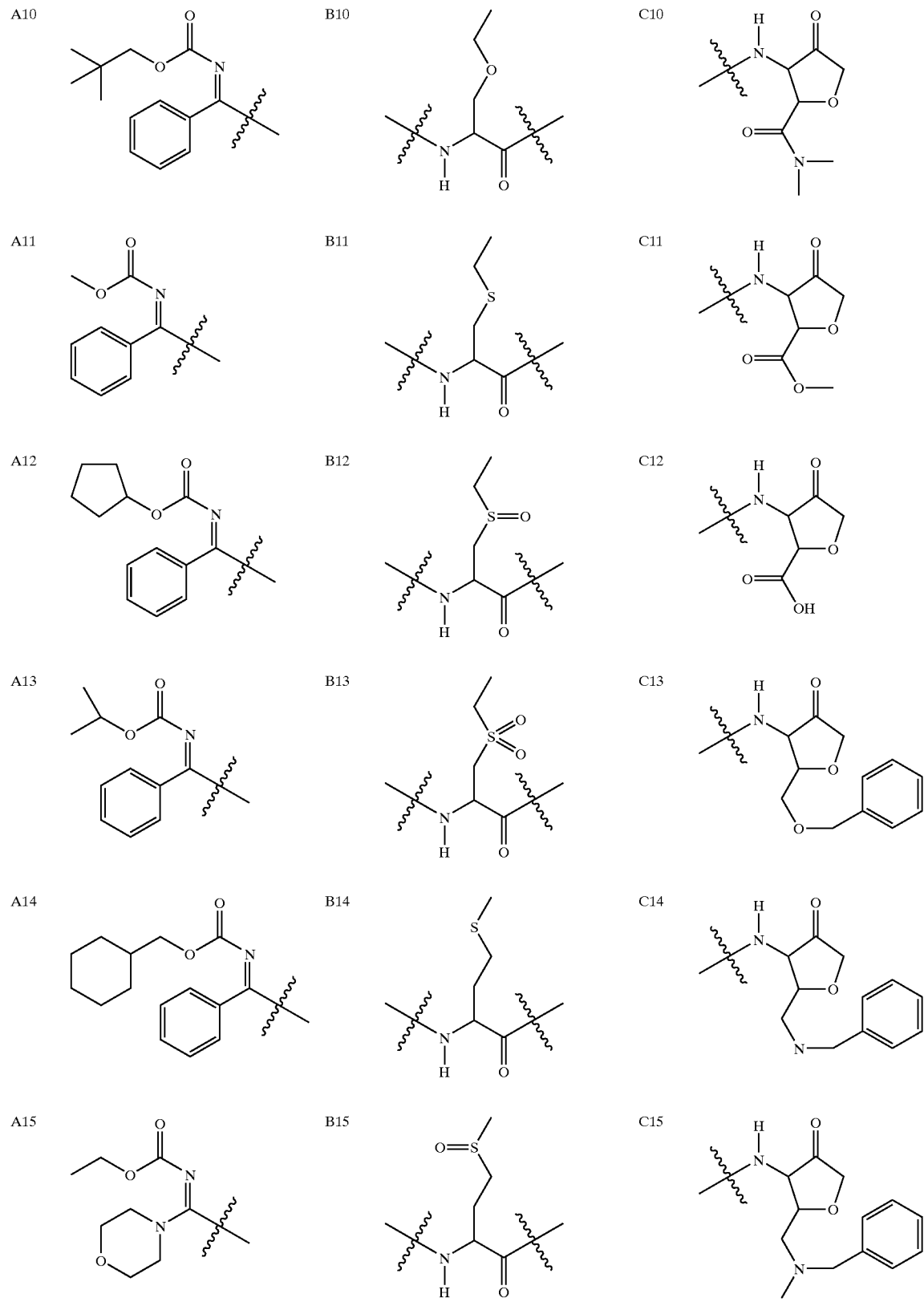

TABLE II-continued
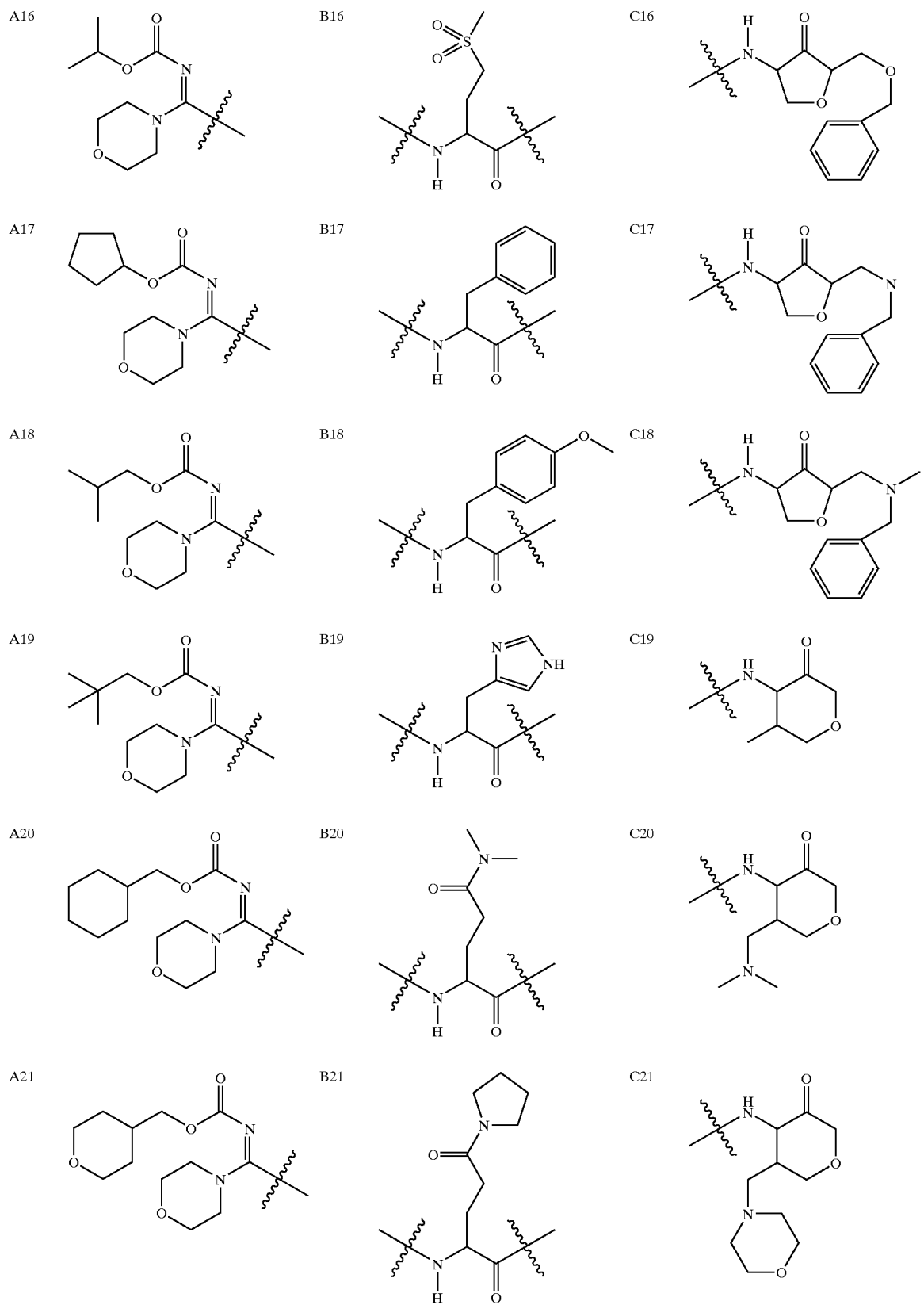

TABLE II-continued
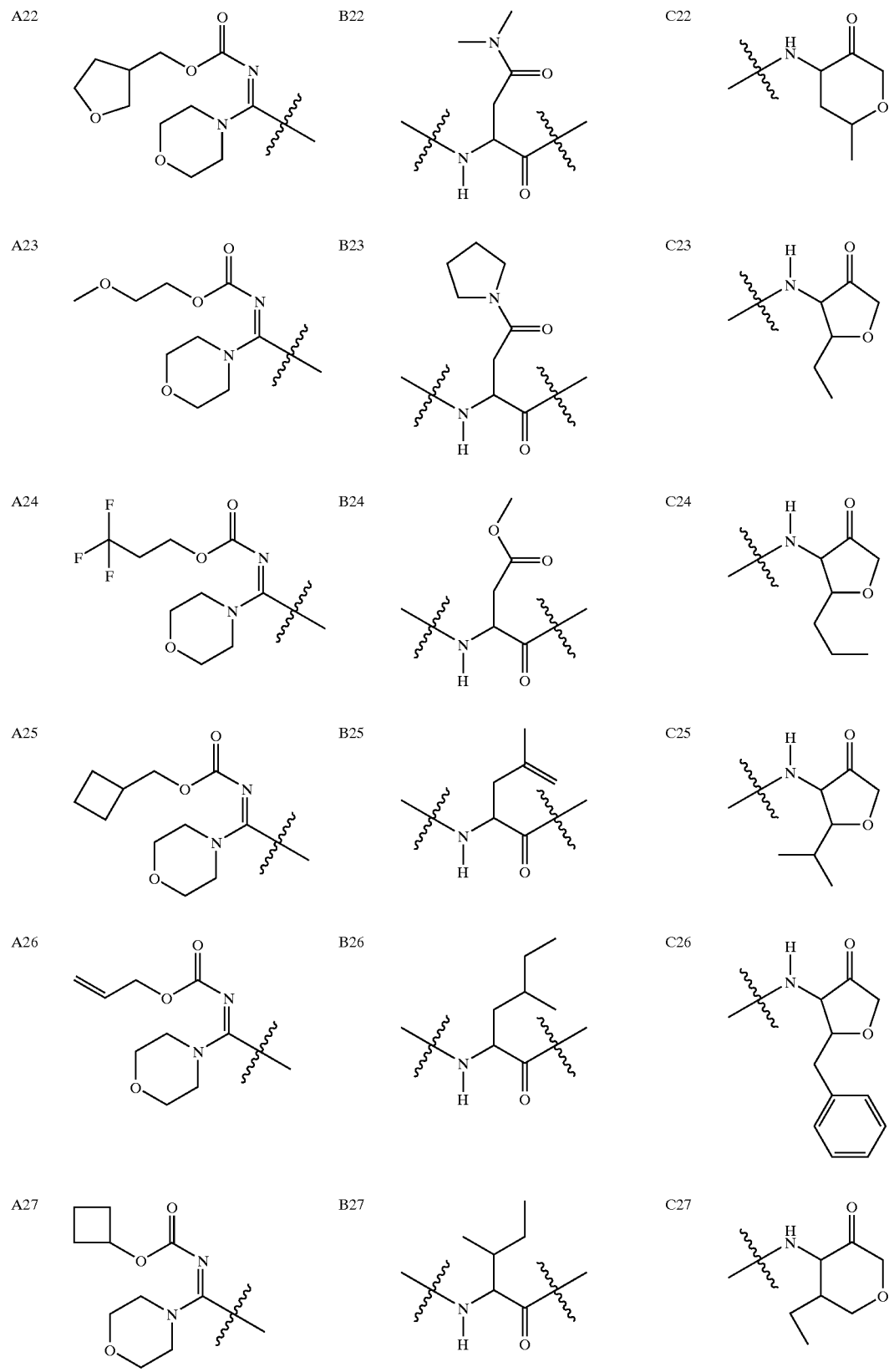

TABLE II-continued
| | | | |
|---|---|---|---|
| A28 | 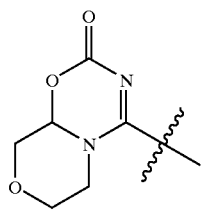 | B28 | 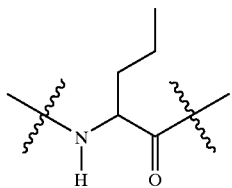 |
| A29 | 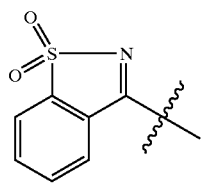 | B29 | 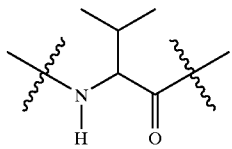 |
| A30 | 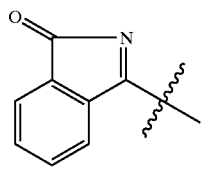 | B30 | 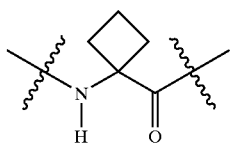 |
| A31 | 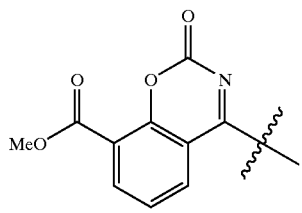 | B31 | 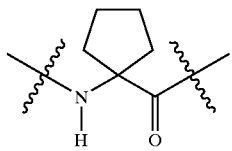 |
| A32 | 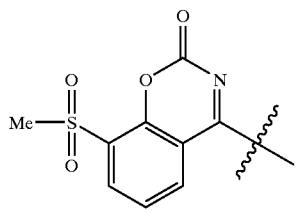 | | |
| A33 | 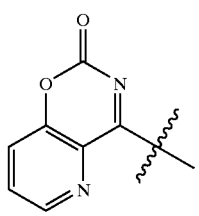 | | |
| A34 | 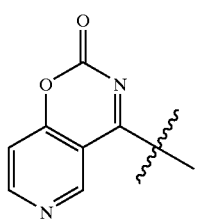 | | |

TABLE II-continued
A35 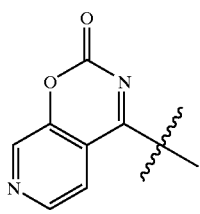
A36 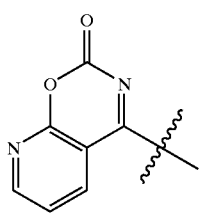
A37 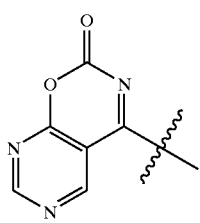
A38 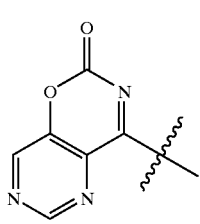
A39 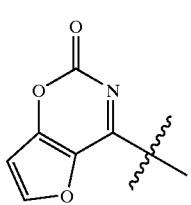
A40 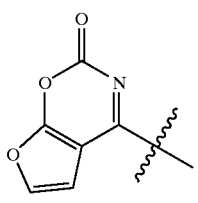
A41 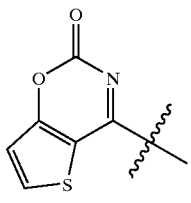

TABLE II-continued
A42 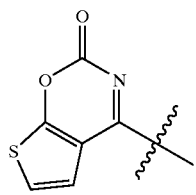
A43 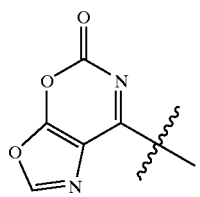
A44 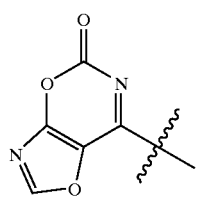
A45 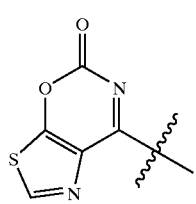
A46 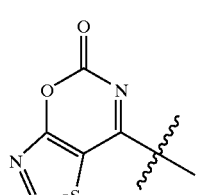
A47 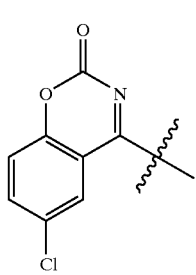
A48 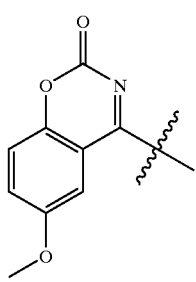

TABLE II-continued
| A49 | 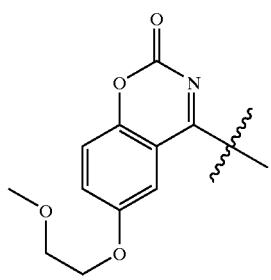 |
| A50 | 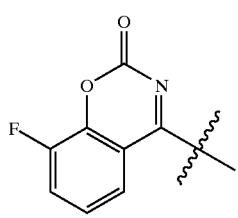 |
| A51 | 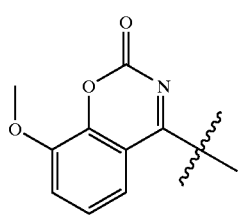 |
| A52 | 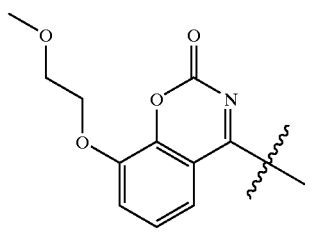 |
| A53 | 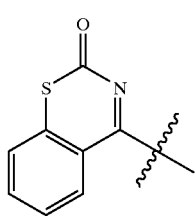 |
| A54 | 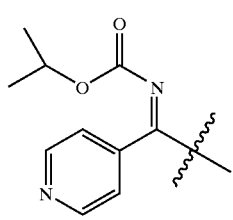 |
| A55 | 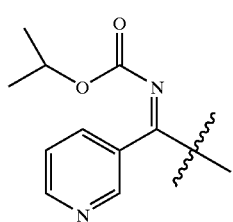 |

TABLE II-continued
A56 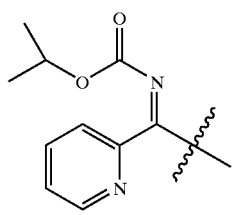
A57 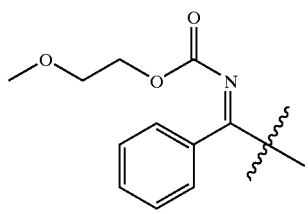
A58 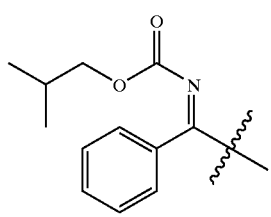
A59 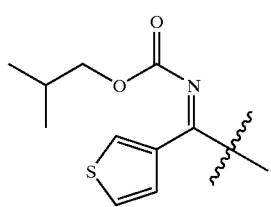
A60 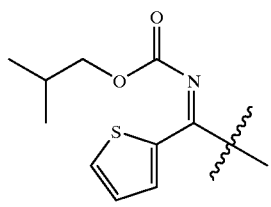
A61 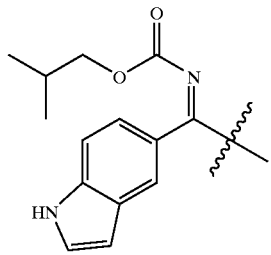
A62 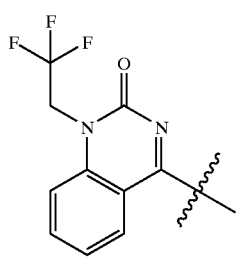

TABLE II-continued
A63 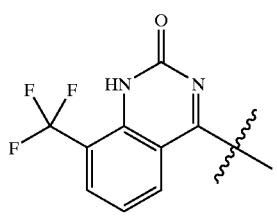
A64 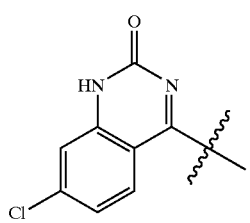
A65 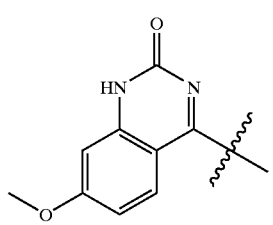
A66 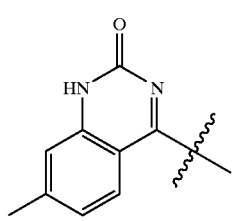
A67 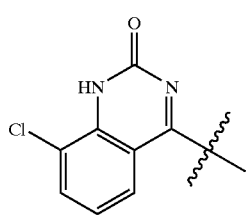
A68 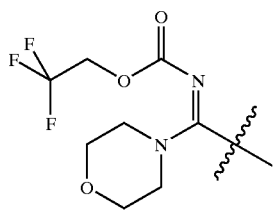
A69 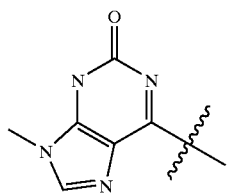

TABLE II-continued

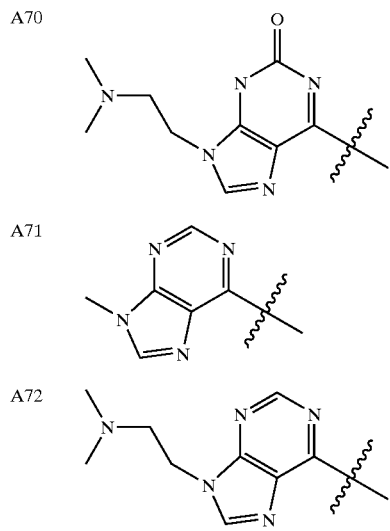

and the pharmaceutically acceptable deviates thereof.

For all the compounds disclosed in this application, in the event the nomenclature is in conflict with the structure, it shall be understood that the compound is defined by the structure Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

Some of the compounds can exist in more than one tautomeric form. The invention includes all such tautomers.

It shall be understood by one of ordinary skill in the art that all compounds of the invention are those which are chemically stable. For example, compounds possessing dangling valencies or free radicals are not within the scope of the invention.

The invention includes pharmaceutically acceptable derivatives of compounds of formula (Ia/Ib). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs of compounds of the formula (Ia/Ib). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (Ia/Ib), thereby imparting the desired pharmacological effect.

In order that the invention herein described may be more fully understood, the following detailed description is set forth. As used herein, the following abbreviations are used:
BOC or t-BOC is tertiary-butoxycarbonyl;
t-Bu is tertiary-butyl;
DMF is dimethylformamide;
EtOAc is ethyl acetate;
THF is tetrahydrofuran;
EDC is 1-(3-dimethylaminopropyl)-3-ethylcarbodimide hydrochloride and
HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halo" or "halogen" refers to a halogen radical selected from fluoro, chloro, bromo or iodo. Representative halo groups of the invention are fluoro, chloro and bromo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, benzoxazinyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, The term "heterocycle" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl- 1,1-dioxide, 1,2,6-thiadiazinanyl- 1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

In all alkyl groups or carbon chains where one or more carbon atoms or methylene groups are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkyl, alkylene, alkoxyalkyl, alkoxycarbonylalkyl, alkylthioalkyl, alkylthiosulfonealkyl, alkylthiosulfonylalkyl, amino alkyl, mono or di-alkylaminoalkyl, mono or di-alkylamidoC1–5 alkyl.

As used herein above and throughout this application, "nitrogen" and "sulfur" include any oxidized form of nitrogen and sulfur and the quaternized form of any basic nitrogen.

General Synthetic Methods

The invention also provides processes of making the present novel compounds of formula (Ia) and (Ib). Compounds of the invention may be prepared by methods described below, those found in U.S. application Ser. Nos. 09/434,106, 09/627,869, 09/655,351 and 09/808,439 each incorporated herein in their entirety, and by methods known to those of ordinary skill in the art.

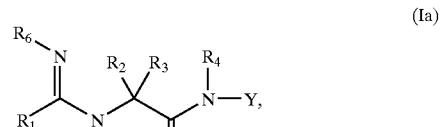

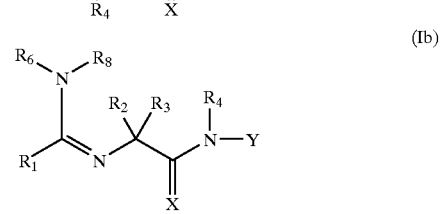

Y is:

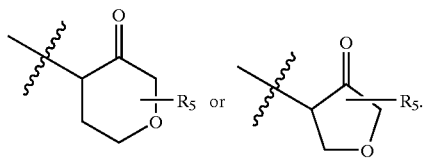

The synthesis of compounds of formula (Ia) may be carried out as described in Scheme I below. In Schemes I and II below, Y represents either of the structures shown above.

Scheme I

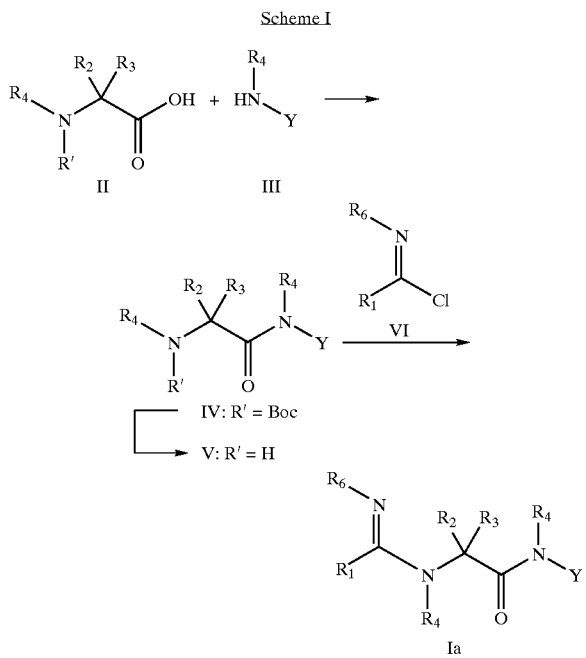

As illustrated in Scheme I, an amino acid bearing a suitable protecting group R' (II), such as a BOC group, is reacted with an amine bearing the group Y (III) under suitable coupling conditions to provide IV. Examples of standard coupling conditions include combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride or preparing the mixed anhydride of II by reacting with a chloroformate such as isobutyl chloroformate in the presence of a suitable base such as 4-methylmorpholine, followed by reaction with III. This is followed by deprotection (removal of R') to give V. Reaction of V with the desired halo imino compound (VI), in the presence of a suitable base, such as 4-methylmorpholine or diisopropylethylamine, provides the desired compound of formula Ia.

The synthesis of intermediate III, YNHR$_4$, is known in the art and described in the literature. For example, WO/0069855 describes the synthesis of 3-amino-4-oxo-tetrahydrofurans.

An alternate approach illustrated in Scheme II may be used to obtain compounds in which R$_1$ is an amine. As illustrated in Scheme II, intermediate V (Scheme I) is reacted with an isothiocyanate bearing R$_6$ (VII) in a suitable solvent such as methylene chloride to provide thiourea VIII. If V is used as an acid salt, a suitable base such as triethylamine is added. Reaction of VIII with an amine (R'R"NH) in a solvent such as DMF and in the presence of a suitable catalyst such as HgCl$_2$ provides the desired compound of formula Ia (R$_1$=R'R"N).

Scheme II

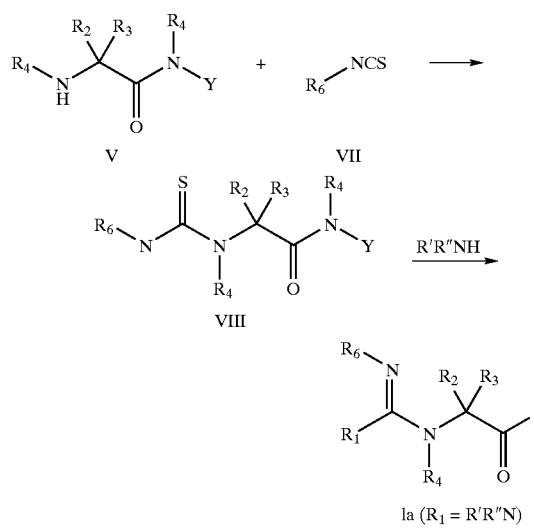

In order that this invention be more fully understood, the following examples are set forth. These examples are for the purpose of illustrating embodiments of this invention, and are not to be construed as limiting the scope of the invention in any way.

The examples which follows are illustrative and, as recognized by one skilled in the art, particular reagents or conditions could be modified as needed for individual compounds. Starting materials used in the scheme below are either commercially available or easily prepared from commercially available materials by those skilled in the art.

SYNTHETIC EXAMPLES

Example 1

Synthesis of ((2S,3S)-3-amino-2-methyl-4-oxo-tetrahydrofuran hydrochloride salt

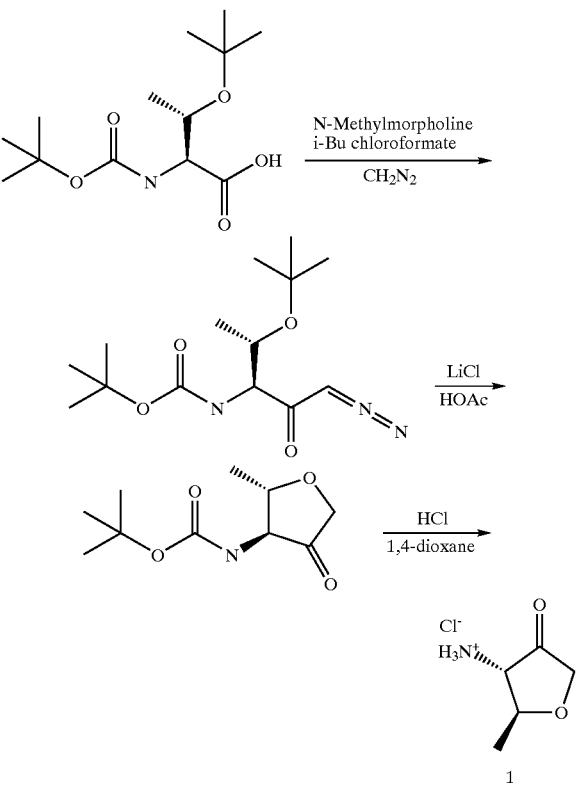

N-methylmorpholine (1.7 mL, 2.2 equiv) was added to a solution of (2S, 3S)-N-Boc 4)-t-butylthreonine (2.0 g, 7.0 mmol, 1.0 equiv) in anhydrous CH$_2$Cl$_2$ (40 mL). The resulting solution was cooled to −15° C. under an argon atmosphere. Iso-butylchloroformate (0.94 mL, 1.03 equiv) was added and the mixture was stirred for 20 min. A solution of diazomethane in Et$_2$O (75 mL, about 67 mmol) was added over 5 min, the cold bath was removed and the reaction was allowed to warm over a 1 h period. Acetic acid was added dropwise until the bubbling stopped. The reaction solution was diluted with CH$_2$Cl$_2$ (150 mL) and washed sequentially with saturated sodium bicarbonate (2×100 mL), water (1×100 mL) and saturated brine (1×100 mL). The organic layer was dried over Na$_2$SO$_4$, decanted and concentrated in vacuo to yield (2S, 3S)-N-Boc-O-t-butyl-threonyldiazomethane as a yellow oil that was used without further purification.

A solution of LiCl (2.72 g, 64 mmol) was prepared in 80% aqueous AcOH (80 mL). The solution was cooled to 5° C. and then added to the crude (2S, 3S)N-boc-O-t-butyl-threonyldiazomethane (2.0 g). The diazoketone slowly dissolved over a period of 15 min. Stirring was continued for 1 h during which time the reaction was allowed to warm to room temperature. The reaction was concentrated under high vacuum and the residue dissolved in EtOAc (100 mL) and washed sequentially with water (100 mL), sodium bicarbonate solution (2×100 mL) and saturated brine (50 mL). The EtOAc solution was dried over Na$_2$SO$_4$, decanted and concentrated. The crude product was purified by flash chromatography on silica (50 g) using EtOAc/hexanes.

Additional purification may be performed, if required, by recrystallization from EtOAc/heptane. ((2S,3S)-2-methyl-4-oxo-tetrahydro-furan-3-yl)-carbamic acid tert-butyl ester is isolated as a white solid.

The above tert-butyl ester (1.00 g, 4.60 mmol) was dissolved in 2 mL of 1,4-dioxane. HCl in 1,4-dioxane (4.0 M, 16 mmol) was added. This mixture was stirred at room temperature for 30 min. The solvent was removed in vacuo to give the title compound as a white solid in quantitative yield.

Example 2

Synthesis of (S)-3-cyclohexyl-N-((2S,3S)2-methyl-4-oxo-tetrahydro-furan-3-yl)-2-(2-oxo-2H-benzo[e][1,3]oxazin-4-ylamino)-propionamide

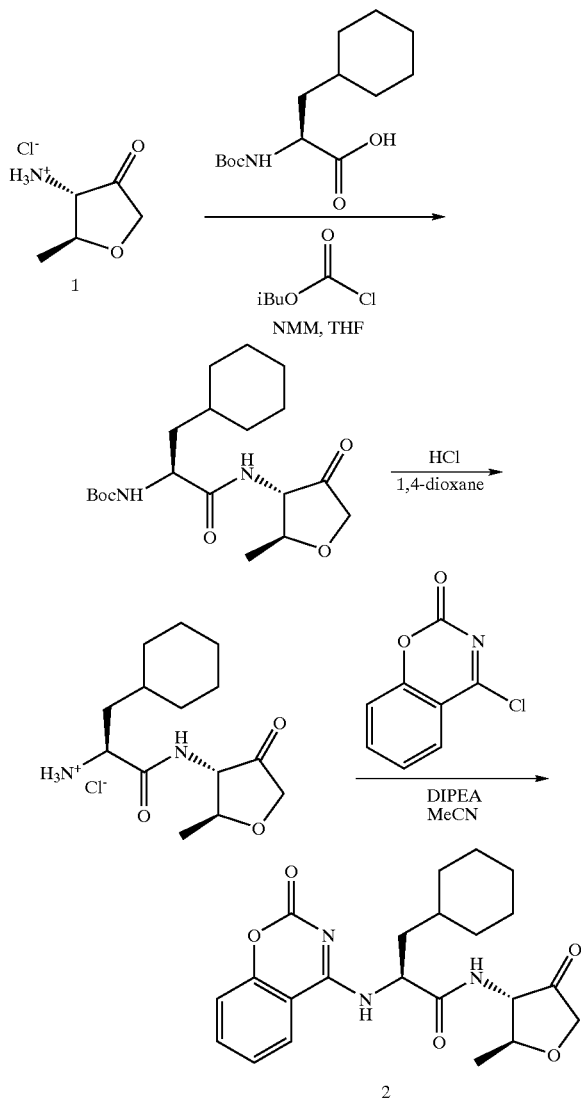

(S)—N-Boc-cyclohexyl alanine (0.815 g, 3.00 mmol) was dissolved in 20 mL of dry THF. To this solution at 0° C. was added 4-methyl morpholine (0.55 mL, 3.00 mmol) followed by isobutyl chloroformate (0.64 mL, 3.00 mmol). This reaction mixture was stirred at 0° C. for 40 min. A suspension of ((2S,3S)-3-amino-2-methyl-4-oxo-tetrahydrofuran hydrochloride salt (Example 1) (455 mg, 3.00 mmol) and 4-methylmorpholine (0.550 mL, 3.00 mmol) in 10 mL of dry THF was added via a syringe. The reaction mixture was stirred at room temperature for 16 h. The solvent was removed in vacuo. The residue was washed with ethyl ether and dichloromethane. The solution was concentrated and purified by silica gel chromatography eluting with 3% MeOH in dichloromethane to give the desired amide (0.663 g, 60%) as a yellow oil.

The above amide (0.663 mg, 1.80 mmol) was dissolved in 2 mL of dioxane. HCl in dioxane (4.0 M, 5.0 mL, 20 mmol) was added. The reaction mixture was stirred at room temperature for 30 min. The solvent was removed in vacuo to give (S)-2-amino-3-cyclohexyl-N-((2S,3S)-2-methyl-4-oxo-tetrahydro-furan-3-yl)-propionamide hydrochloride as a white solid in quantitative yield.

The above amino amide (0.305 g, 1.00 mmol) and benzoxazinone chloride (0.367 g, 2.00 mmol) was dissolved in 15 mL of acetonitrile. Diisopropylethylamine (1 mL) was added. The reaction mixture was stirred at room temperature for 48 h. The solvent was removed in vacuo and the residue was purified by silica gel chromatography eluting with 50% EtOAc in hexane to give the title compound (51 g, 12%) as a white solid. MS e/z 412 (M-H).

Example 3

[1-[(S)-2-cyclohexyl-1-((2S,3S)-2-methyl-4-oxo-tetrahydro-furan-3-ylcarbamoyl)ethylamino]-1-morpholin-4-yl-meth(Z)-ylidene]-carbamic acid ethyl ester

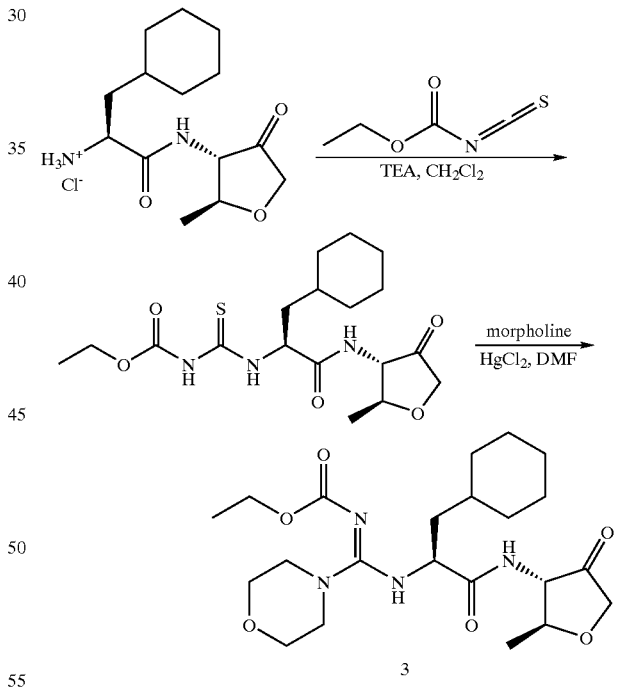

(S)-2-Amino-3-cyclohexyl-N-((2S,3 S)-2-methyl-4-oxo-tetrahydro-furan-3-yl)-propionamide hydrochloride (See Example 2) (0.626 g, 2.06 mmol) was dissolved in 8 mL of dry dichloromethane. To this solution at 0° C., under nitrogen, was added ethoxycarbonyl isothiocyanate (0.30 g, 2.28 mmol) followed by triethylamine (0.48 g, 4.75 mmol). This mixture was stirred at 0° C. for 1 h. The solvent was removed in vacuo. The residue was purified by silica gel chromatography eluting with 0–50% EtOAc and hexane to give the desired thiourea (0.540 g, 71%) as an off white solid.

The above thiourea intermediate (0.10 g, 0.250 mmol) was dissolved in 5 mL of DMF. To this solution was added mercuric chloride (0.204 g, 0.750 mmol) and morpholine (0.065 g, 0.750 mmol). The reaction mixture was stirred at room temperature for 2 h. The solid was removed by filtration and washed with MeOH. The filtrate was concentrated and purified by silica gel chromatography eluting with 0–10% MeOH in dichloromethane to give the title compound (0.043 g, 38%) as an off white solid. MS e/z 453 (M+H).

Methods of Therapeutic Use

The compounds of the invention are useful in inhibiting the activity of cathepsin S, K, F, L and B. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there are provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis including contact and atopic dermatitis, insulin-dependent diabetes mellitus, endometriosis and asthma including allergic asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also inhibit cathepsin K. In doing so, they may block inappropriate degradation of bone collagen and other bone matrix proteases. Thus, there is provided a method for treating diseases where these processes play a role such as osteoporosis. Inhibition of cathepsins F, L, and B are also within the scope of the invention due to similarity of the active sites in cysteine proteases as described above.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties

Expression and Purification of recombinant human Cathepsin S may be done as described in U.S. Pat. No. 6,313,117.
Inhibition of Cathepsin S Human recombinant cathepsin S expressed in Baculovirus is used at a final concentration of 10 nM in buffer. Buffer is 50 mM Na acetate, pH 6.5, 2.5 mM EDTA, 2.5 MM TCEP. Enzyme is incubated with either compound or DMSO for 10 min at 37° C. Substrate 7-amino-4-methylcoumarin, CBZ-L-valyl-L-valyl-L-arginineamide (custom synthesis by Molecular Probes) is diluted to 20 $\mu$M in water (final concentration of 5 M), added to assay and incubated for additional 10 minutes at 37° C. Compound activity is measured by diminished fluorescence compared to DMSO control when read at 360 nm excitation and 460 nm emission.

Examples listed above were evaluated for inhibition of cathepsin S in the above assay. All had $IC_{50}$ values of 100 micromolar or below.
Inhibition of Cathepsin K, F, L and B:

Inhibition of these enzymes by particular compounds of the invention may be determined without undue experimentation by using art recognized methods as provided herein-below each of which is incorporated herein by reference:
Cathepsin B, and L assays are to be found in the following references:
1. Methods in Enzymology, Vol. 244, Proteolytic Enzymes: Serine and Cysteine Peptidases, Alan J. Barrett, ed.

Cathepsin K assay is to be found in the following reference:
2. Bromme, D., Okamoto, K., Wang, B. B., and Biroc, S. (1996) *J. Biol. Chem.* 271, 2126–2132.

Cathepsin F assays are to be found in the following references:
3. Wang, B., Shi, G. P., Yao, P. M., Li, Z., Chapman, H. A., and Bromme, D. (1998) *J. Biol. Chem.* 273, 32000–32008.
4. Santamaria, I., Velasco, G., Pendas, A. M., Paz, A., and Lopez-Otin, C (1999) *J. Biol. Chem.* 274, 13800–13809.

Preferred compounds to be evaluated for inhibition of Cathepsin K, F, L and B in the above assays desirably have $IC_{50}$ values of 100 micromolar or below.

What is claimed is:
1. A compound of formula (Ia) or (Ib):

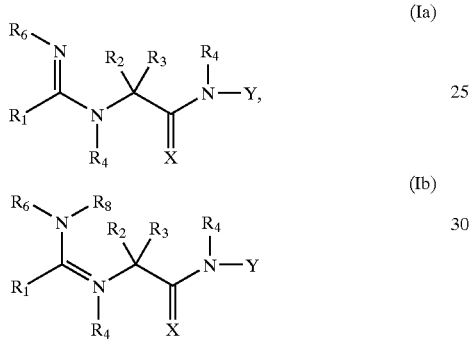

wherein for the formulas Ia or Ib:
Y is:

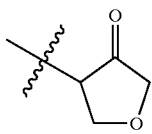

wherein Y is optionally substituted by one or more $R_5$;
$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, heterocyclyl selected from azepanyl, azocanyl, pyrrolidinyl, piperidinyl, morpholinyl, thiomorpholinyl, piperazinyl, indolinyl, pyranyl, tetrahydropyranyl, tetraydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, heterocyclyloxy wherein the heterocyclyl moiety is selected from those herein described in this paragraph, hydroxy or amino; wherein $R_1$ is optionally substituted by one or more $R_a$;

$R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$;

with the proviso that $R_1$ and $R_a$ simultaneously cannot be a bond;

$R_b$ is a C1–6 saturated or unsaturated branched or unbranched carbon chain optionally partially or fully halogenated wherein one or more carbon atoms are optionally replaced by O, N, S(O), $S(O)_2$ or S and wherein said chain is optionally independently substituted with 1–2 oxo groups, —$NH_2$, or one or more C1–4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;

or $R_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;

$R_2$ is hydrogen or C1–3 alkyl;

$R_3$ is a bond, hydrogen, alkyl wherein one or more carbon atoms are optionally replaced by O, S or N wherein it shall be understood if N is not substituted by $R_c$ then it is NH, or $R_3$ is C2–10alkylene, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl and quinoxalinyl, C3–8 cycloalkyl, arylC1–5alkyl or aryl wherein $R_3$ is optionally substituted by one or more $R_c$;

$R_c$ is C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–12 cycloalkyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, aryloxy, aroyl, aryloxycarbonyl, aroyloxy, or $R_a$ is aroylamino, alkylthio, arylthio, aryloxycarbonylamino, arylcarbamoyloxy, arylsulfonylamino, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

each $R_4$ is independently hydrogen, hydroxy or C1–3 alkyl;

$R_5$ is alkyl or acyl each optionally substituted by alkoxy, aryloxy, benzyloxy, hydroxy, carboxy, aryl, benzyl, heterocyclyl chosen from pyrrolidinyl, piperidinyl, morpholinyl, thiomorpholinyl and piperazinyl or amino wherein the N atom is optionally mono- di-substituted by alkyl, aryl or benzyl, or $R_5$ is carboxy;

$R_6$ is hydrogen, hydroxy, nitrile or a C1–6 saturated or unsaturated branched or unbranched alkyl optionally partially or fully halogenated wherein one or more C atoms are optionally replaced by O, NH, S(O), $S(O)_2$ or S and wherein said chain is optionally independently substituted with 1–2 oxo groups, —$NH_2$, one or more C1–4 alkyl, C3–7 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formulas (Ia) or (Ib) optionally form a 4 to 8 membered mono or 7–14 membered polycyclo heteroring system, each aromatic or nonaromatic, wherein each ring is optionally substituted by one or more $R_7$;

each $R_7$ and $R_8$ are independently:

hydrogen, C1–5 alkyl chain optionally interrupted by one or two N, O or $S(O)_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated, halogen, hydroxy, oxo, carboxy, nitrile, nitro or $NH_2C(O)$—;

m is 0, 1 or 2;

and

X is =O, =S or =N—$R_6$ wherein $R_6$ is as defined above, or the pharmaceutically acceptable salts, esters, isomers or tautomers thereof.

2. The compound according to claim 1 wherein $R_1$ and $R_6$ of the formula (Ia) or formula (Ib) form:

a monocyclic 5, 6 or 7 membered aromatic or nonaromatic heterocyclic ring optionally substituted by $R_7$;

a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

or a tricyclic ring wherein the abovementioned bicyclic ring is further fused to a third 5–7 membered aromatic or nonaromatic heterocyclic or carbocyclic ring wherein each ring is optionally independently substituted by one or more $R_7$;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein $R_3$ is optionally substituted by one or more $R_c$;

$R_c$ is C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, $C_{1-5}$ alkoxy, aryloxy, arylC1–5 alkoxy, aroyl, halogen, hydroxy, oxo or cyano;

$R_4$ is hydrogen or methyl;

$R_7$ and $R_8$ are independently hydrogen, C1–5 alkyl, C3–6 cycloalkyl, aryl, C1–5 alkoxy, aryloxy, benzyloxy each of the aforementioned are optionally halogenated, halogen, hydroxy, oxo, carboxy, nitrile, nitro or $NH_2C(O)$—;

m is 0, 1 or 2 and

X is O or S.

3. The compound according to claim 2 wherein $R_1$ and $R_6$ of the formula (Ia) or Formula (Ib) form:

a monocyclic 5 or 6 membered aromatic or nonaromatic heterocyclic ring optionally substituted by $R_7$;

a bicyclic ring having one 5, 6 or 7 membered aromatic or nonaromatic heterocyclic ring fused to a second 5–6 membered aromatic or nonaromatic heterocyclic or carbocyclic ring wherein each ring is optionally independently substituted by one or more $R_7$;

or a tricyclic ring having one 5, 6 or 7 membered aromatic or nonaromatic heterocyclic ring fused to a 5-6-membered aromatic or nonaromatic carbocyclic ring which in turn is fused to a 5, 6 or 7 membered aromatic or nonaromatic heterocyclic ring;

$R_2$ is hydrogen or methyl;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono- di-substituted by C1–5 alkyl, phenyl or benzyl, or $R_5$ is carboxy;

$R_7$ and $R_8$ are independently hydrogen, C1–4 alkyl, C5–6 cycloalkyl, C1–4 alkoxy, halogen, hydroxy, oxo, carboxy, nitrile, nitro or $NH_2C(O)$—; and X is O.

4. The compound according to claim 3 and wherein:

$R_1$ and $R_6$ of the formula (Ia) or formula (Ib) form:

a bicyclic ring having one 5 or 6 membered aromatic or nonaromatic heterocyclic ring fused to a second 5–6 membered heteroaryl, heterocycle or phenyl ring;

or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring;

wherein each ring is optionally independently substituted by one or two $R_7$ $R_2$ is hydrogen;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is C1–5 alkyl or C1–5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono- di-substituted by C1–3 alkyl, phenyl or benzyl, or $R_5$ is carboxy.

5. The compound according to claim 4 and wherein:

$R_1$ and $R_6$ of the formula (Ia) or Formula (Ib) form:

a bicyclic ring having one 5–6 membered aromatic or nonaromatic heterocyclic ring fused to a phenyl or 5–6 membered aromatic or nonaromatic heterocyclic ring;

a tricyclic ring having one 5–6 membered aromatic or nonaromatic heterocyclic ring fused to a 6-membered aromatic or nonaromatic carbocyclic ring which in turn is fused to a 5–6 membered aromatic or nonaromatic heterocyclic ring;

wherein each ring is optionally independently substituted by one or two $R_7$;

$R_3$ is a bond, C1–10 alkyl wherein one or more carbon atoms are optionally replaced by O, S or N, or $R_3$ is C2–4alkylene, C5–6 cycloalkyl, heterocyclic 1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_c$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo; and $R_5$ is C1–3 alkyl or C1–3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or $R_5$ is carboxy.

6. The compound according to claim 5 and wherein:

$R_1$ and $R_6$ of the formula (Ia) form:

the bicyclic ring:

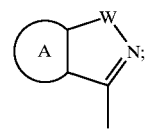

wherein W is $-S(O)_n-$, $>C(O)$, $-O-C(O)-$, $-S-C(O)-$ or $-NH-C(O)-$, n is 0, 1 or 2, fused ring A is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$;

or the tricyclic ring:

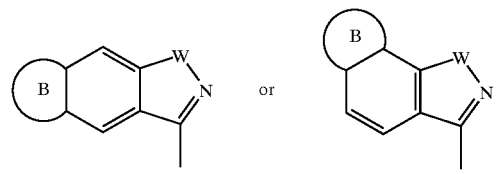

wherein W is $-S(O)_n-$, $>C(O)$, $-O-C(O)-$, $-S-C(O)-$ or $-NH-C(O)-$, n is 0, 1 or 2, fused ring B is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$;

$R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, spiro[3.5]nonyl, spiro[4.5]decanyl, cubanyl, 1,2,3,4-tetrahydronaphthyl, phenoxy, benzoyl, phenoxycarbonyl, benzoyloxy, phenylthio, fluoro or chloro.

7. The compound according to claim 6 and wherein:
R$_1$ and R$_6$ of the formula (Ia) form the bicyclic ring selected from:
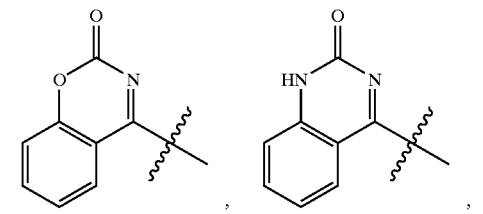,
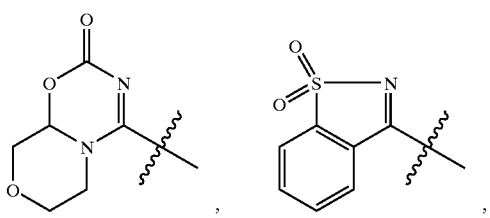,
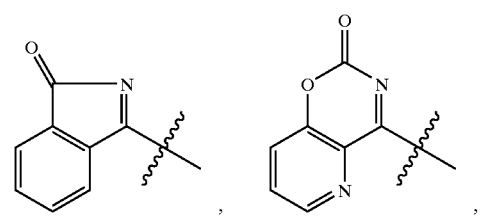,
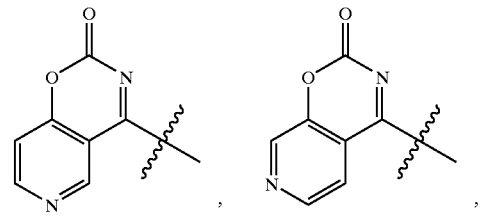,
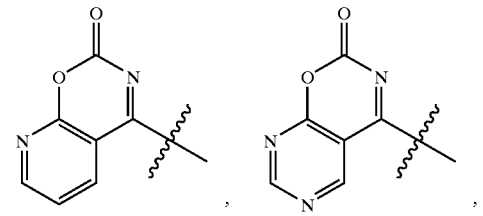,
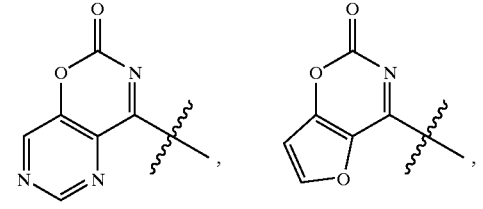,
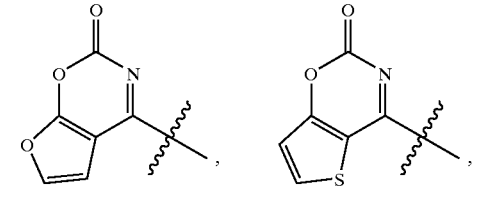,
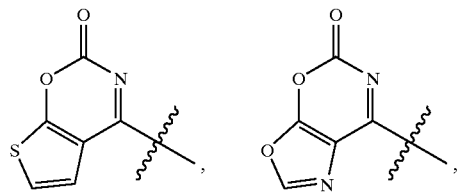,
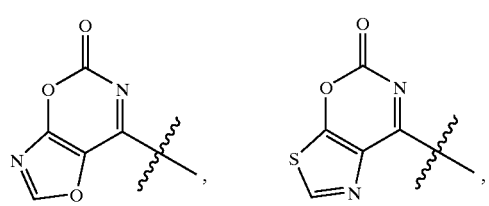,
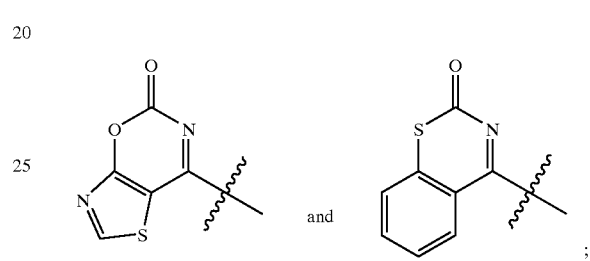 and ;
or R$_1$ and R$_6$ of the formula (Ia) form the tricyclic ring selected from:
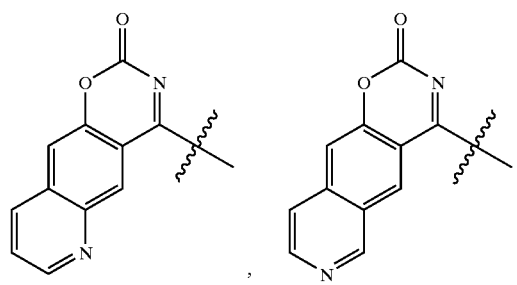,
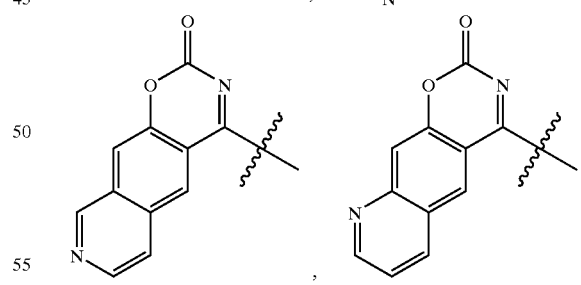,
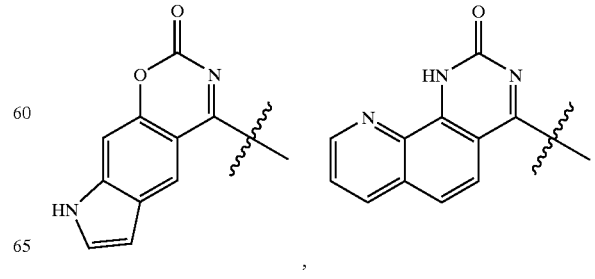, -continued

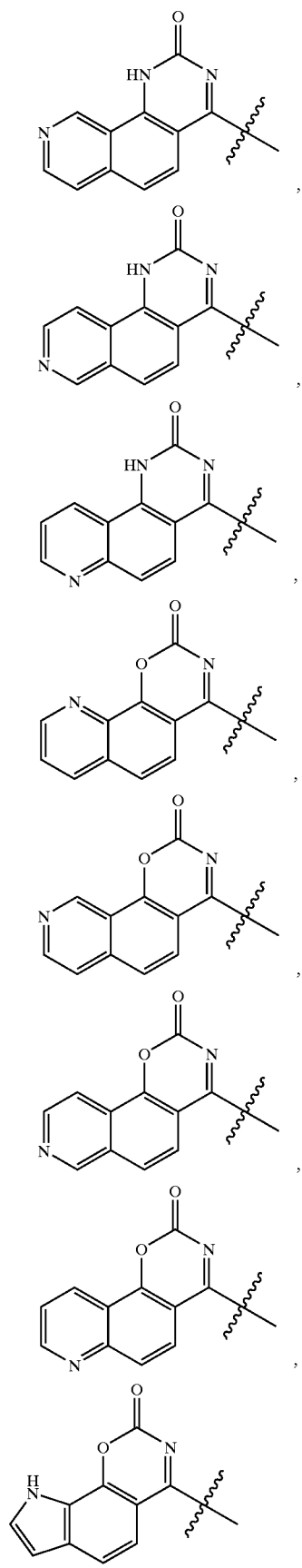
,

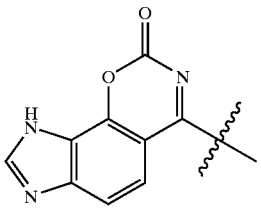
;

wherein each ring is optionally independently substituted by one or two $R_7$;

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4-tetrahydronaphthyl, spiro[2.5] octanyl, spiro[3.5] nonyl, spiro[4.5] decanyl, fluoro or chloro.

8. The compound according to claim 1 wherein:
$R_1$ and $R_6$ remain acyclic:

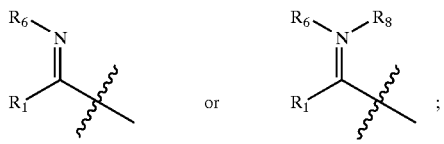

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein $R_3$ is optionally substituted by one or more $R_c$;

$R_c$ is C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_6$ is hydroxy, nitrile or a C1–5 saturated or unsaturated branched or unbranched alkyl optionally partially or fully halogenated wherein one or more C atoms are optionally replaced by O, NH or $S(O)_2$ and wherein said chain is optionally independently substituted with 1–2 oxo groups, —$NH_2$, one or more C1–4 alkyl, C3–6 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

$R_8$ is hydrogen, C1–5 alkyl, C3–6 cycloalkyl, aryl, C1–5 alkoxy, aryloxy, benzyloxy each of the aforementioned are optionally halogenated or hydroxy;

and

X is O.

9. The compound according to claim 8

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by $C_{1-5}$ alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono di-substituted by C1–5 alkyl, phenyl or benzyl, or $R_5$ is carboxy;

$R_6$ is nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with oxo, —$NH_2$, C3–6 cycloalkyl, piperidinyl, morpholinyl, thiomorpholinyl, piperazinyl, pyridinyl, pyrimidinyl or pyrazinyl; and $R_8$ is hydrogen, C1–3 alkyl, C3–6 cycloalkyl, phenyl, C1–3 alkoxy, benzyloxy each of the aforementioned are optionally halogenated or hydroxy.

10. The compound according to claim 9 wherein:

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is C1–5 alkyl or C1–-5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono- di-substituted by C1–3 alkyl, phenyl or benzyl, or $R_5$ is carboxy;

$R_6$ is nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with oxo, —$NH_2$, C3–6 cycloalkyl, morpholinyl or piperazinyl; and $R_8$ is hydrogen, C1–-3 alkyl, C1–3 alkoxy or hydroxy.

11. The compound according to claim 10 wherein:

$R_a$ is i-propyl, benzyloxy, cyclohexyl, phenyl, 4-(acetylamino)-phenyl, 4-(methanesulfonylamino)phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is a bond, C1–10 alkyl wherein one or more carbon atoms are optionally replaced by O, S or N, or $R_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is C1–3 alkyl or C1–3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or $R_5$ is carboxy;

$R_6$ is C3–6 cycloalkyloxycarbonyl, acetyl, C1–3alkylaminocarbonyl or C1–3alkoxycarbonyl; and $R_8$ is hydrogen, C1–3 alkyl or C1–3 alkoxy.

12. The compound according to claim 11 wherein:

$R_1$ is morpholin-4-yl, p-fluorophenyl or p-methoxyphenyl;

$R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5] octanyl, spiro[3.5] nonyl, spiro[4.5] decanyl, cubanyl, 1,2,3,4-tetrahydronaphthyl, phenoxy, benzoyl, phenoxycarbonyl, benzoyloxy, phenylthio, fluoro or chloro;

$R_6$ is C3–6 cycloalkyloxycarbonyl, acetyl, ethylaminocarbonyl or ethoxycarbonyl; and $R_8$ is hydrogen.

13. The compound according to claim 12 wherein:

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–-3 alkyl, mono or di-C1–-3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4-tetrahydronaphthyl, spiro[2.5] octanyl, spiro[3.5] nonyl, spiro[4.5] decanyl, fluoro or chloro.

14. A compound of the formula (Ia)

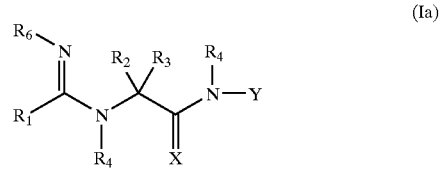

(Ia)

wherein for the Formula (Ia), the components

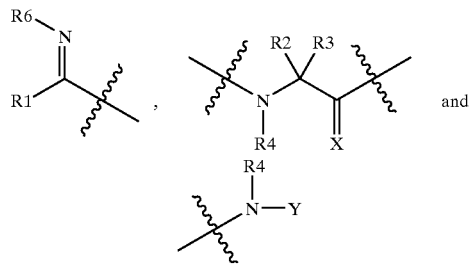

and are chosen from any combination of A, B and C as follows:

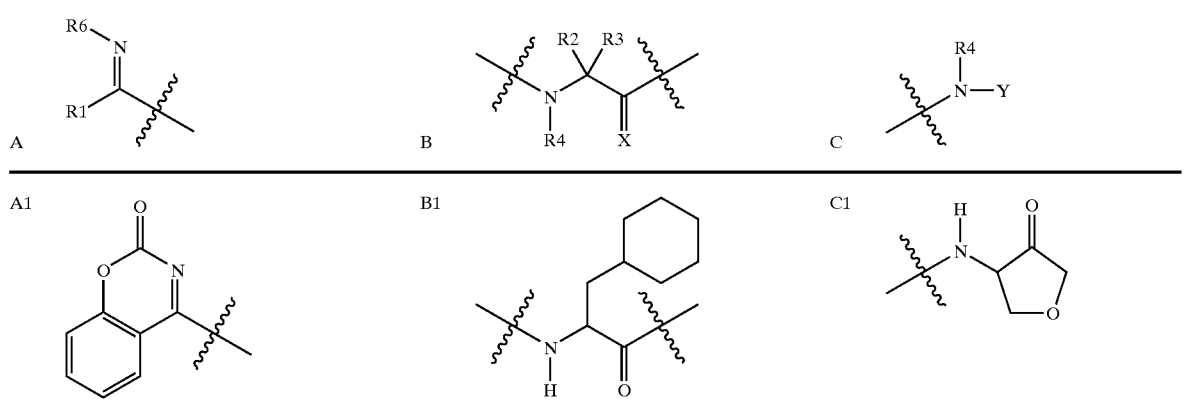

-continued
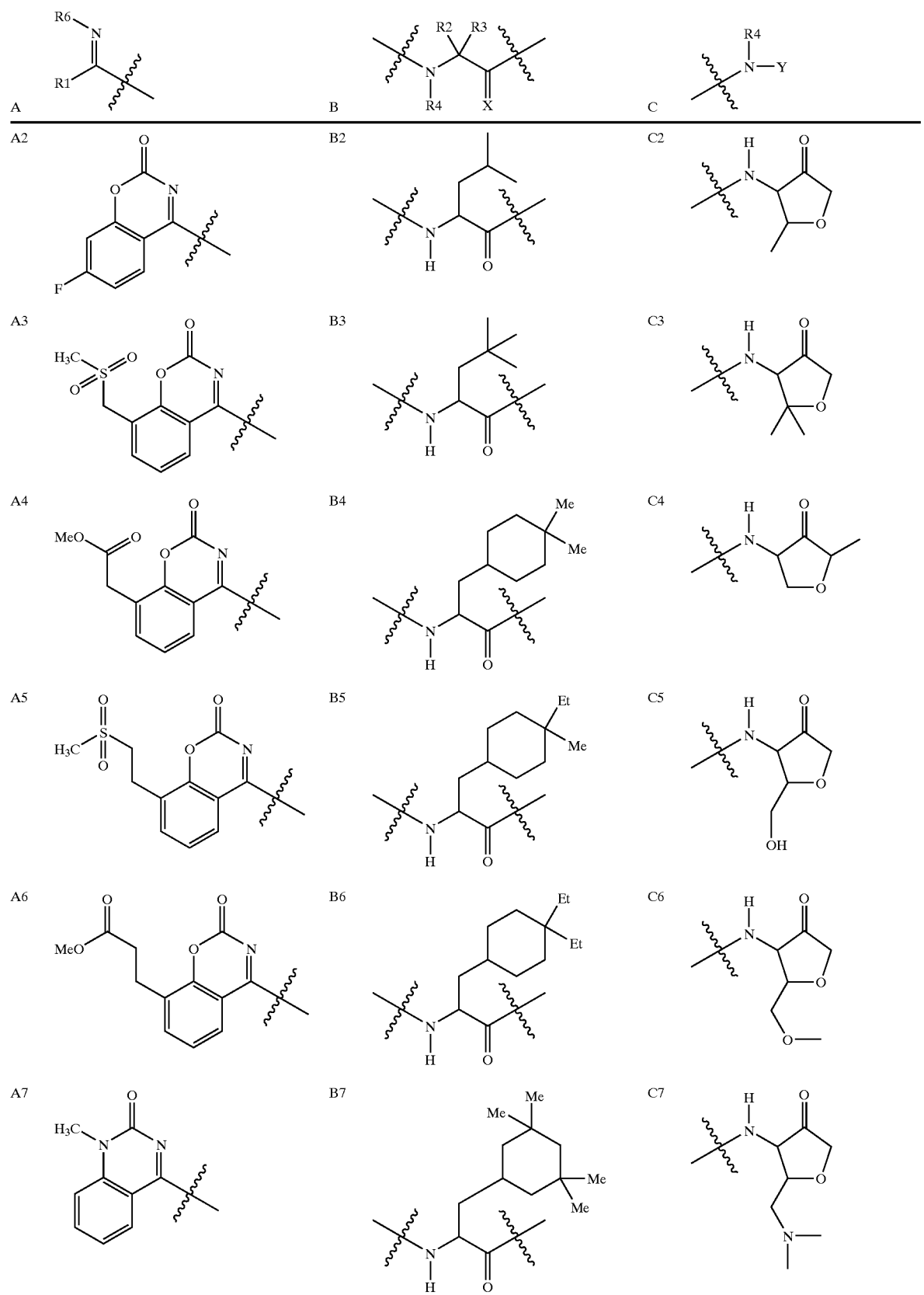

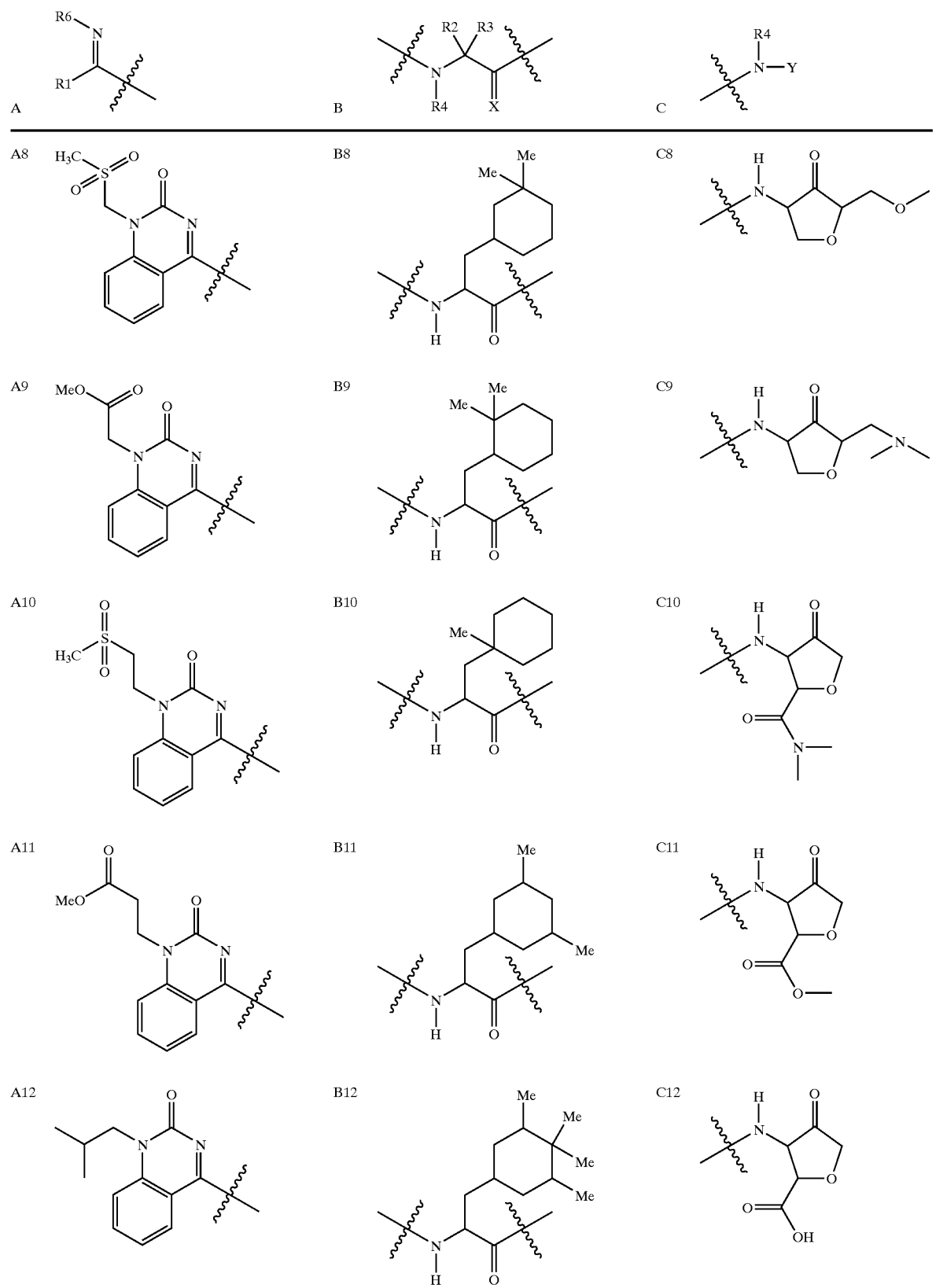

-continued
| A | B | C |
|---|---|---|
| 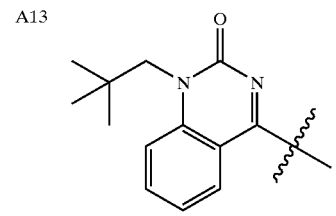 | 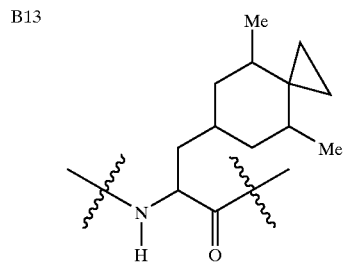 | 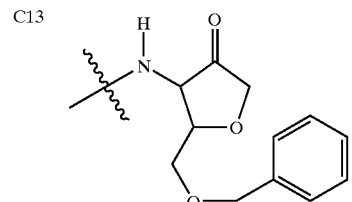 |
| A13 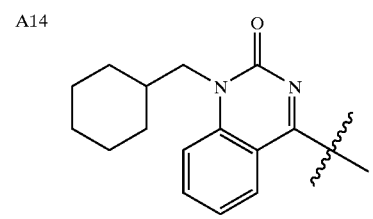 | B13 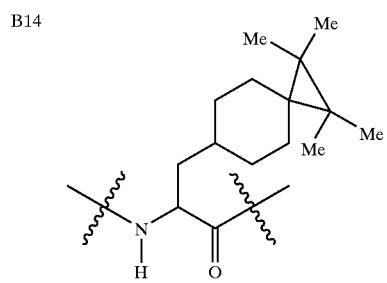 | C13 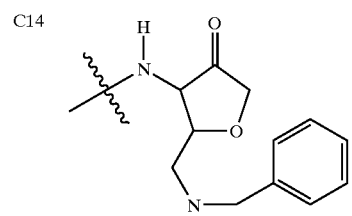 |
| A14 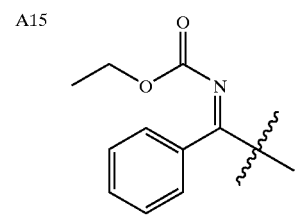 | B14 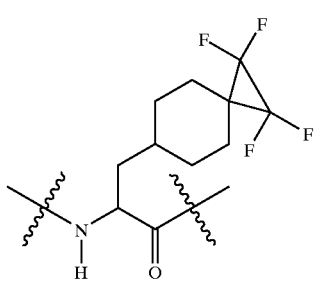 | C14 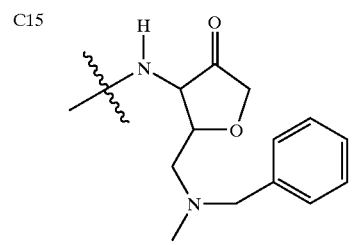 |
| A15 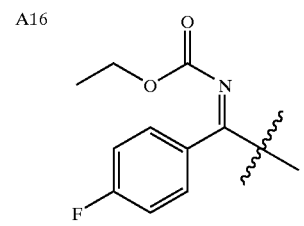 | B15 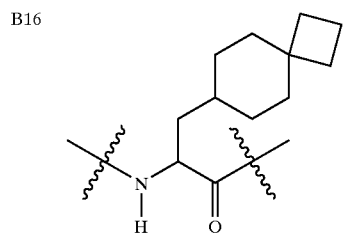 | C15 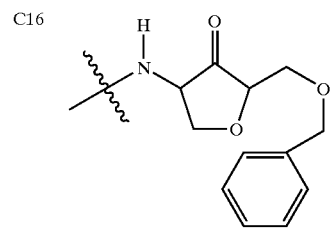 |
| A16 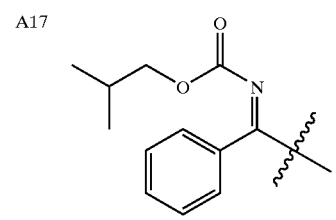 | B16 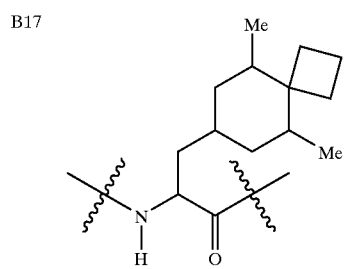 | C16 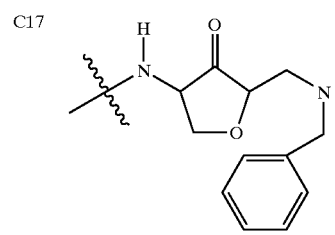 |
| A17 | B17 | C17 |

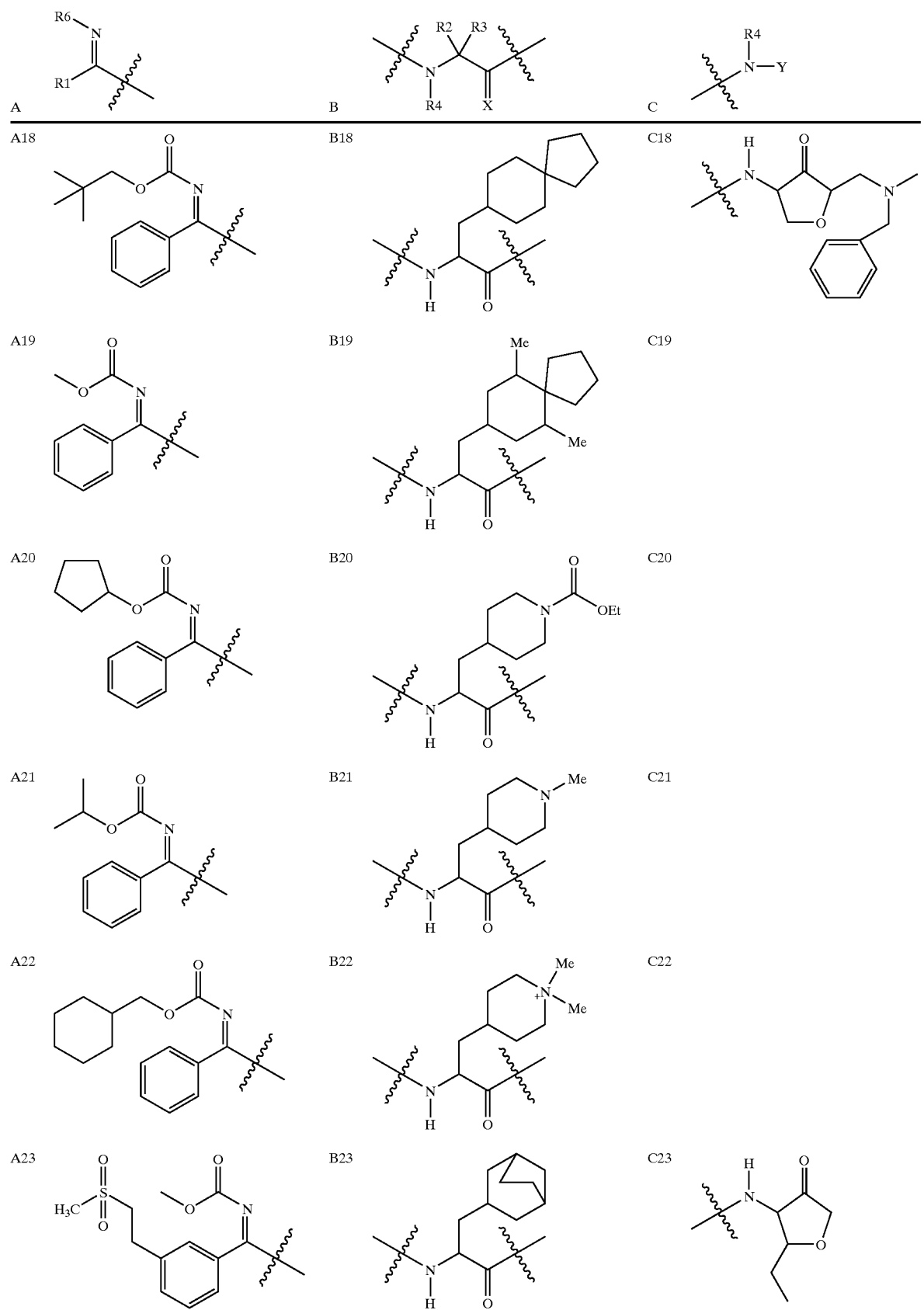

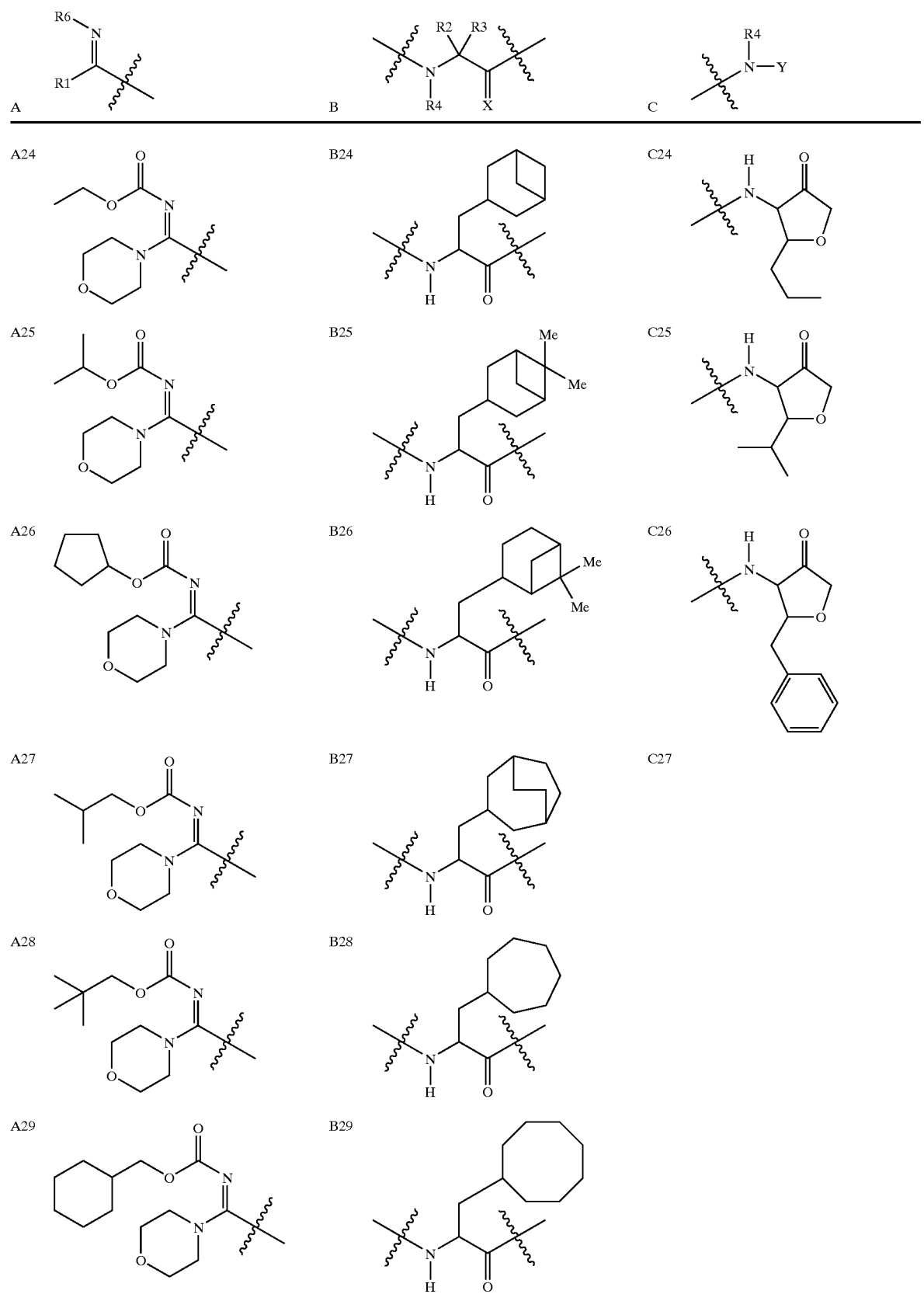

-continued
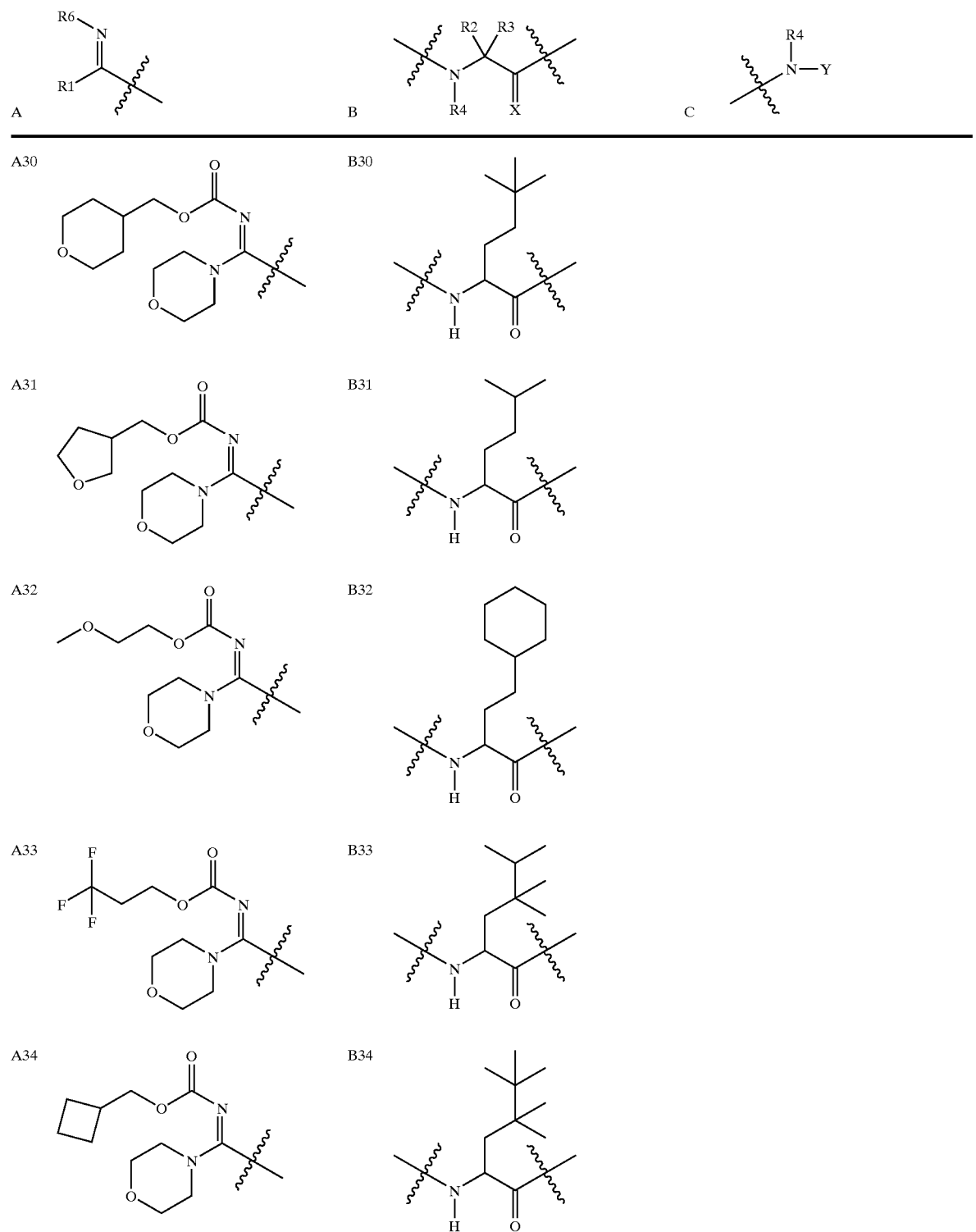

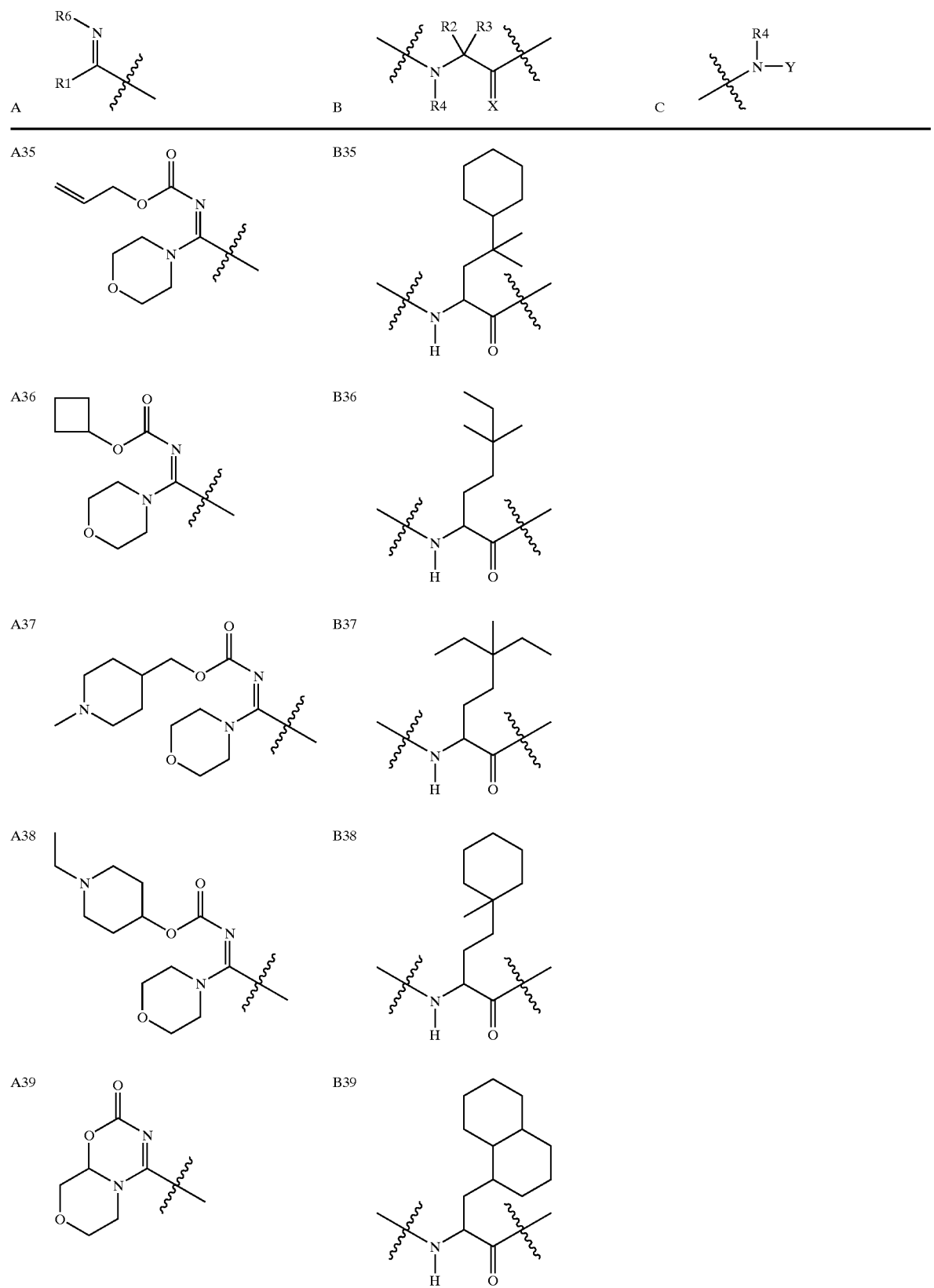

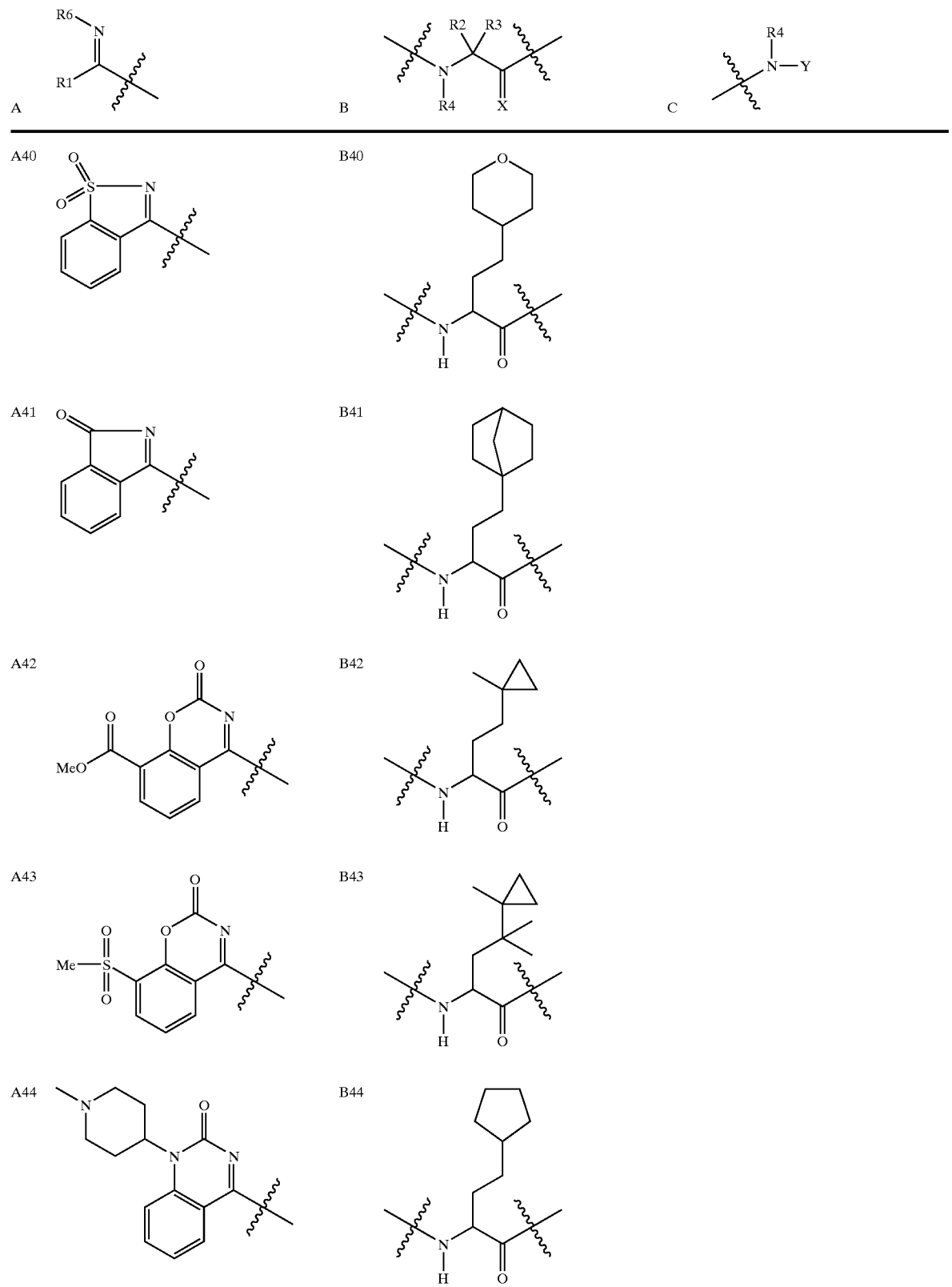

-continued
| A | B | C |
|---|---|---|
| 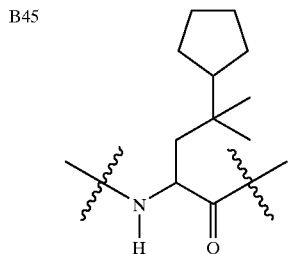 | 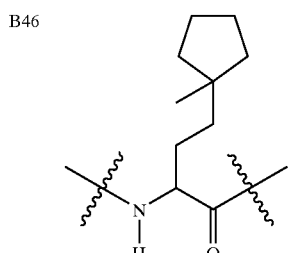 | |
| A45 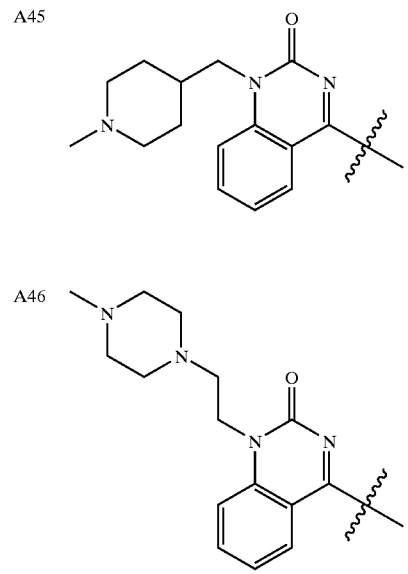 | B45 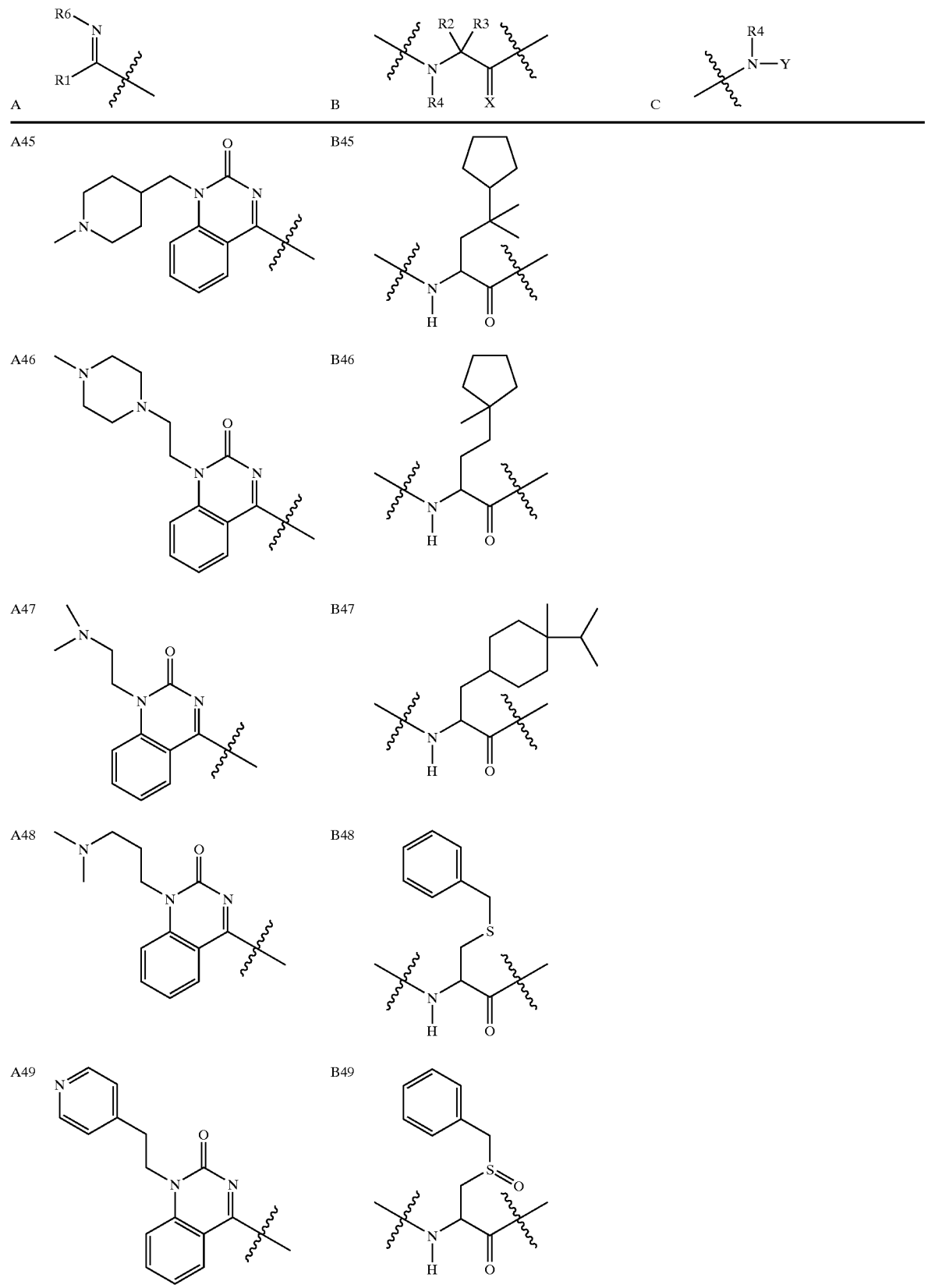 | |
|---|---|---|
| A46 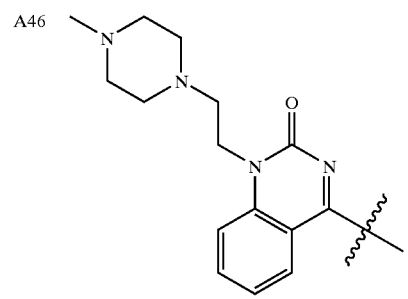 | B46 | |
| A47 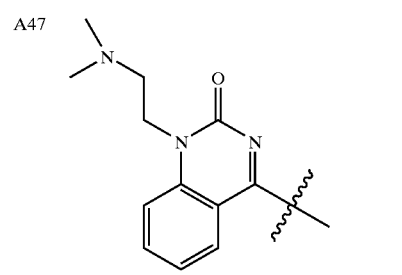 | B47 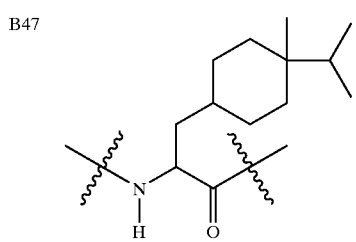 | |
| A48 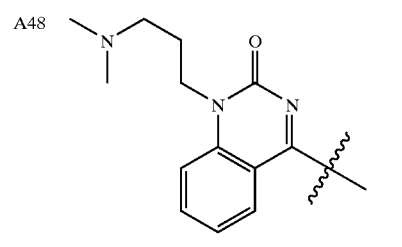 | B48 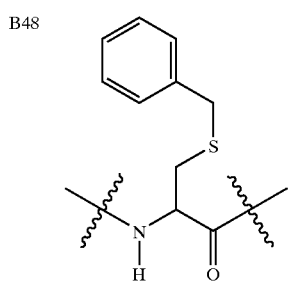 | |
| A49 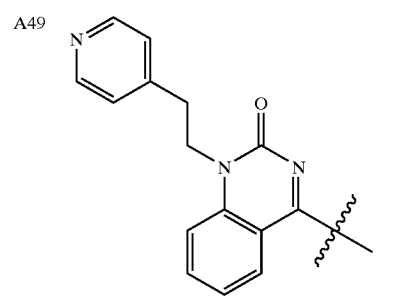 | B49 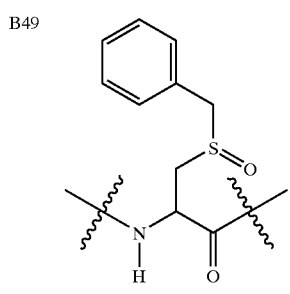 | |

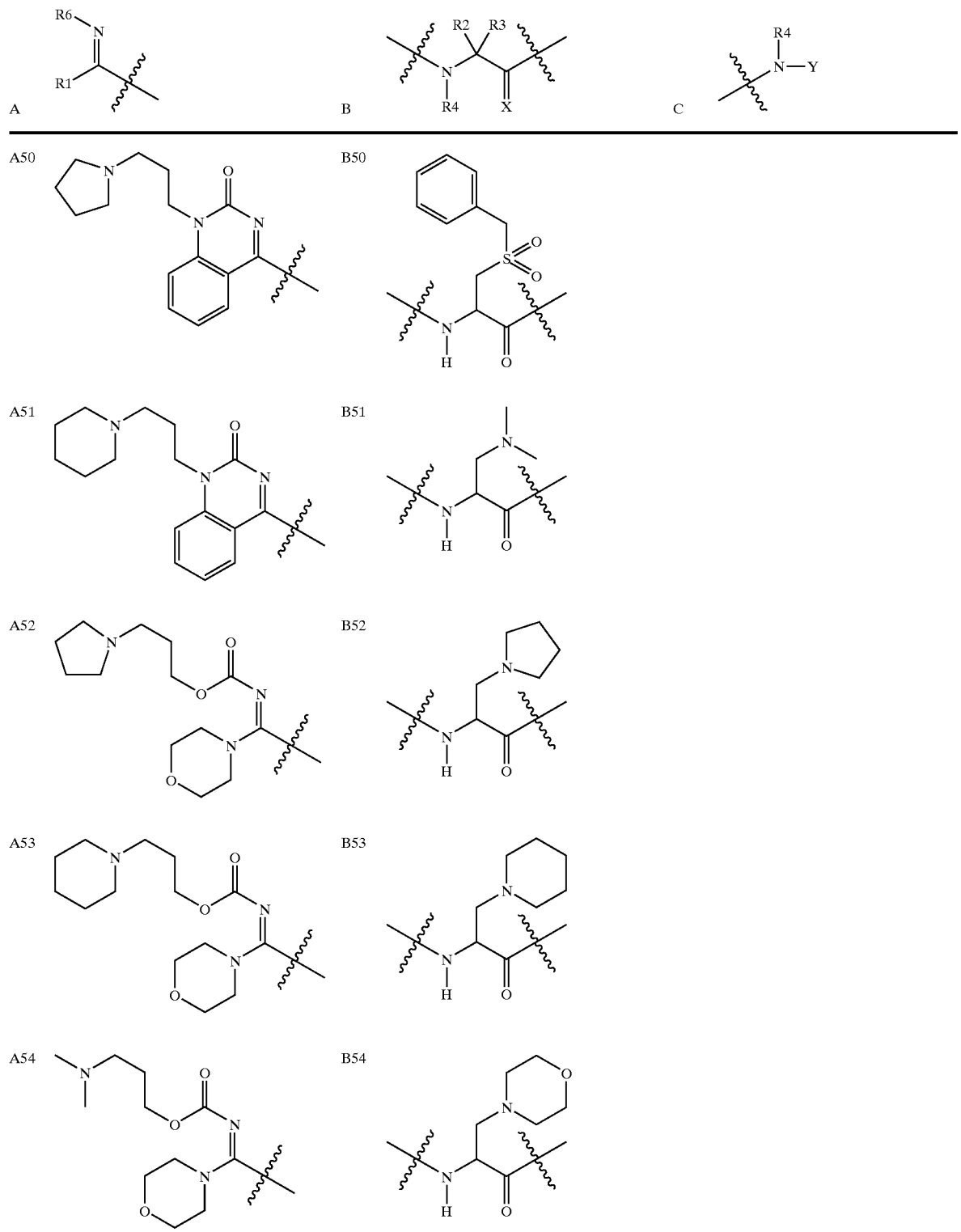

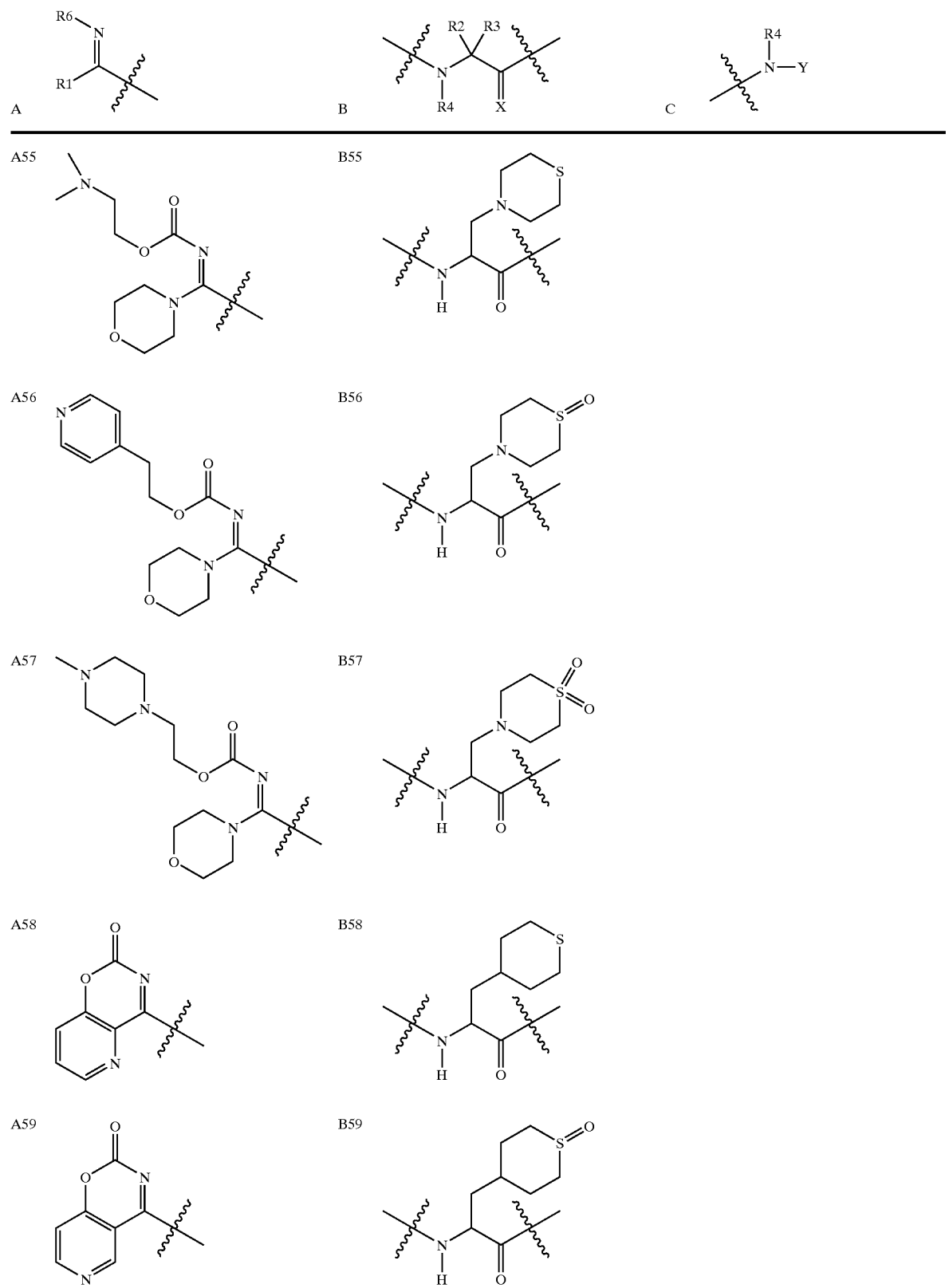

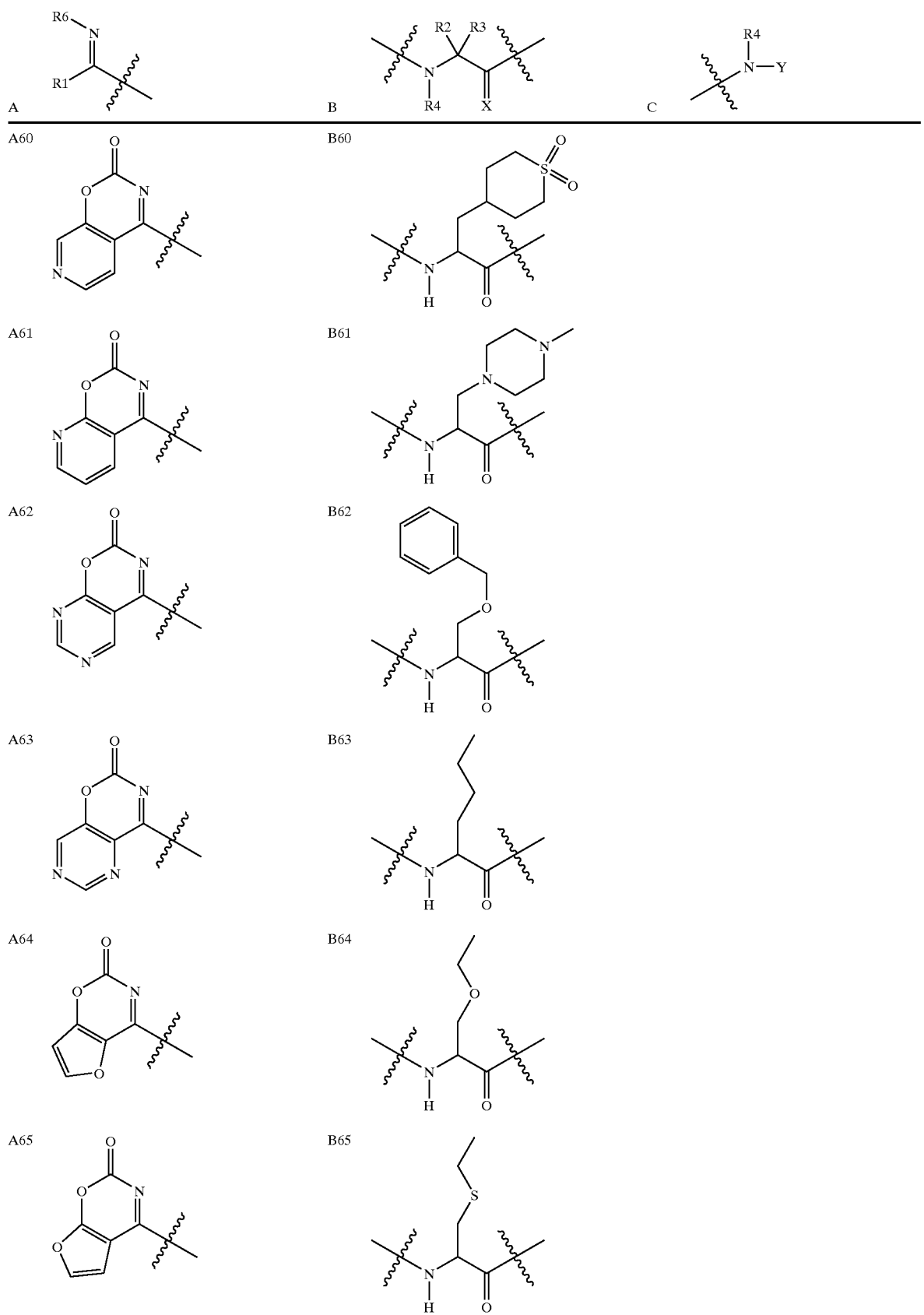

-continued
| A | B | C |
|---|---|---|
| 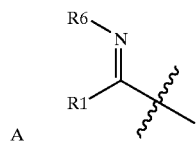 | 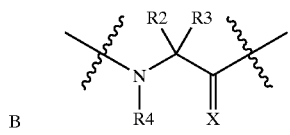 | 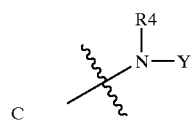 |
| A66 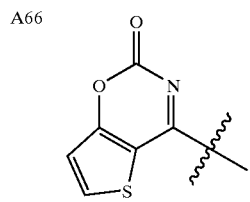 | B66 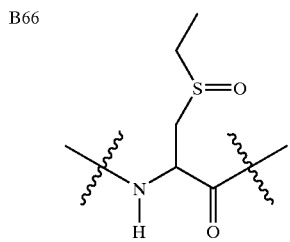 | |
| A67 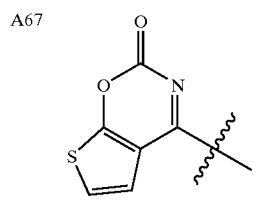 | B67 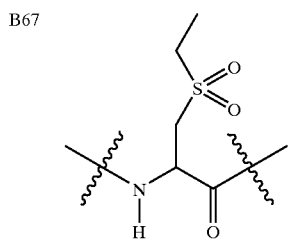 | |
| A68 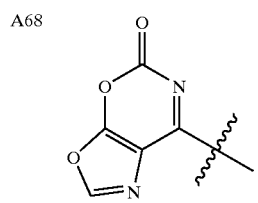 | B68 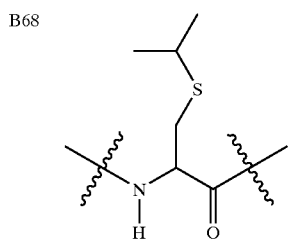 | |
| A69 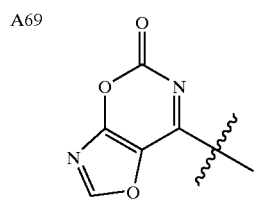 | B69 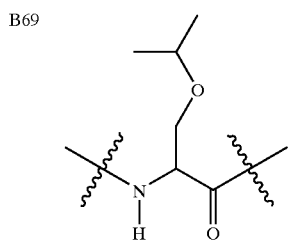 | |
| A70 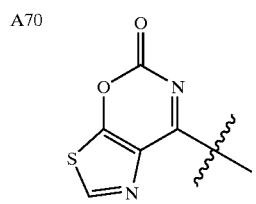 | B70 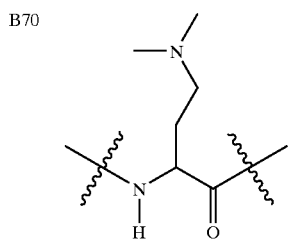 | |

-continued
| A 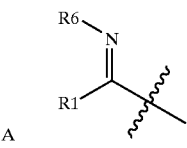 | B 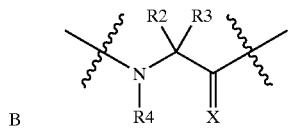 | C 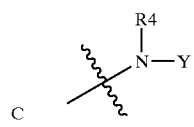 |
|---|---|---|
| A71 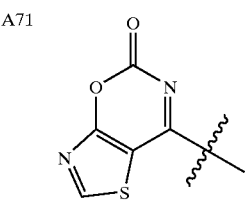 | B71 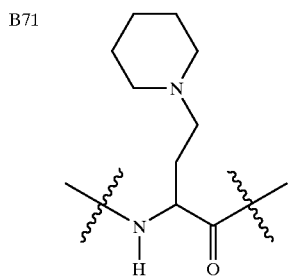 | |
| A72 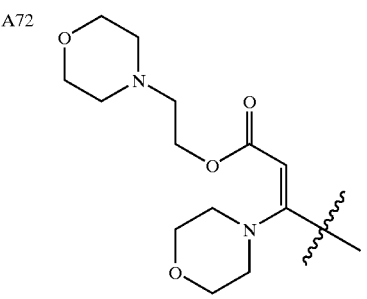 | B72 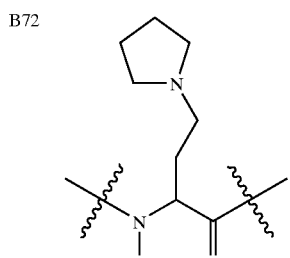 | |
| A73 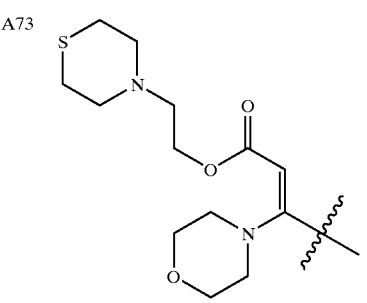 | B73 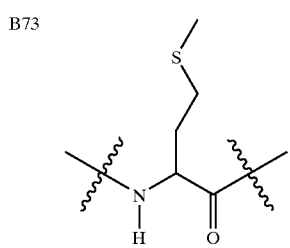 | |
| A74 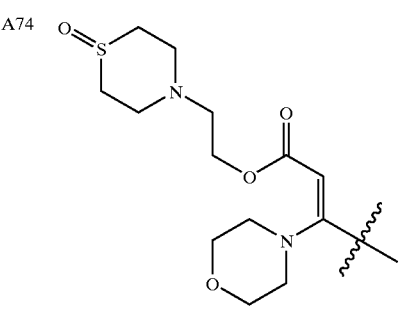 | B74 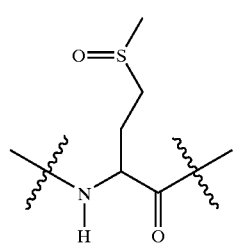 | |

-continued
| A | B | C |
|---|---|---|
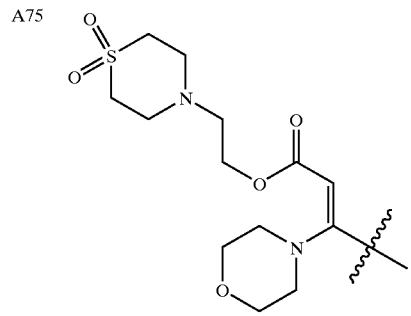 | 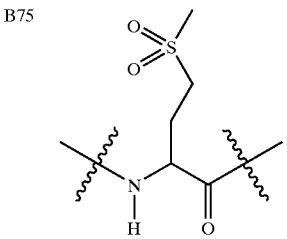 | |
A75 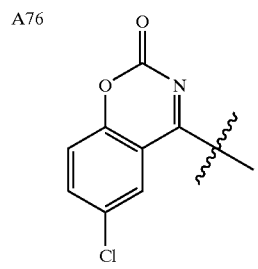 B75 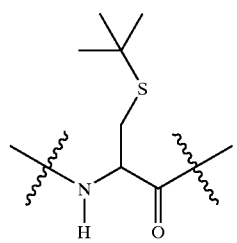
A76 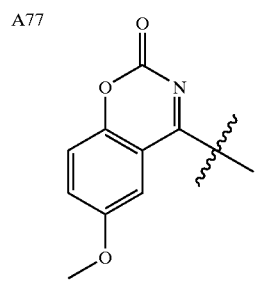 B76 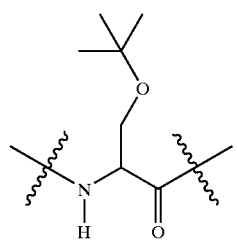
A77 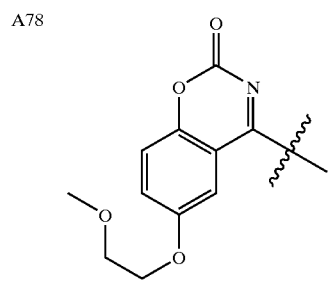 B77 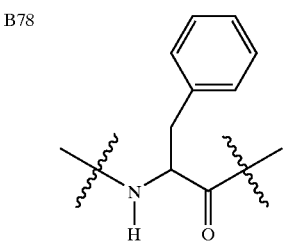
A78 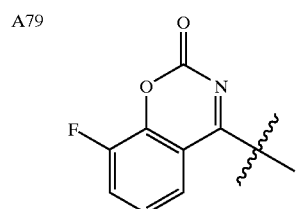 B78 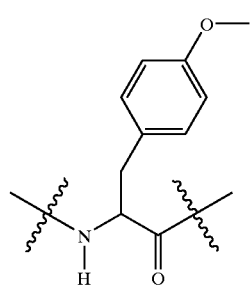
A79 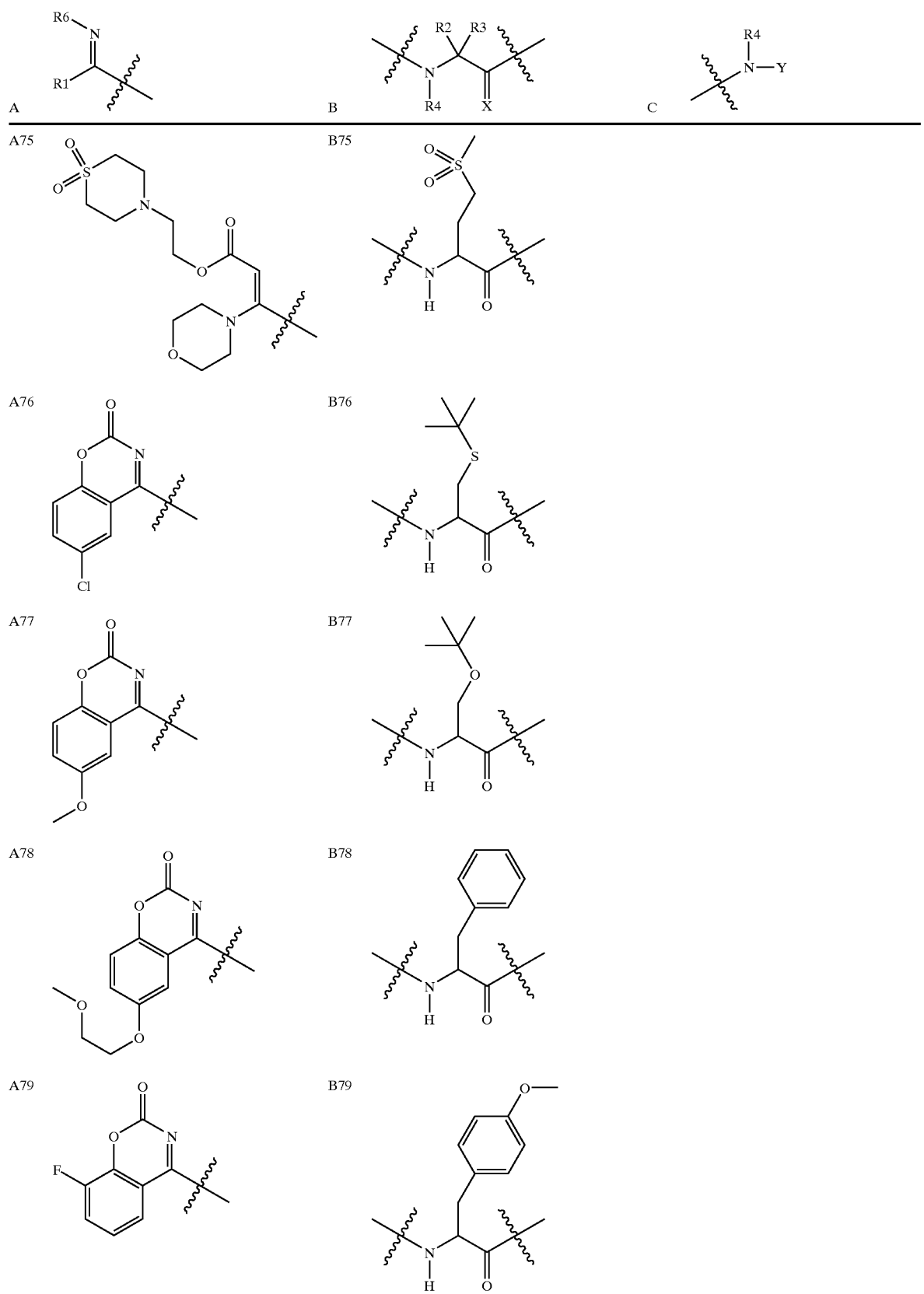

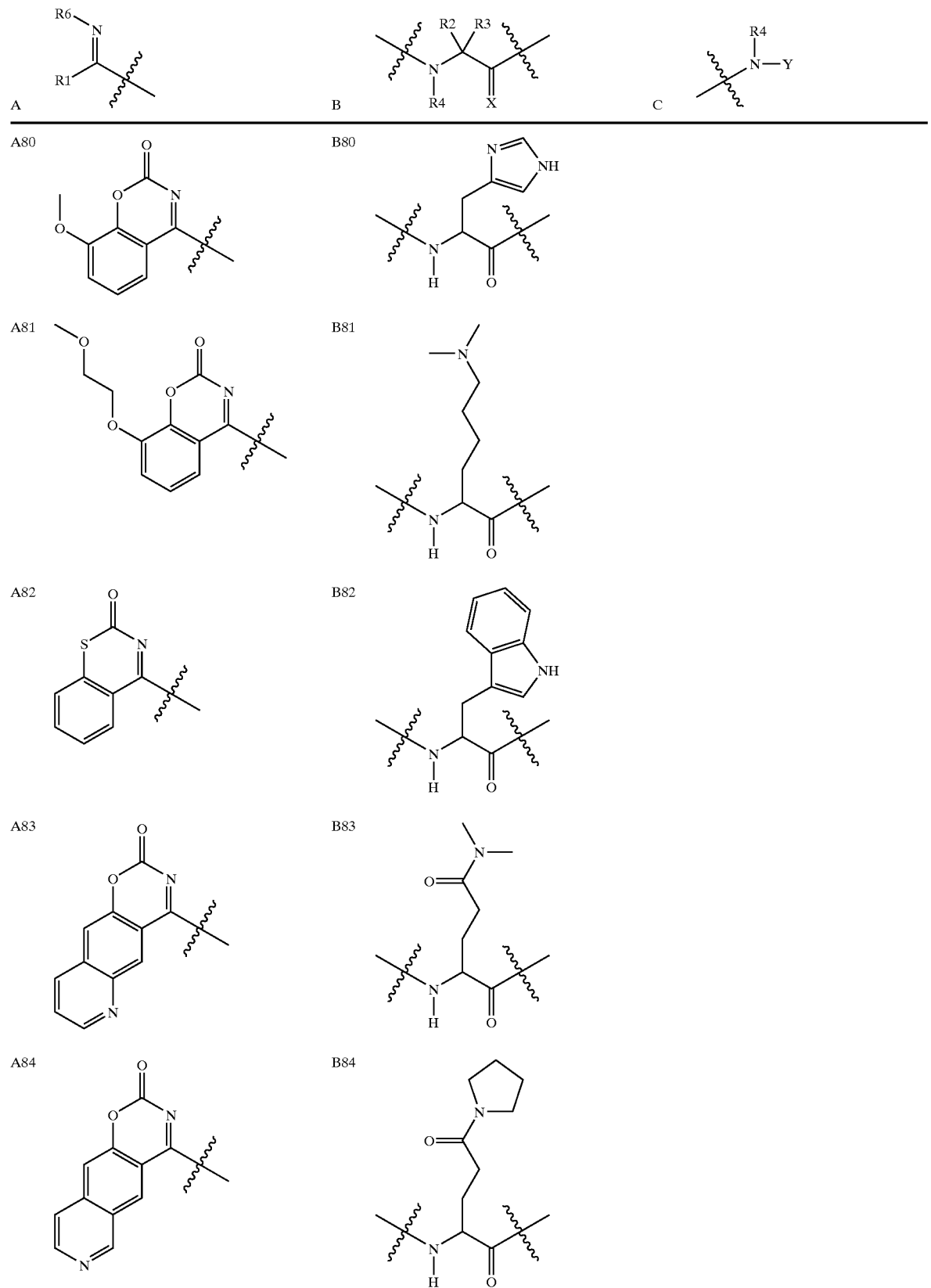

-continued
| A | B | C |
|---|---|---|
| 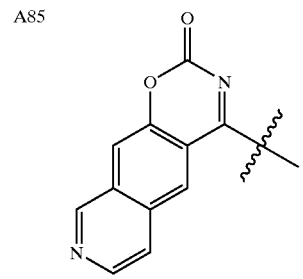 | 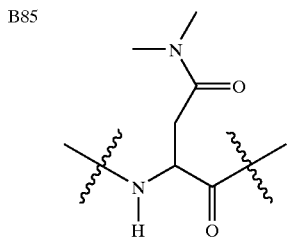 | |
| A85 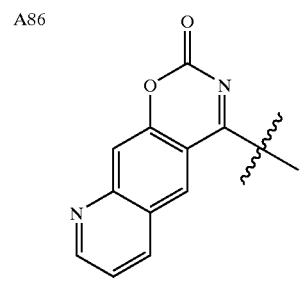 | B85 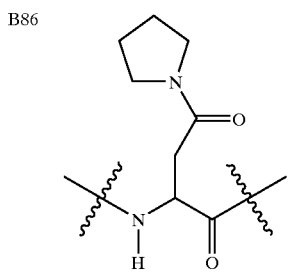 | |
| A86 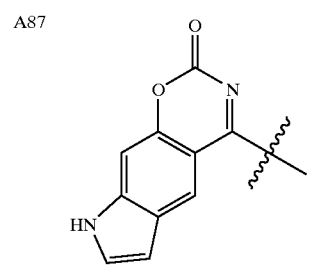 | B86 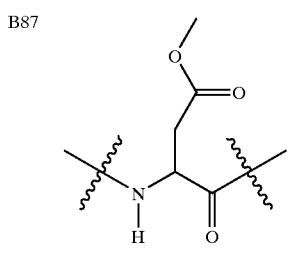 | |
| A87 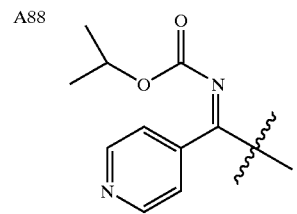 | B87 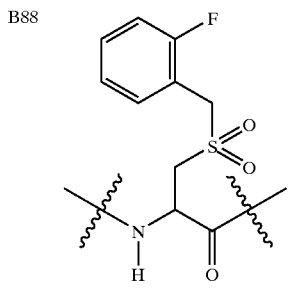 | |
| A88 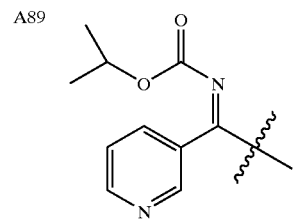 | B88 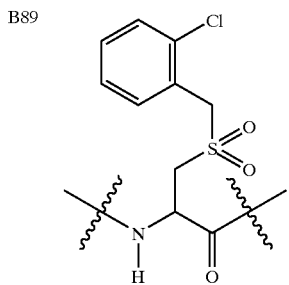 | |
| A89 | B89 | |

-continued
| A | B | C |
|---|---|---|
| 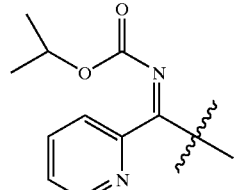 | 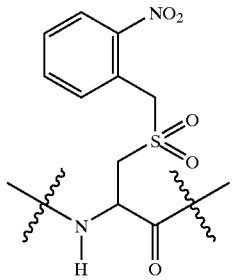 | |
| A90 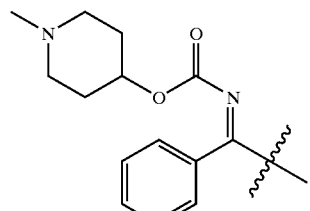 | B90 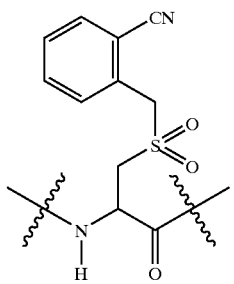 |
| A91 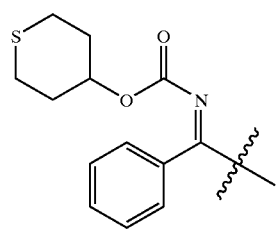 | B91 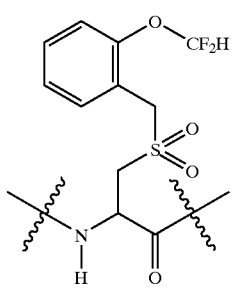 |
| A92 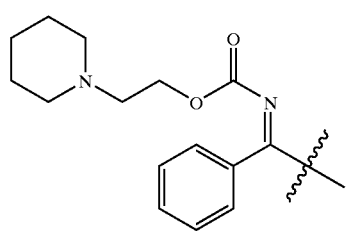 | B92 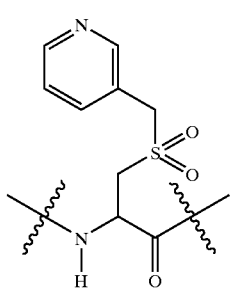 |
| A93 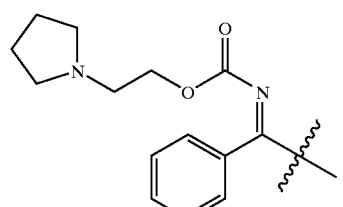 | B93 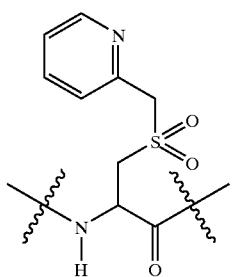 |
| A94 | B94 |
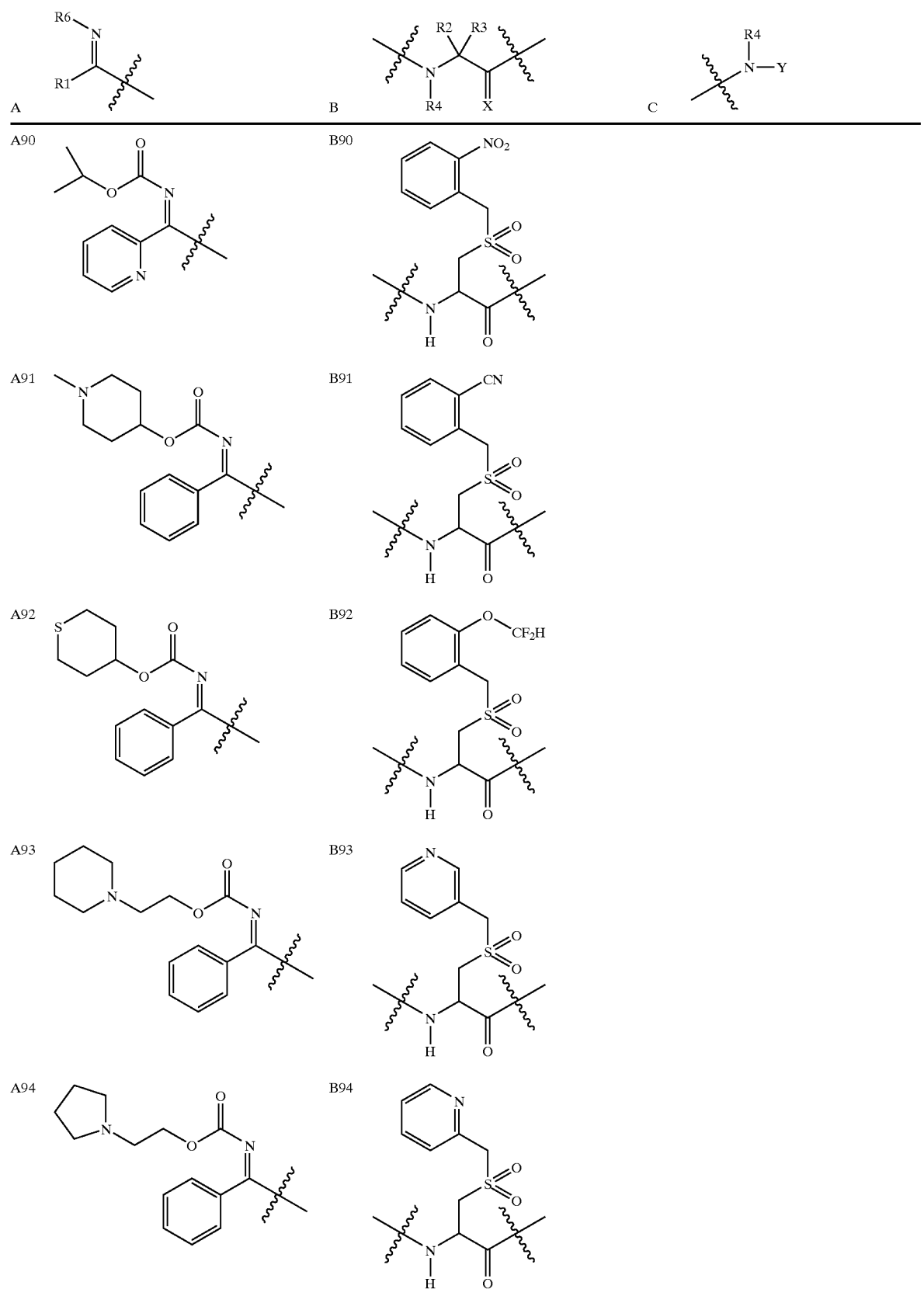

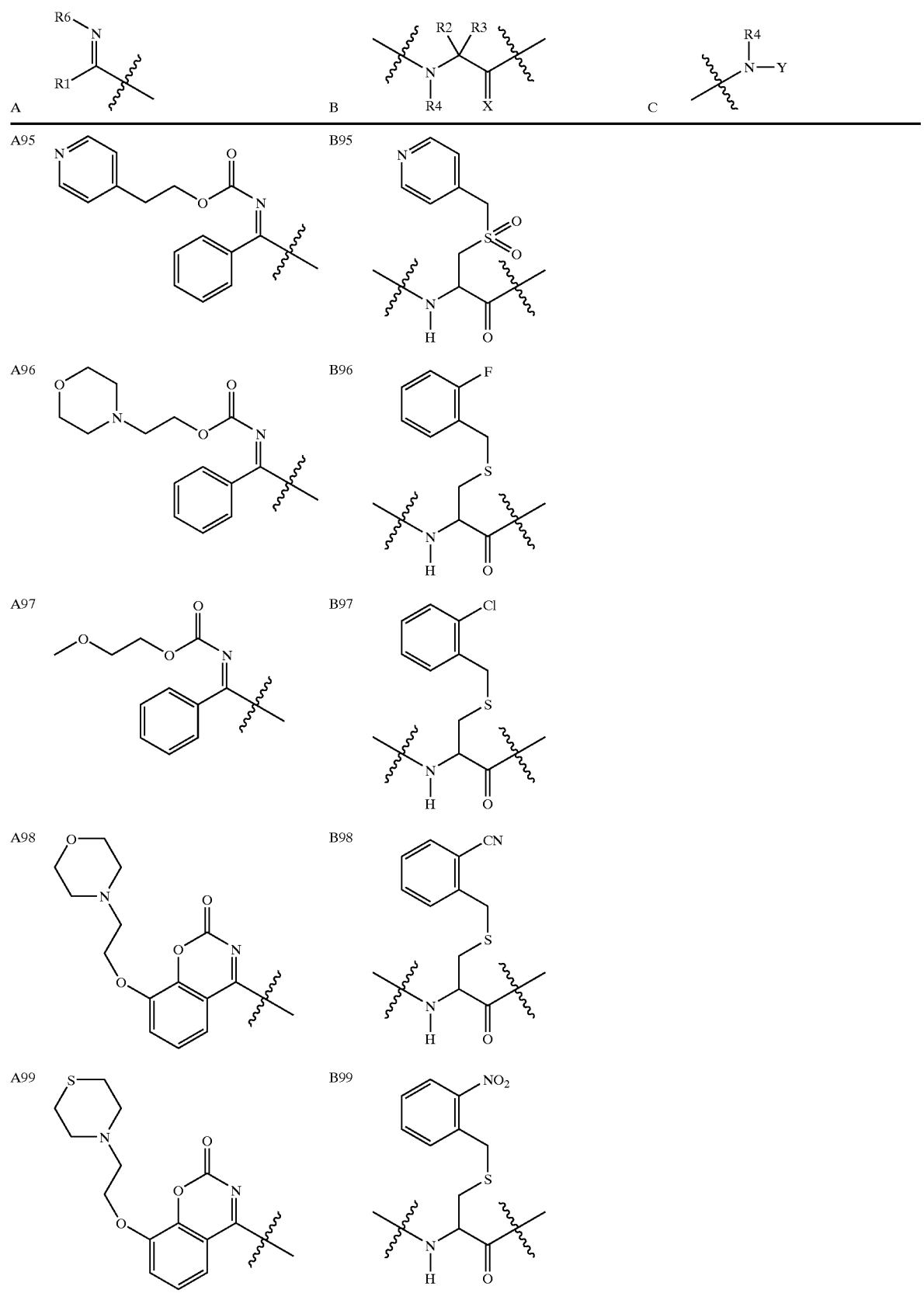

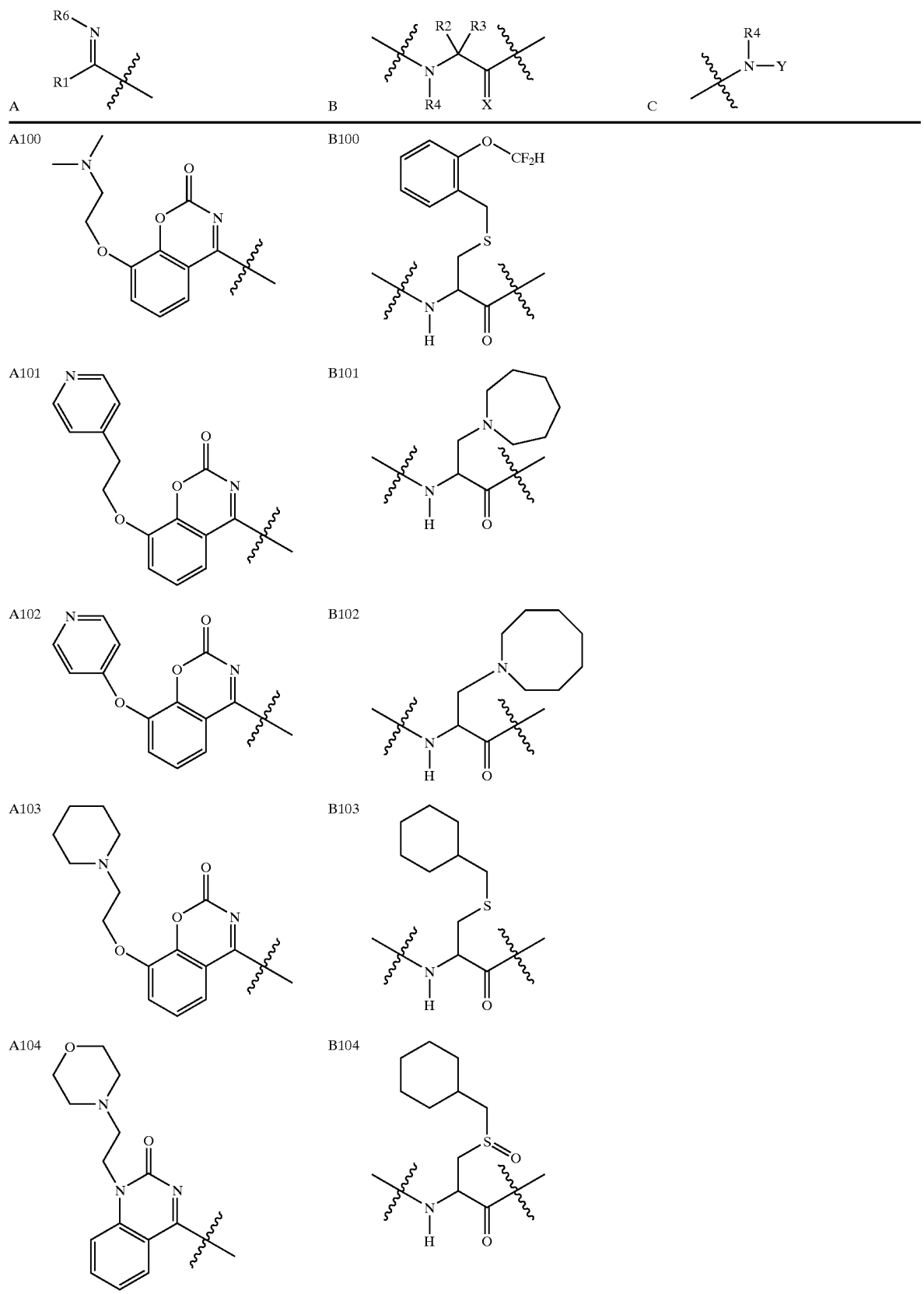

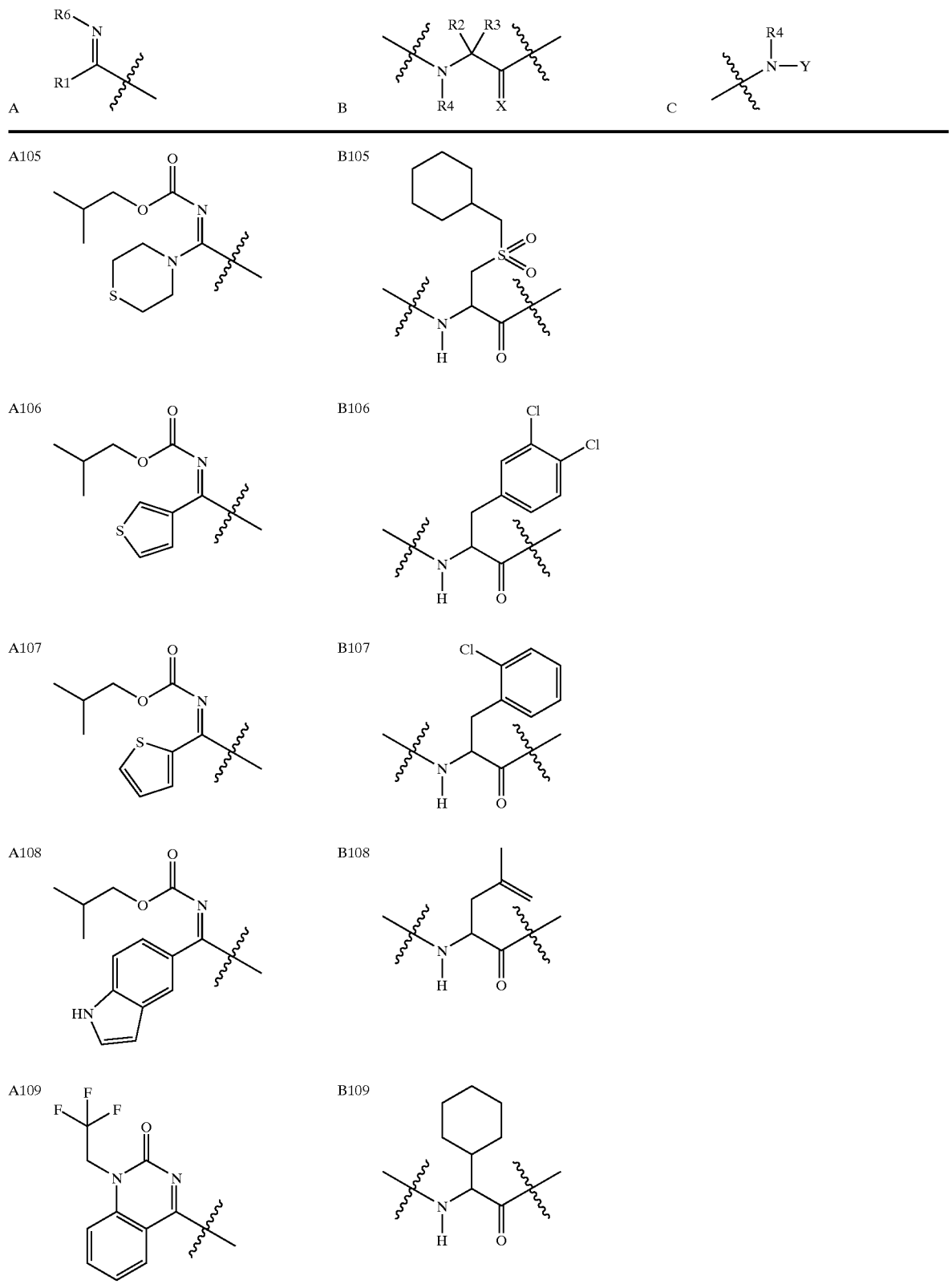

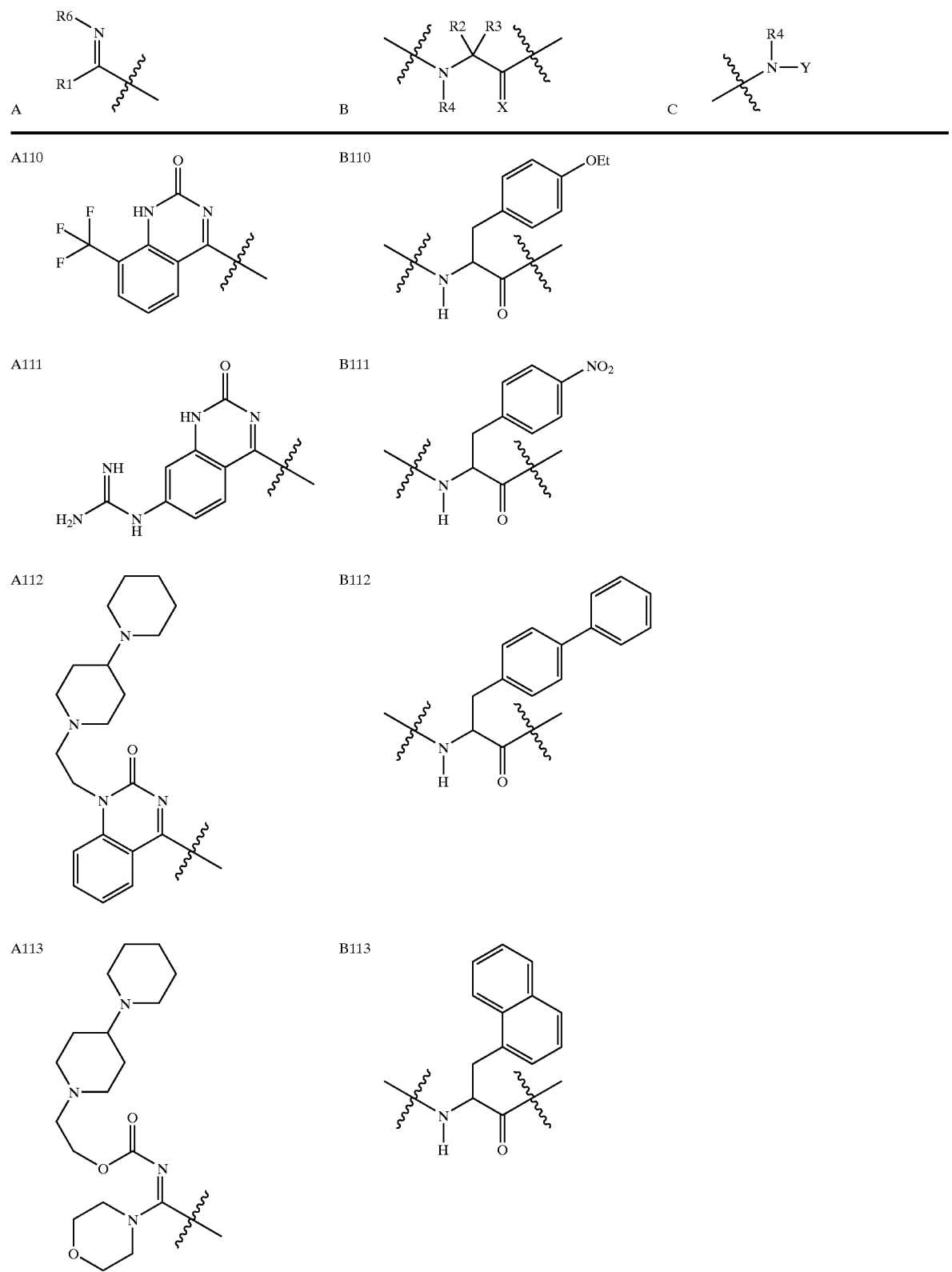

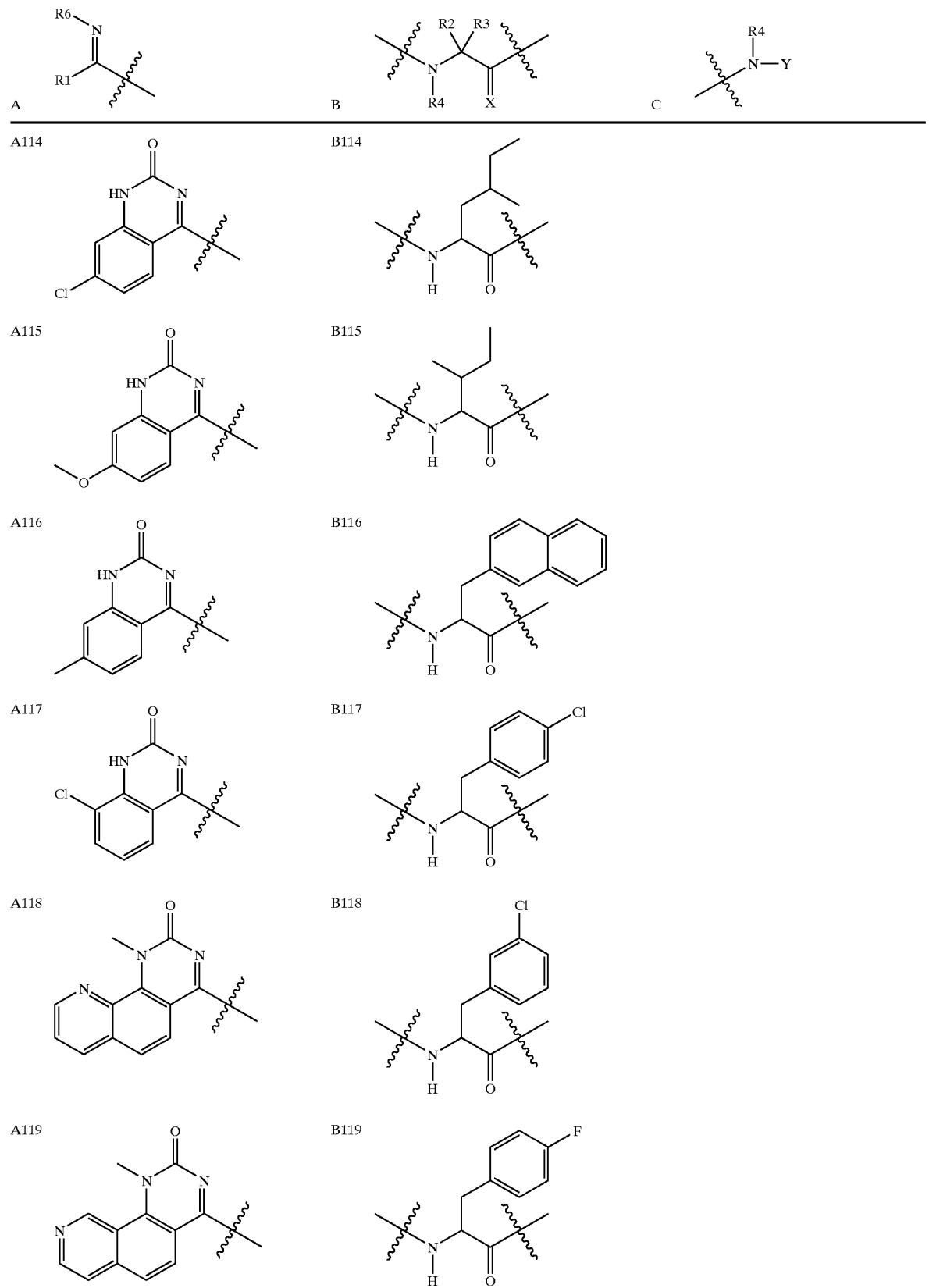

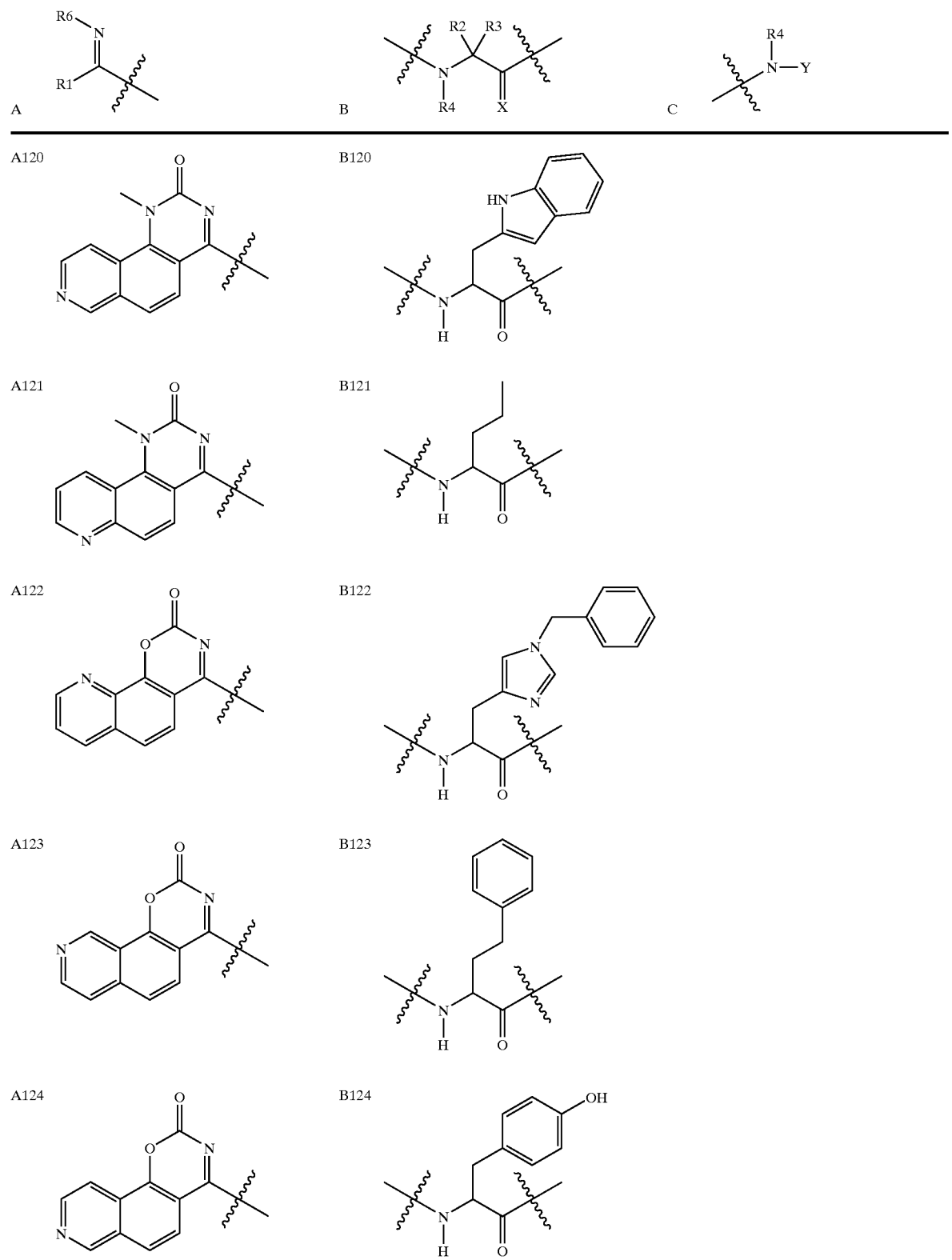

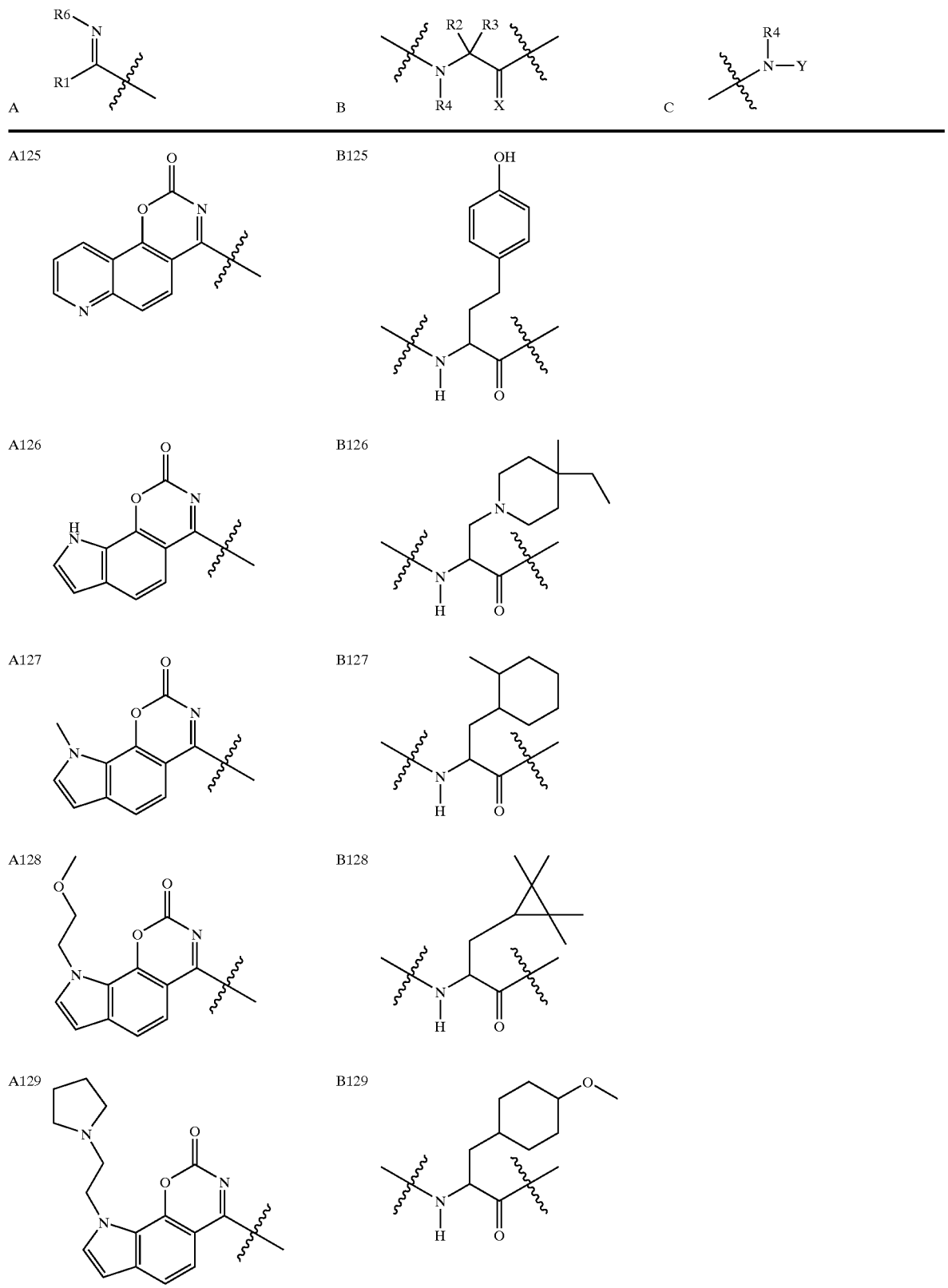

-continued
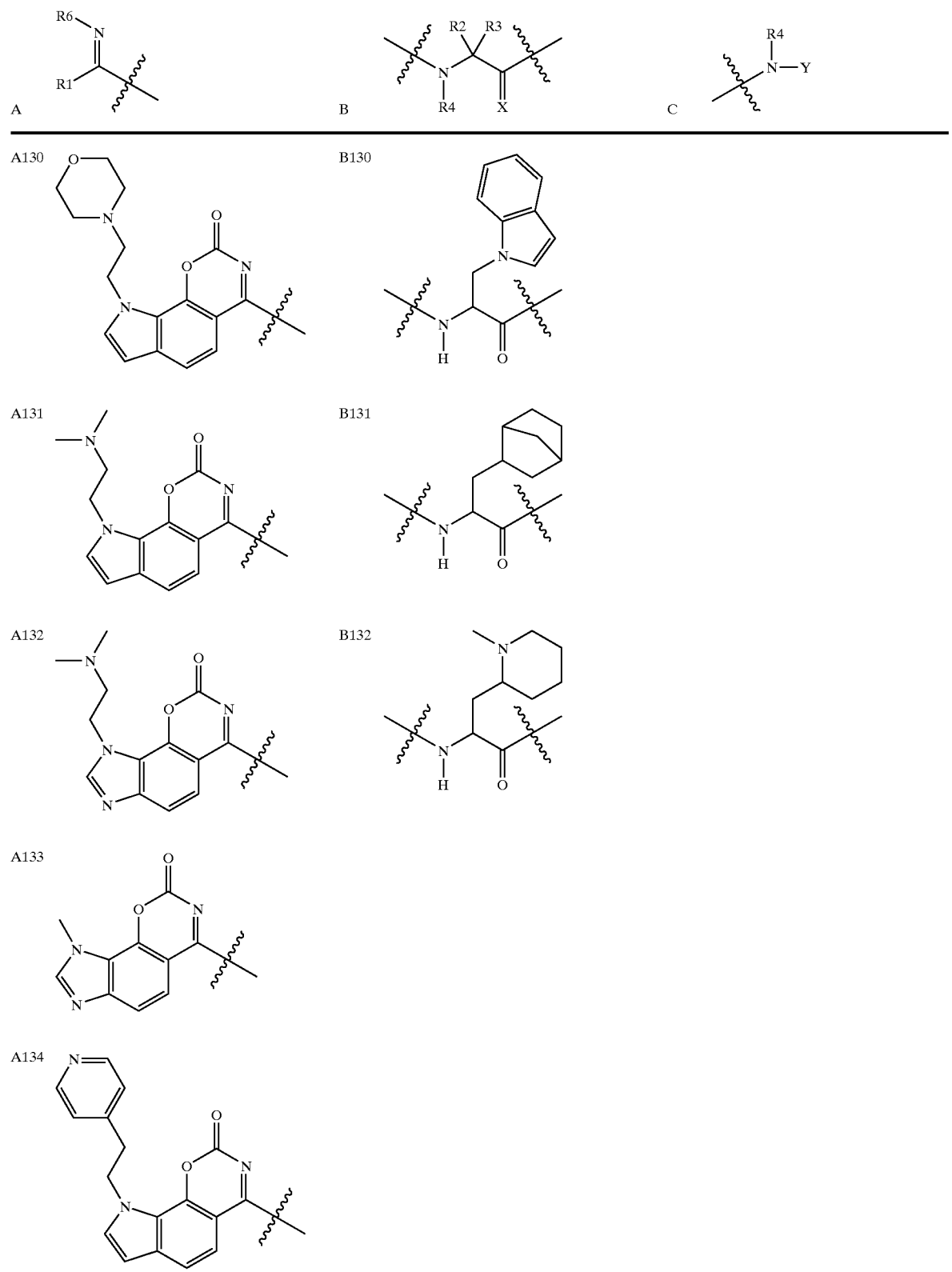

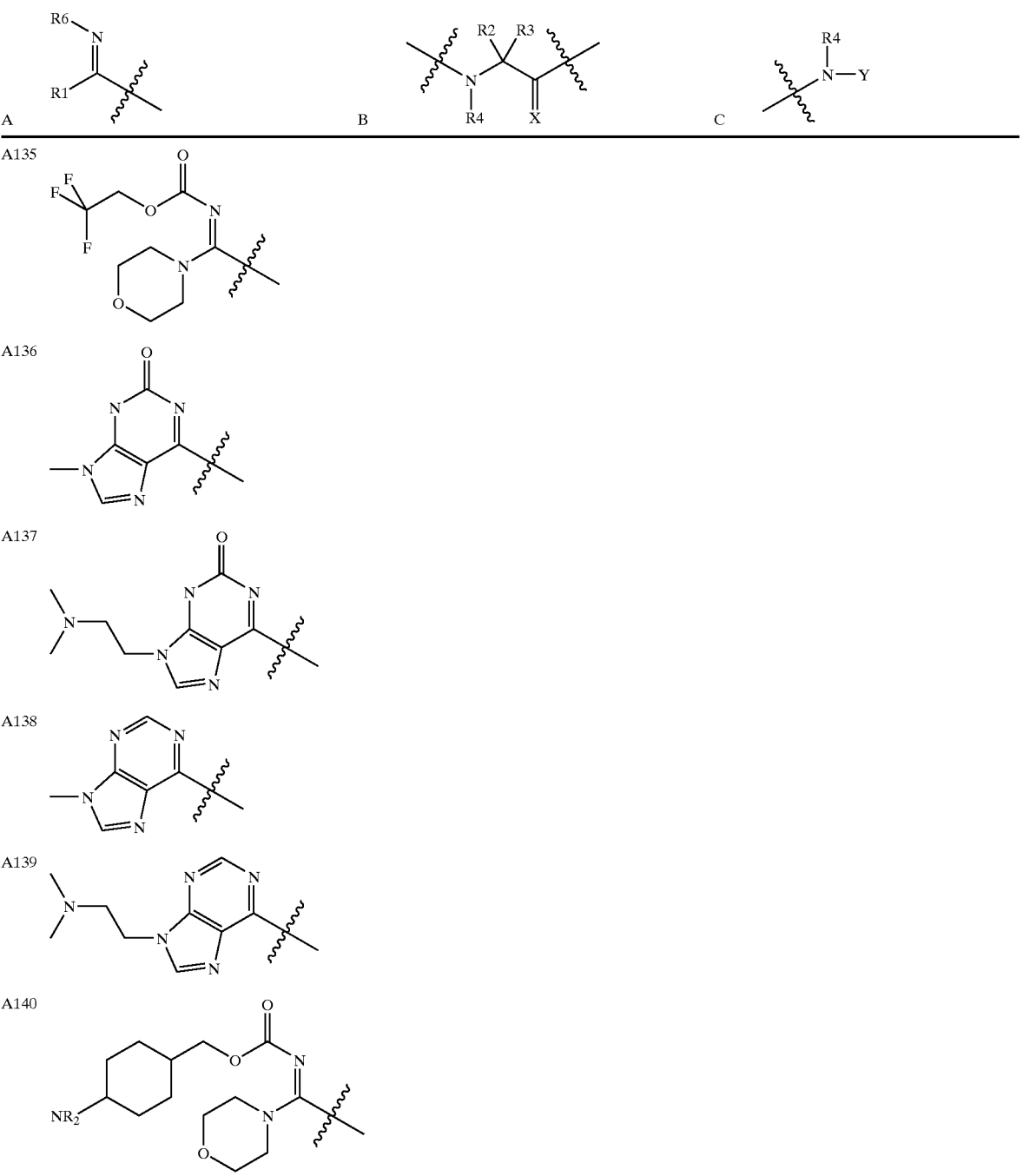

or the pharmaceutically acceptable salts, esters, isomers or tautomers thereof.

15. The compound according to claim 1 and wherein:
$R_1$ is a bond, C1–4 alkyl, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;
$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, $C_{1-2}$ alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one or more $R_c$;

$R_c$ is methyl, ethyl, cyclohexyl, cyclopentyl, phenyl, naphthyl, bicyclo[3.1.0]hexanyl, bicyclo[1.1.1] pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, or $R_c$ is phenoxycarbonylamino, phenylcarbamoyloxy, phenylsulfonylamino, phenylaminosulfonyl, amino wherein the nitrogen atom may be independently mono or di-substituted by methyl or phenyl, or $R_c$ is chloro, fluoro, hydroxy, oxo, carboxy or cyano;

or $R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is C1–7 alkyl or C1–7 acyl each optionally substituted by C1–5 alkoxy, phenyloxy, benzyloxy, hydroxy, carboxy, phenyl, benzyl, heterocyclyl chosen from piperidinyl, morpholinyl, thiomorpholinyl and piperazinyl or amino wherein the N atom is optionally mono- di-substituted by C1–5 alkyl, phenyl or benzyl, or $R_5$ is carboxy.

16. The compound according to claim 15 wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino;

wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, or Re is acetylamino, benzoylamino, methylthio, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is C1–5 alkyl or C1–5 acyl each optionally substituted by C1–3 alkoxy, phenyloxy, benzyloxy, hydroxy, carboxy, phenyl, benzyl, heterocyclyl chosen from morpholinyl and thiomorpholinyl or amino wherein the N atom is optionally mono- di-substituted by C1–3 alkyl, phenyl or benzyl, or $R_5$ is carboxy.

17. The compound according to claim 16 wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino;

wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl; and R₅ is C1–3 alkyl or C1–-3 acyl each optionally substituted by C1–3 alkoxy, phenyloxy, benzyloxy, hydroxy, carboxy, phenyl, benzyl, morpholinyl or amino wherein the N atom is optionally mono- di-substituted by C1–3 alkyl, phenyl or benzyl, or R₅ is carboxy.

18. The compound according to claim 17 wherein:

R₁ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

R₃ is n-propyl, i-butyl, propenyl, i-butenyl or 2,2-dimethylpropyl; and

R₂ and R₃ together with the carbon they are attached optionally form a ring selected from cyclopentyl, cyclohexyl, or cycloheptyl.

19. A compound of the formula (Ia)

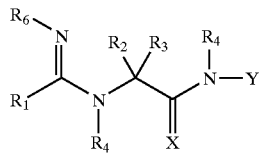

(Ia)

wherein for the Formula (Ia), the components

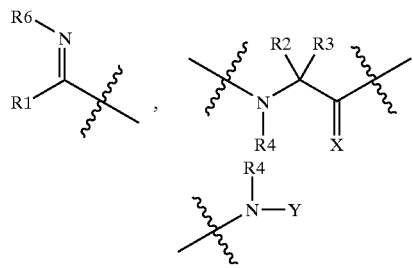

and are chosen from any combination of A, B and C as follows:

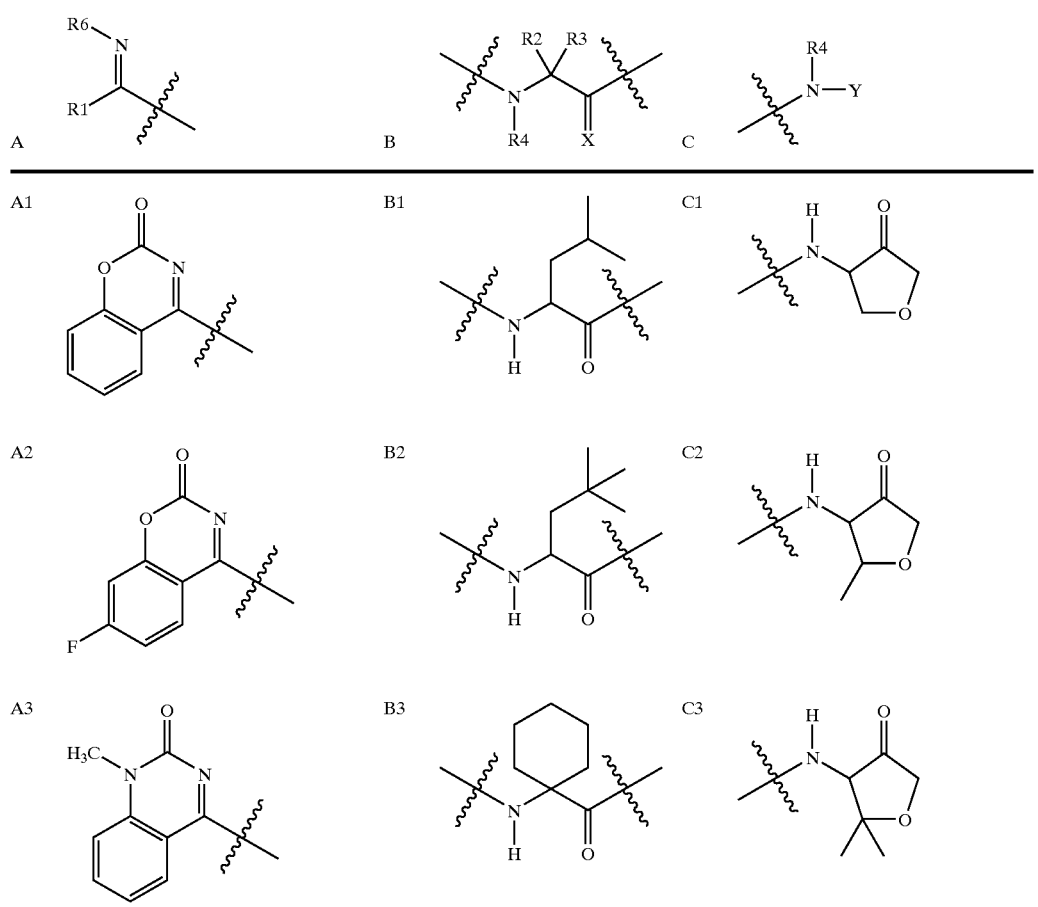

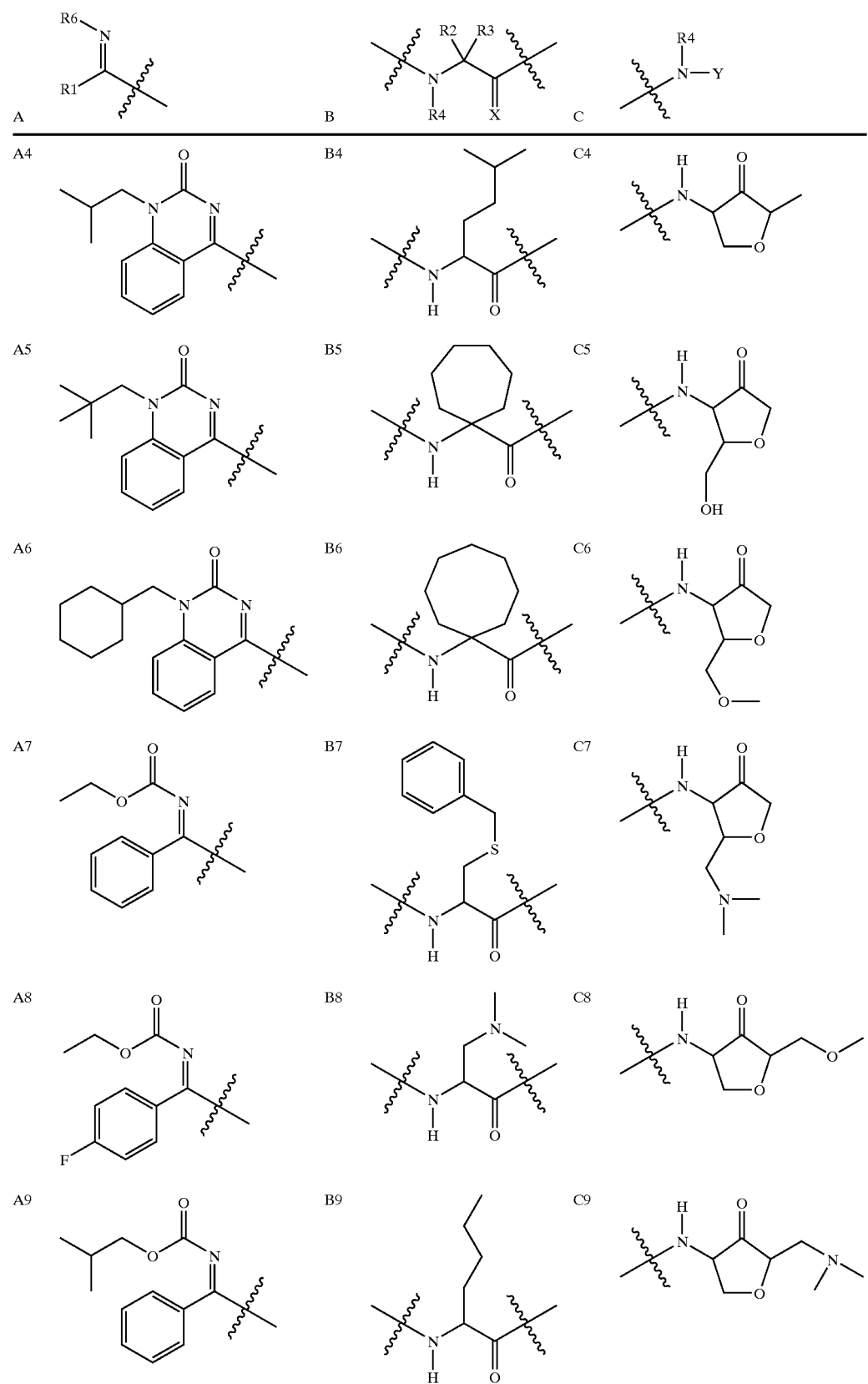

-continued
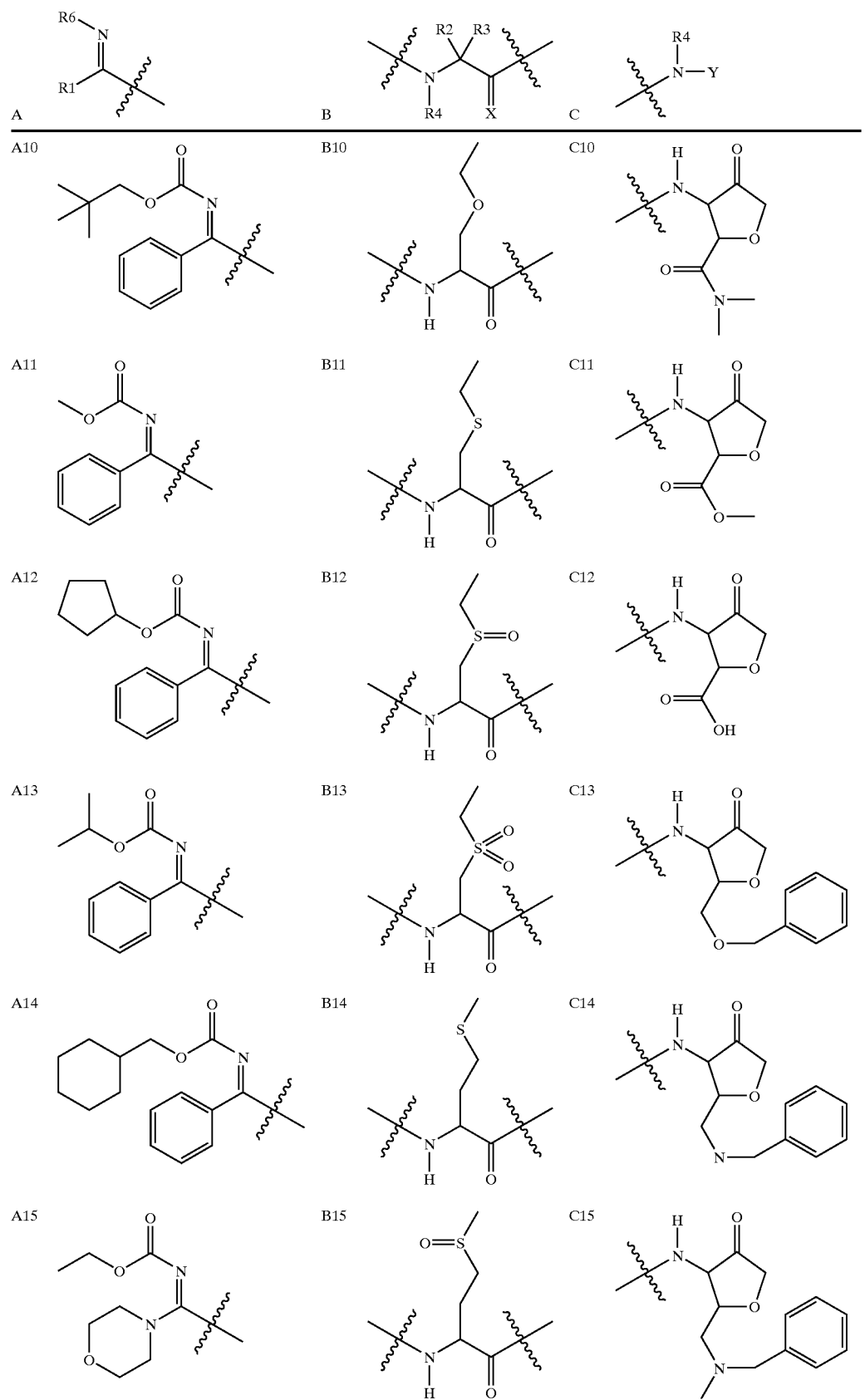

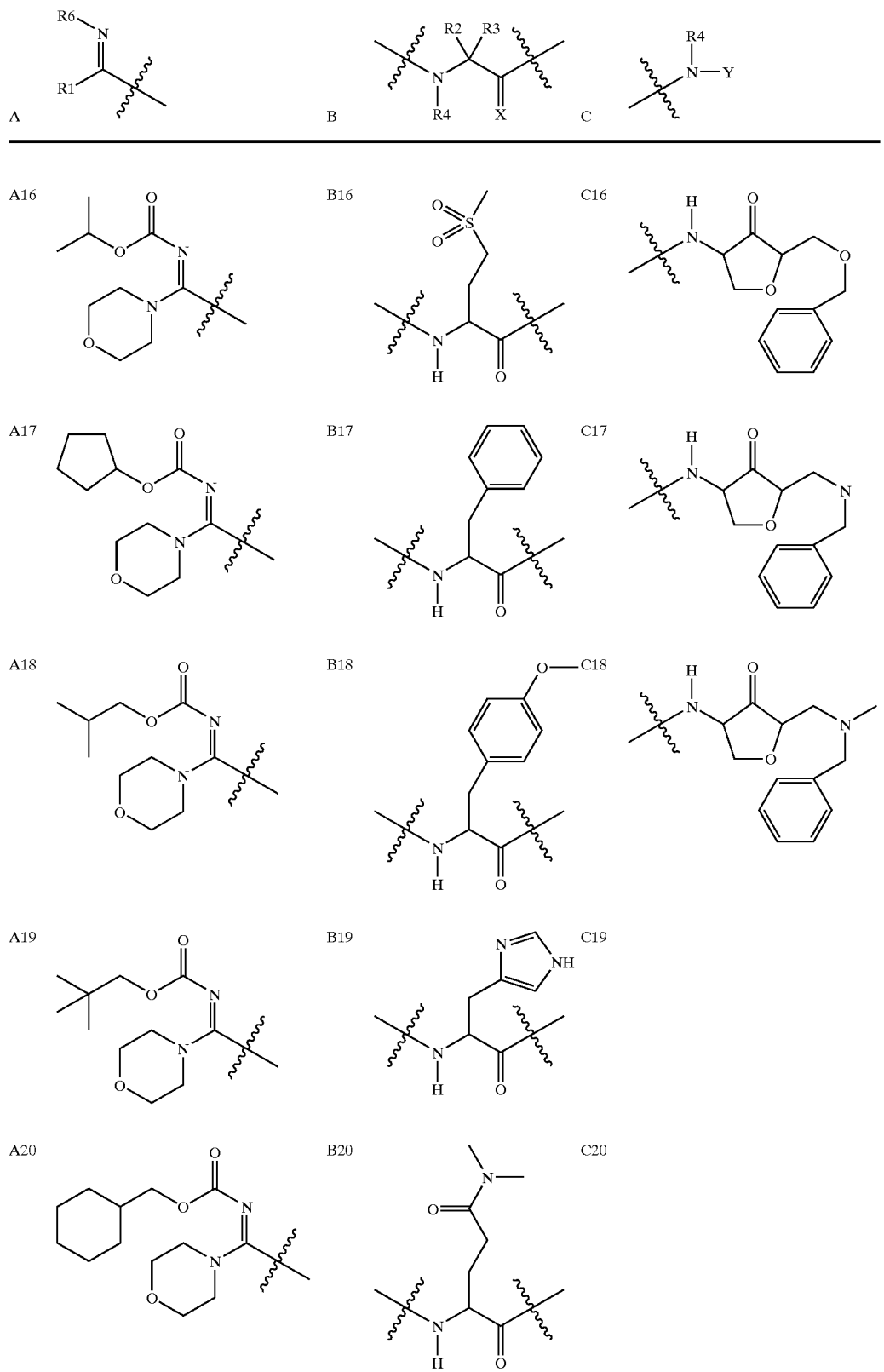

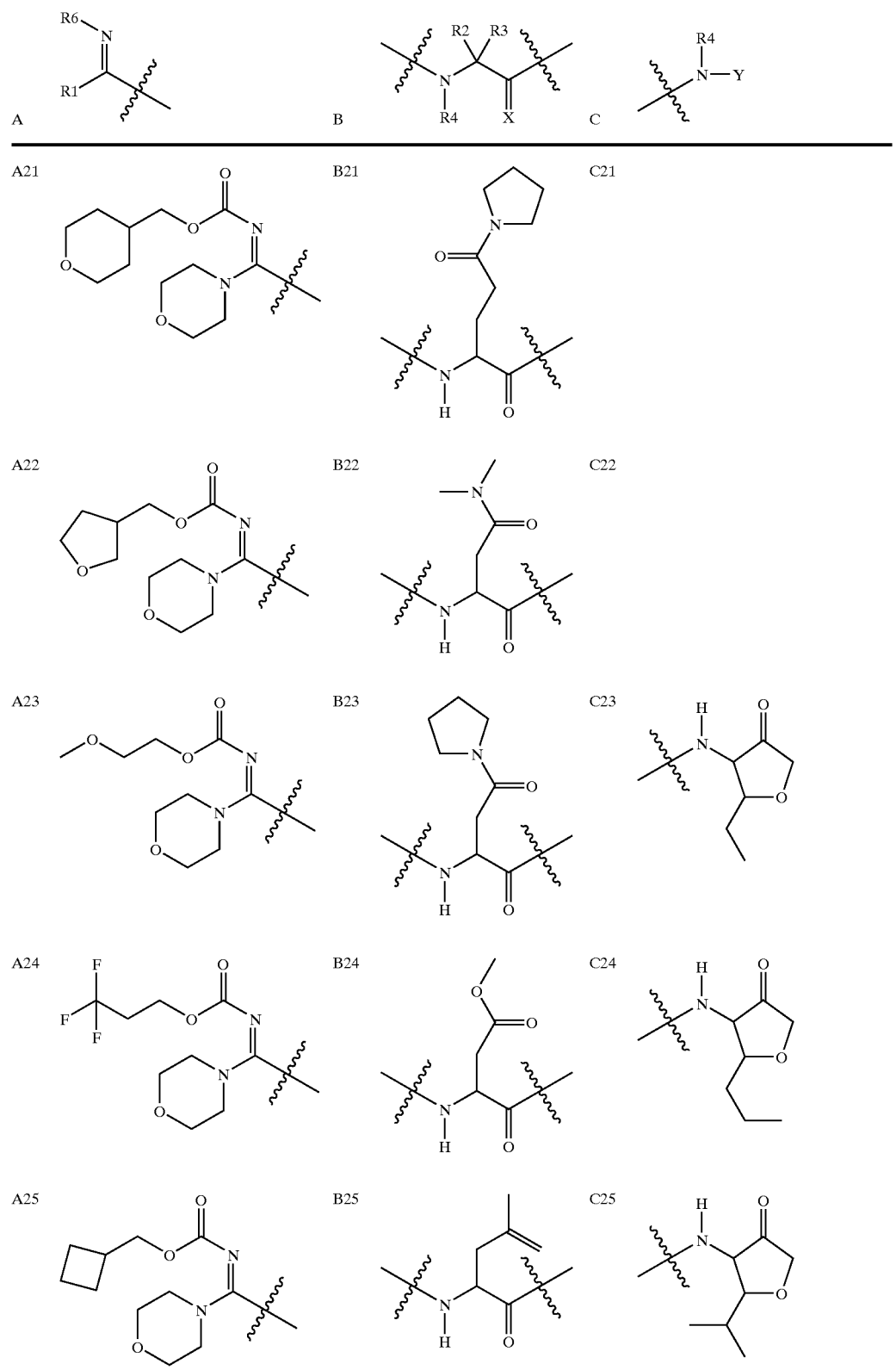

-continued
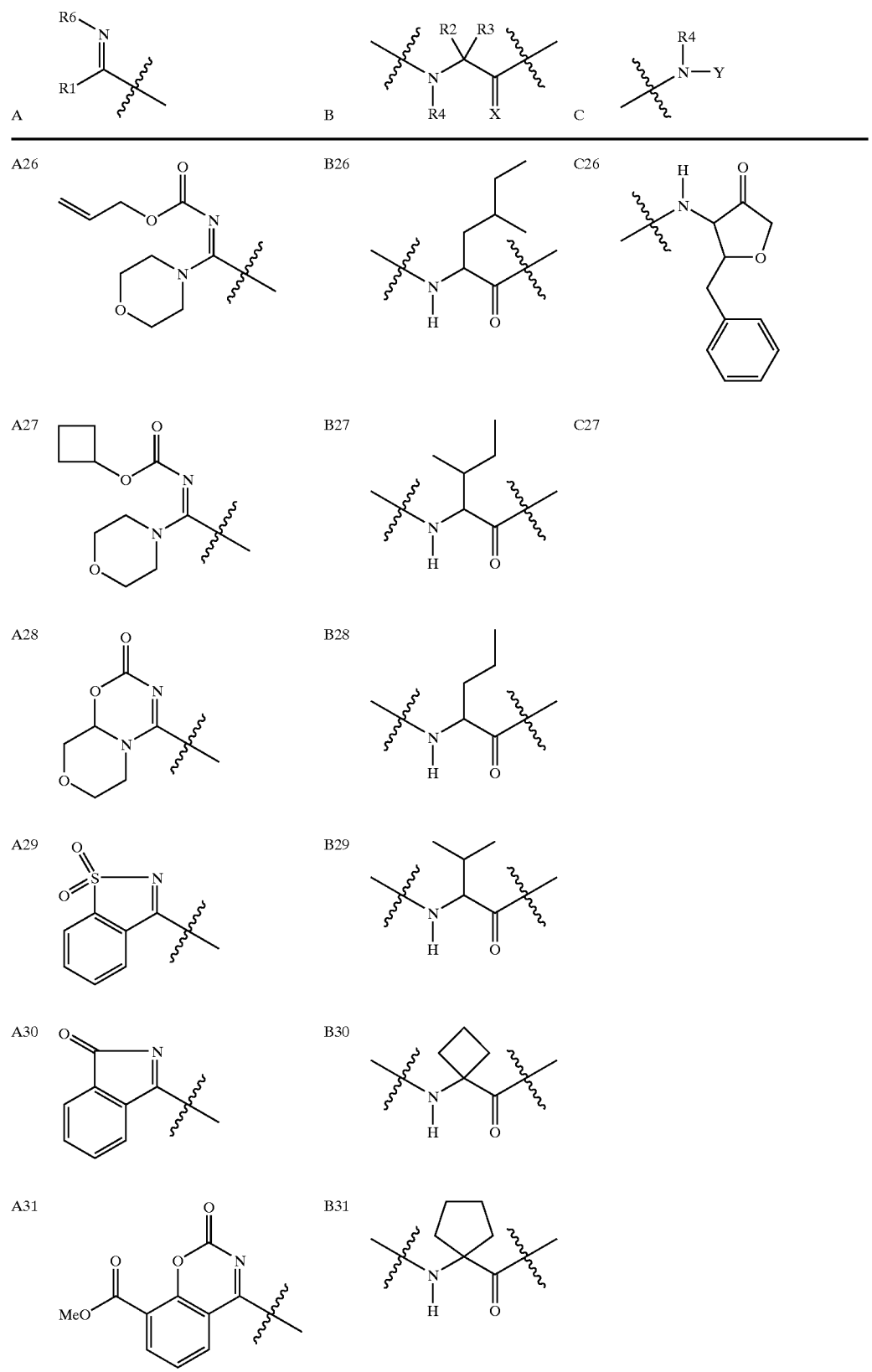

-continued
| A | B | C |
|---|---|---|
| 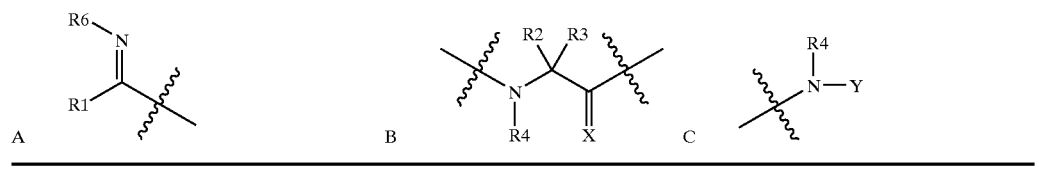 | | |
A32 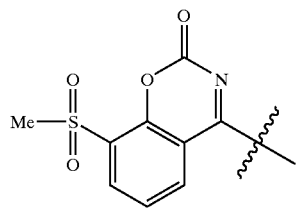
A33 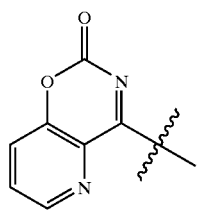
A34 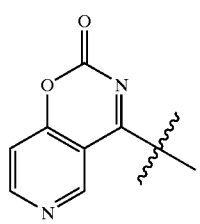
A35 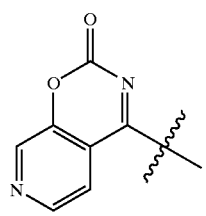
A36 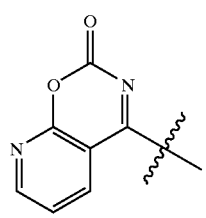
A37 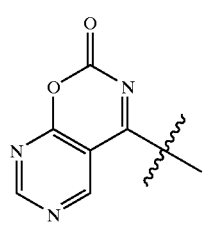

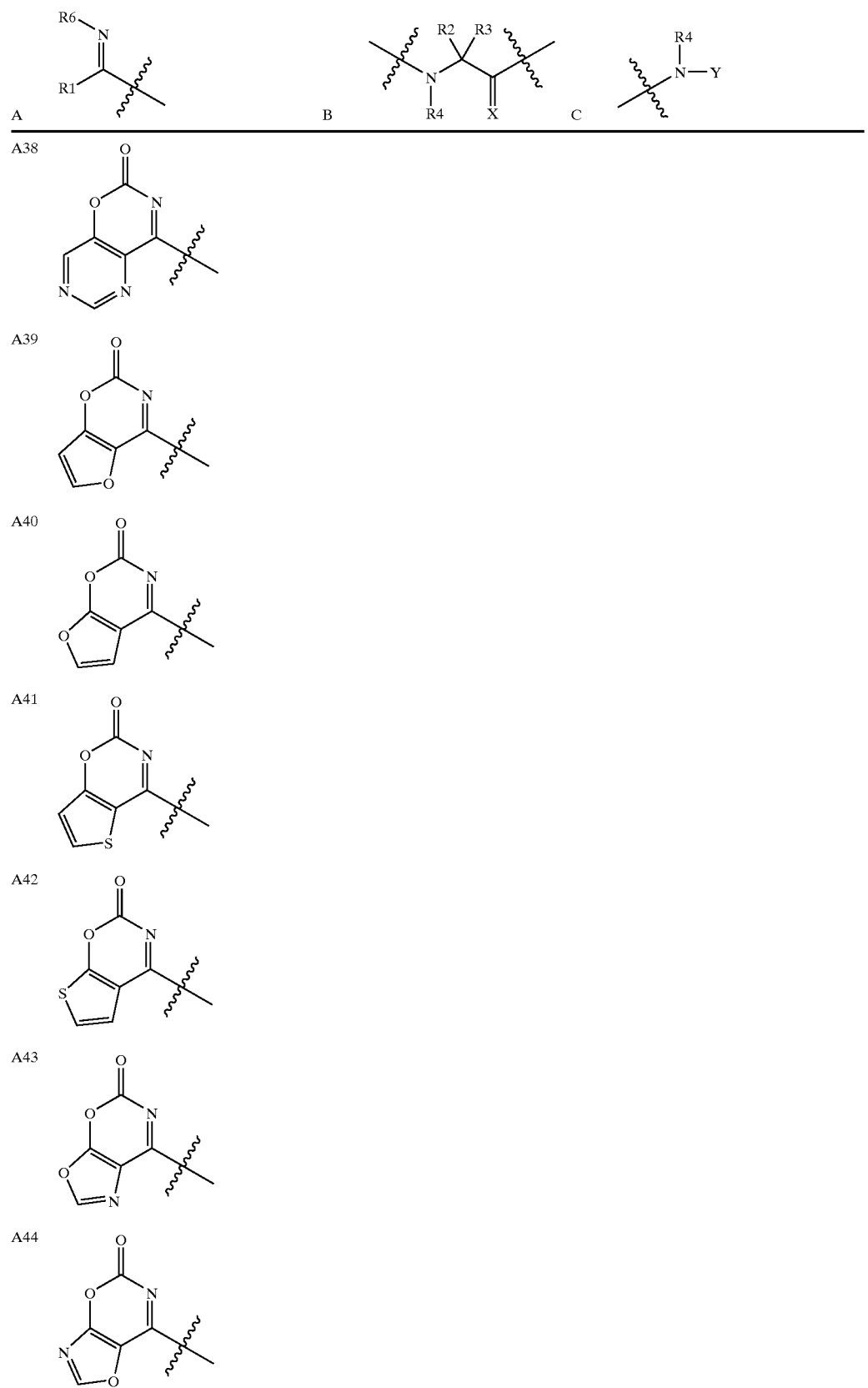

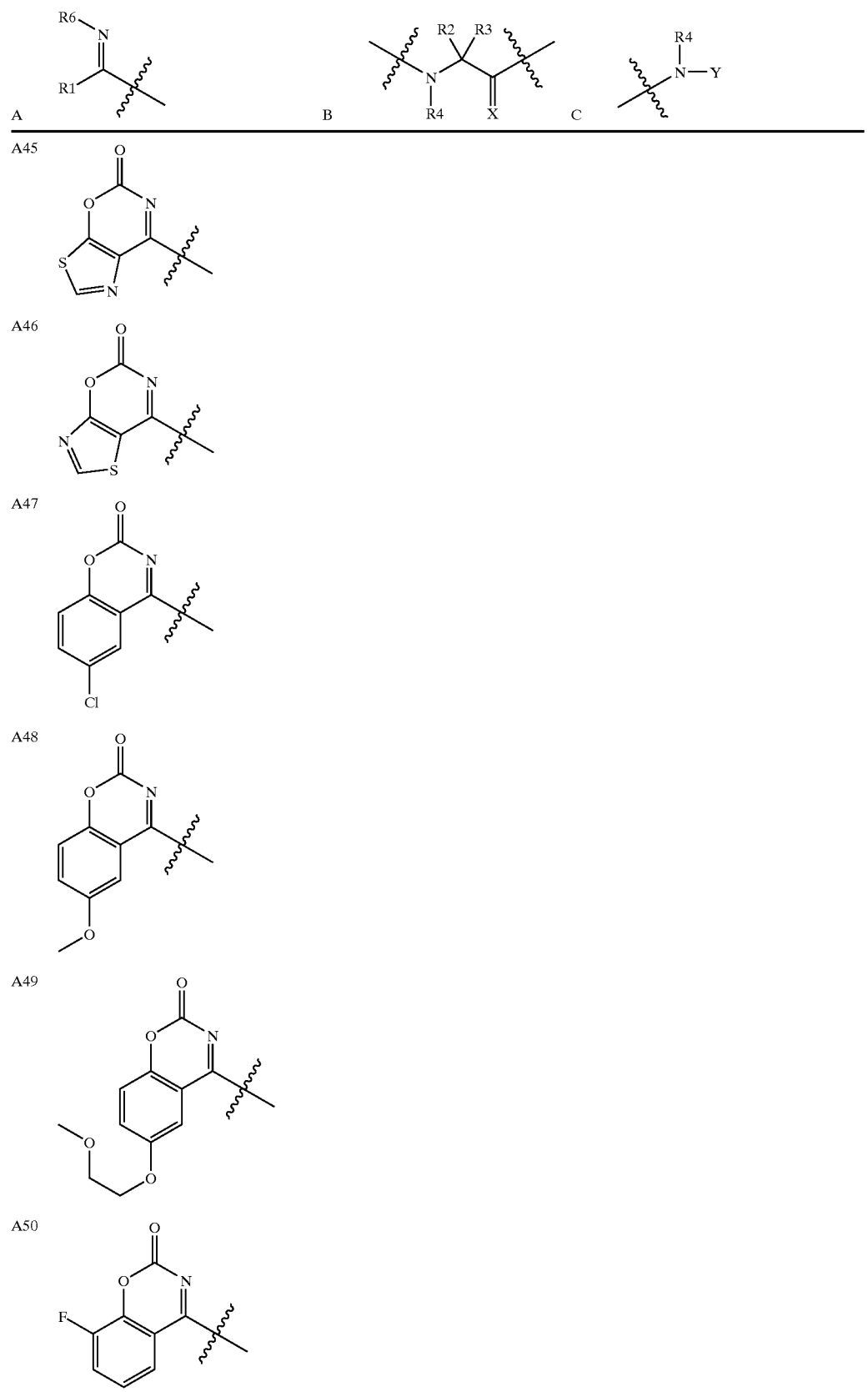

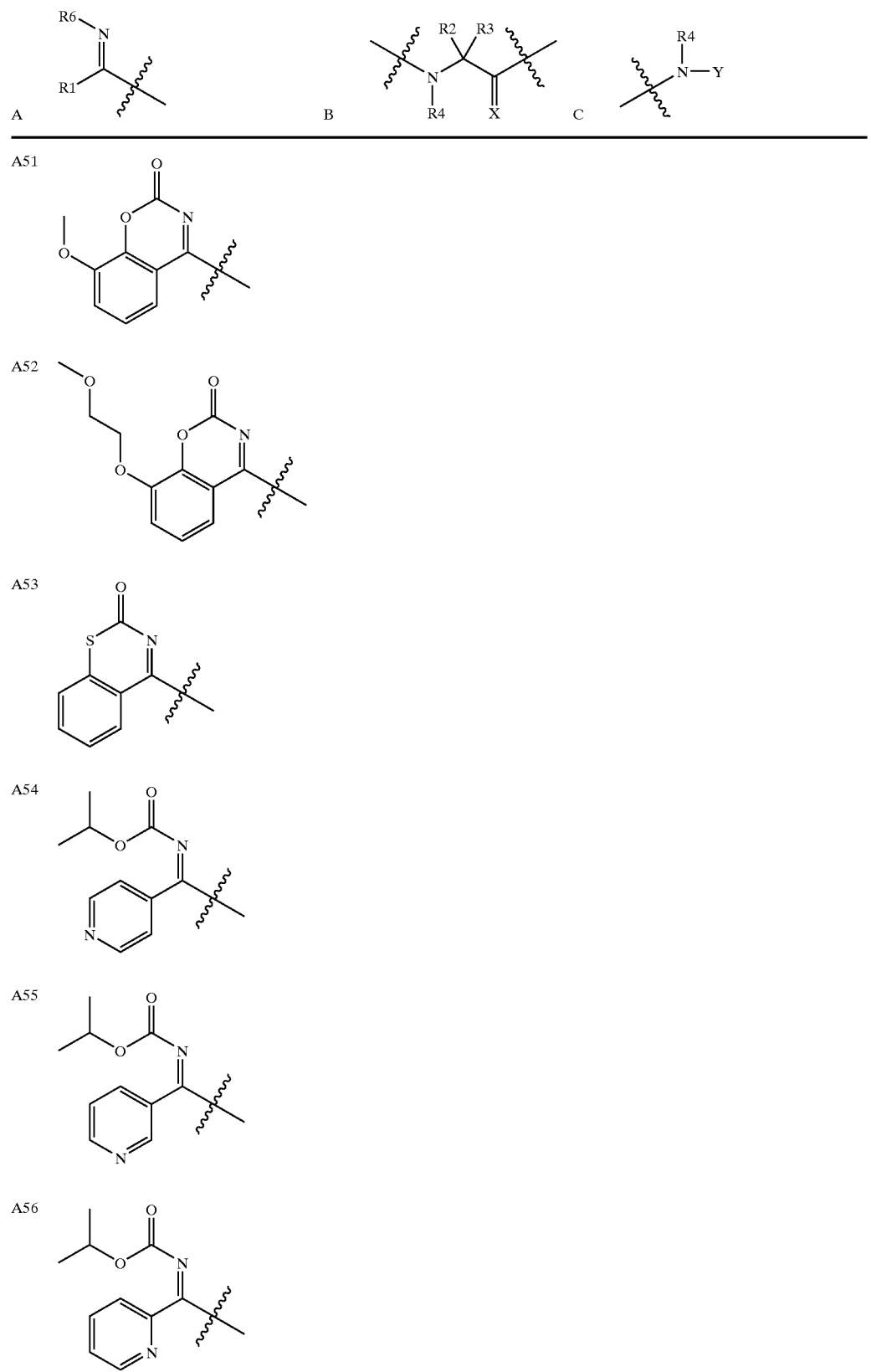

-continued
| A | B | C |
|---|---|---|
| 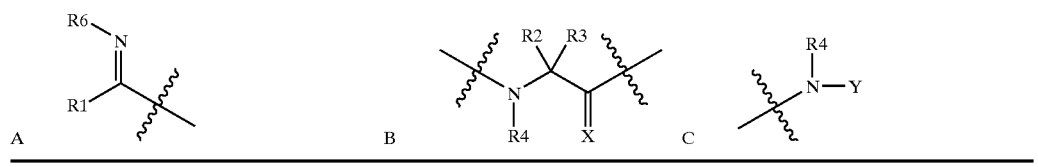 | | |
| A57 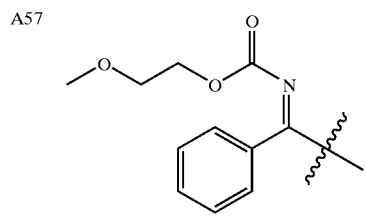 | | |
| A58 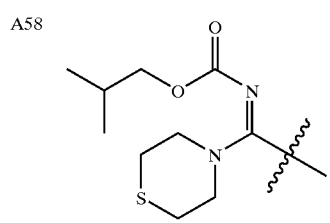 | | |
| A59 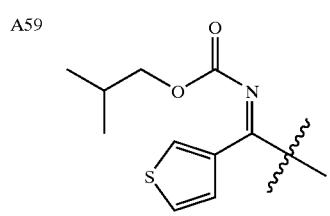 | | |
| A60 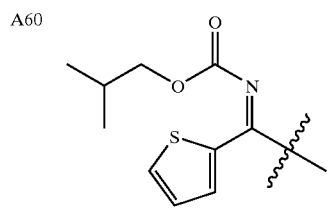 | | |
| A61 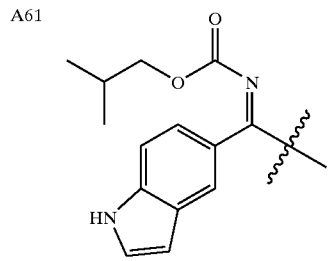 | | |
| A62 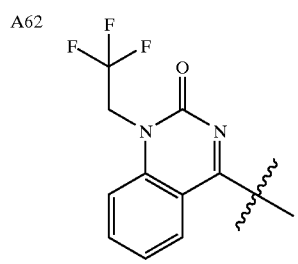 | | |

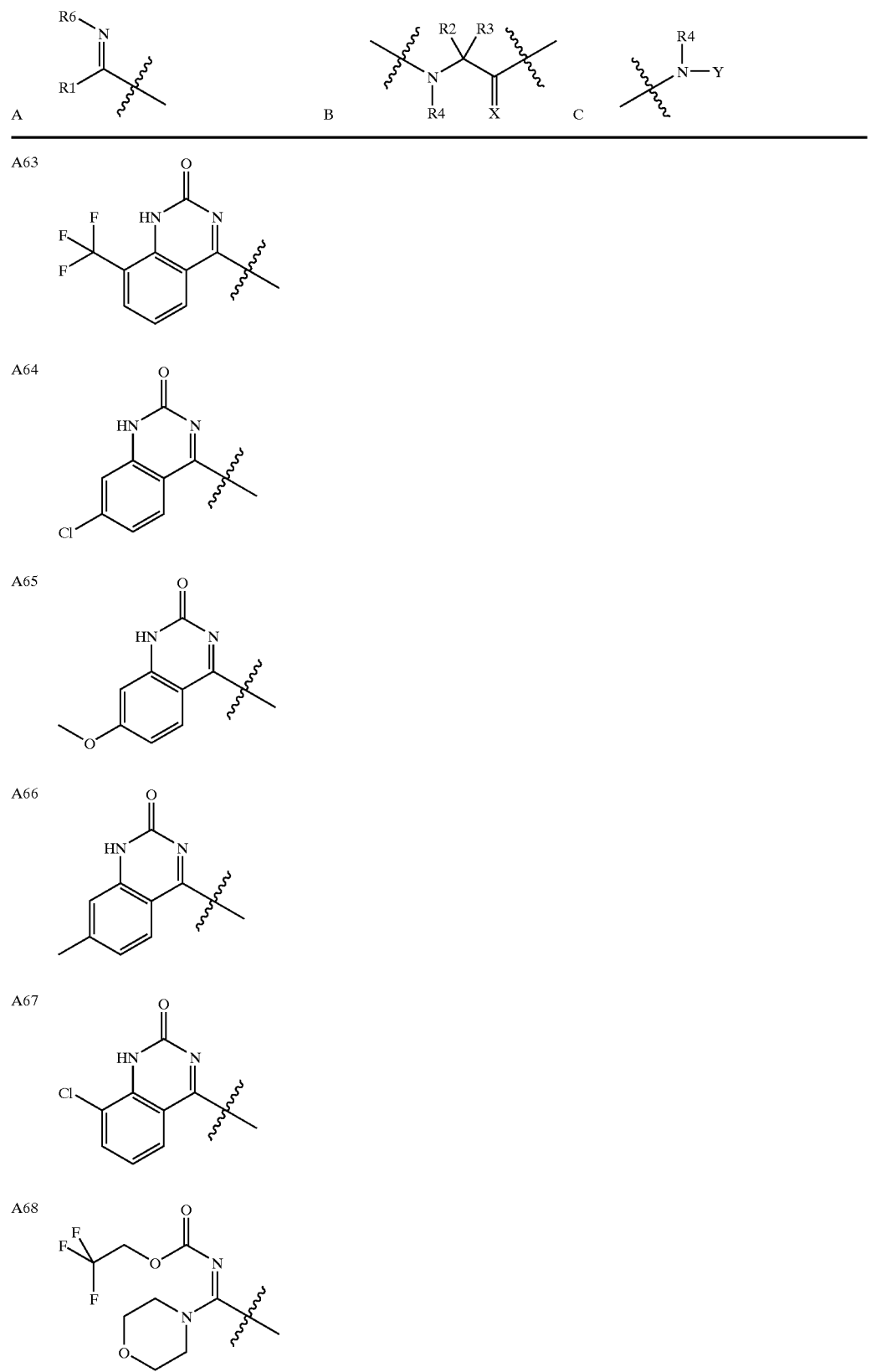

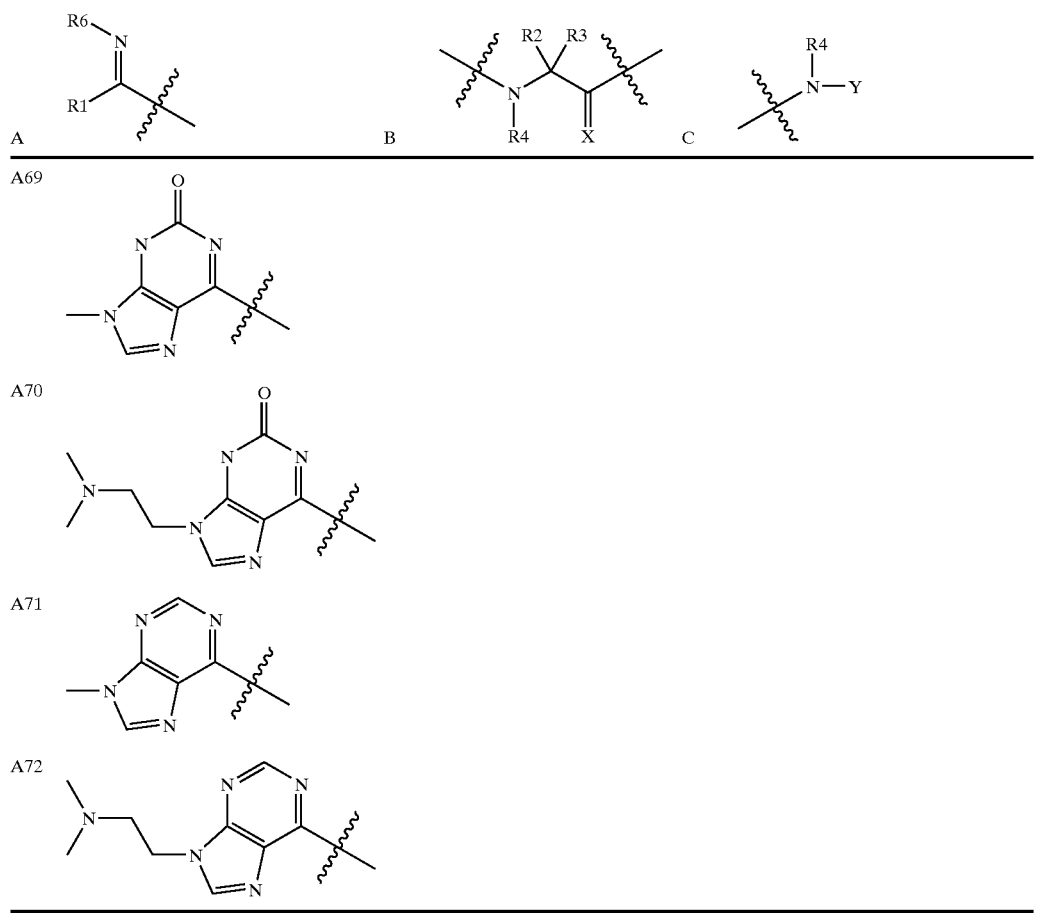

or the pharmaceutically acceptable salts, isomers or tautomers thereof.

20. A compound, wherein the compound is chosen from:

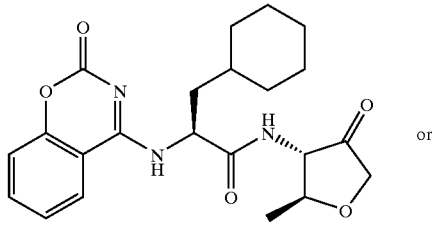 or

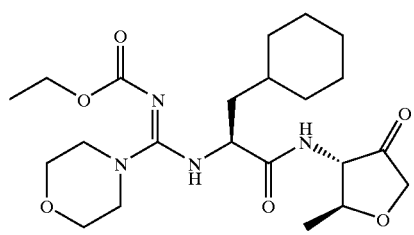

or or the pharmaceutically acceptable salts, isomers or tautomers thereof.

21. A pharmaceutical composition comprising a pharmaceutically effective amount of a compound according to claim 1.

22. A method of treating a disease chosen from rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis, endometriosis, or insulin-dependent diabetes mellitus comprising administering to a patient in need of such treatment a pharmaceutically effective amount of a compound according to claim 1.

23. A process of making a compound of the formula (Ia) according to claim 14:

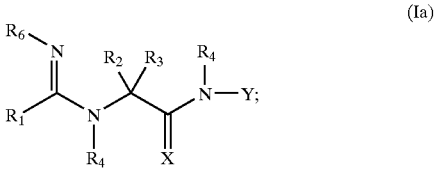

wherein for the formula (Ia), the components

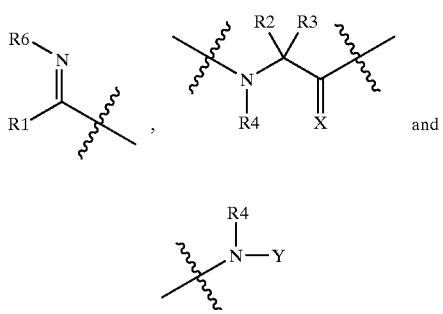

, and are as defined in claim 14, said process comprising:

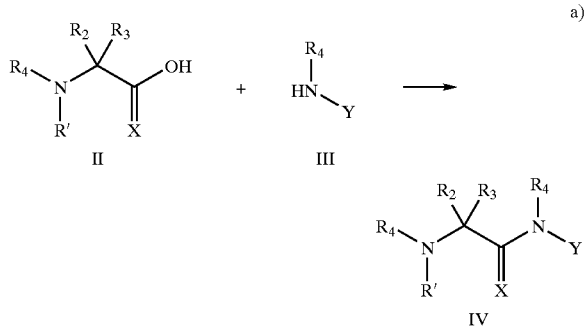

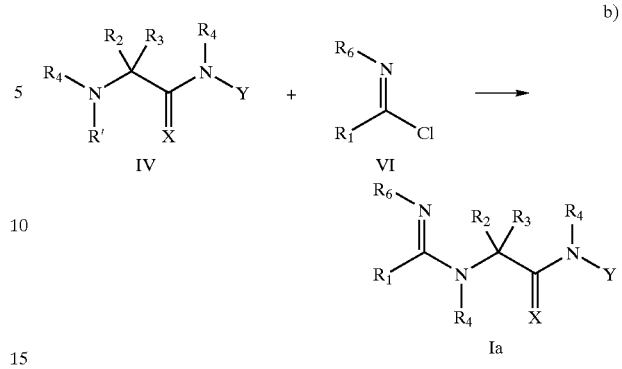

step a), reacting an amino acid bearing a suitable protecting group R' (II) with an amine bearing the group Y (III) under suitable coupling conditions to provide IV;

removing the protecting group R' under suitable deprotecting conditions;

step b), reacting the product of step a) with a halo imino compound (VI), in the presence of a suitable base to provide the product compound of formula (Ia) as defined above, and subsequently isolating said product compound.

* * * * *